US010976300B2

(12) United States Patent
Maglia et al.

(10) Patent No.: US 10,976,300 B2
(45) Date of Patent: Apr. 13, 2021

(54) MODIFIED NANOPORES, COMPOSITIONS COMPRISING THE SAME, AND USES THEREOF

(71) Applicant: Katholieke Universiteit Leuven, Leuven (BE)

(72) Inventors: Giovanni Maglia, Assen (NL); Lorenzo Franceschini, Leuven (BE); Tine Brouns, Lanaken (BE); Andrew John Heron, Oxford (GB); Lakmal Nishantha Jayasinghe, Oxford (GB); Elizabeth Jayne Wallace, Oxford (GB)

(73) Assignee: Katholieke Universiteit Leuven, Leuven (BE)

( * ) Notice: Subject to any disclaimer, the term of this patent is extended or adjusted under 35 U.S.C. 154(b) by 59 days.

(21) Appl. No.: 16/060,762

(22) PCT Filed: Dec. 8, 2016

(86) PCT No.: PCT/IB2016/001841
§ 371 (c)(1),
(2) Date: Jun. 8, 2018

(87) PCT Pub. No.: WO2017/098322
PCT Pub. Date: Jun. 15, 2017

(65) Prior Publication Data
US 2018/0364214 A1 Dec. 20, 2018

Related U.S. Application Data

(60) Provisional application No. 62/264,709, filed on Dec. 8, 2015.

(51) Int. Cl.
*G01N 33/487* (2006.01)
*C12Q 1/6869* (2018.01)
*C07K 14/00* (2006.01)

(52) U.S. Cl.
CPC ..... *G01N 33/48721* (2013.01); *C07K 14/001* (2013.01); *C12Q 1/6869* (2013.01)

(58) Field of Classification Search
CPC ............ G01N 33/48721; C07K 14/001; C12Q 1/6869; C12Q 2565/631
See application file for complete search history.

(56) References Cited

U.S. PATENT DOCUMENTS

| | | |
|---|---|---|
| 5,795,782 A | 8/1998 | Church et al. |
| 6,015,714 A | 1/2000 | Baldarelli et al. |
| 6,114,121 A | 9/2000 | Fujiwara et al. |
| 6,362,002 B1 | 3/2002 | Denison et al. |
| 6,426,231 B1 | 7/2002 | Bayley et al. |
| 6,627,067 B1 | 9/2003 | Branton et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 9,073,990 B2 * | 7/2015 | Paas ........................ B82Y 5/00 |
| 9,127,313 B2 | 9/2015 | Brown et al. |
| 9,222,082 B2 | 12/2015 | Jayasinghe et al. |
| 9,447,152 B2 | 9/2016 | Clarke et al. |
| 9,562,887 B2 | 2/2017 | Maglia et al. |
| 9,580,480 B2 | 2/2017 | Lu et al. |
| 9,588,079 B2 | 3/2017 | Gundlach et al. |
| 9,732,381 B2 | 8/2017 | Stoddart et al. |
| 9,751,915 B2 | 9/2017 | Clarke et al. |
| 9,777,049 B2 | 10/2017 | Bruce et al. |
| 10,006,905 B2 | 6/2018 | Maglia et al. |
| 10,167,503 B2 | 1/2019 | Clarke et al. |
| 10,266,885 B2 | 4/2019 | Jayasinghe et al. |
| 10,385,389 B2 | 8/2019 | Heron et al. |
| 10,400,014 B2 | 9/2019 | Howorka et al. |
| 10,443,097 B2 | 10/2019 | Jayasinghe et al. |
| 10,472,673 B2 | 11/2019 | Maglia et al. |
| 10,514,378 B2 | 12/2019 | Maglia et al. |
| 10,669,581 B2 | 6/2020 | Stoddart et al. |
| 2002/0028458 A1 | 3/2002 | Lexow |

(Continued)

FOREIGN PATENT DOCUMENTS

| | | |
|---|---|---|
| CA | 2381139 A1 | 3/2001 |
| CN | 102116783 A | 7/2011 |

(Continued)

OTHER PUBLICATIONS

[No Author Listed] EBI Accession No. A0A085GH19. Oct. 29, 2014.
[No Author Listed] EBI Accession No. A0A0D1LDB9. Apr. 29, 2015.
[No Author Listed] EBI accession No. EMBLCDS:ABV05494. Sep. 11, 2007.
Bianco et al., Helicase unwinding: active or merely perfect? J Mol Biol. Jul. 13, 2012;420(3):139-40. doi: 10.1016/j.jmb.2012.04.030. Epub May 2, 2012.

(Continued)

*Primary Examiner* — Ruixiang Li
(74) *Attorney, Agent, or Firm* — Wolf, Greenfield & Sacks, P.C.

(57) ABSTRACT

Provided herein relate to modified or mutant forms of cytolysin A (ClyA) and compositions comprising the same. In particular, the modified or mutant forms of ClyA permits efficient capture and/or translocation of a target negative-charged molecule or polymer through the modified or mutant ClyA nanopores at low or physiological ionic strengths. Thus, methods for using the modified or mutant forms of ClyA and compositions, for example, for characterizing a target negatively-charged analyte, e.g., a target polynucleotide, are also provided.

13 Claims, 20 Drawing Sheets
Specification includes a Sequence Listing.

(56) References Cited

U.S. PATENT DOCUMENTS

| | | |
|---|---|---|
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |
| 2003/0211502 A1 | 11/2003 | Sauer et al. |
| 2003/0215881 A1 | 11/2003 | Bayley et al. |
| 2004/0214177 A1 | 10/2004 | Bension |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0311582 A1 | 12/2008 | Bayley et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2009/0298188 A1 | 12/2009 | Peti-Peterdi |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | Mckeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0175663 A1 | 6/2015 | Yokoi et al. |
| 2015/0177237 A1 | 6/2015 | Turner et al. |
| 2015/0346149 A1 | 12/2015 | Brown et al. |
| 2016/0010147 A1 | 1/2016 | Heron et al. |
| 2016/0005330 A1 | 2/2016 | Maglia et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0209952 A1 | 7/2018 | Maglia et al. |
| 2018/0334707 A1 | 11/2018 | Stoddart et al. |
| 2018/0335425 A1 | 11/2018 | Maglia et al. |
| 2019/0071721 A1 | 3/2019 | Jayasinghe et al. |
| 2019/0300582 A1 | 10/2019 | Jayasinghe et al. |
| 2019/0330282 A1 | 10/2019 | Jayasinghe et al. |
| 2019/0346431 A1 | 11/2019 | Maglia et al. |
| 2020/0017556 A1 | 1/2020 | Howorka et al. |
| 2020/0072824 A1 | 3/2020 | Maglia et al. |
| 2020/0087724 A1 | 3/2020 | Heron et al. |
| 2020/0224262 A1 | 7/2020 | Jayasinghe et al. |

FOREIGN PATENT DOCUMENTS

| | | |
|---|---|---|
| CN | 102317310 A | 1/2012 |
| EP | 2194123 B1 | 8/2012 |
| EP | 2682460 | 1/2014 |
| GB | 2453377 | 4/2009 |
| JP | H10-146190 | 6/1998 |
| JP | 2005-253427 | 9/2005 |
| JP | 2015-514128 A | 5/2015 |
| WO | WO 1999/005167 | 2/1999 |
| WO | WO 2000/028312 | 5/2000 |
| WO | WO 2001/042782 | 6/2001 |
| WO | WO 2001/059453 | 8/2001 |
| WO | WO 2002/042496 | 5/2002 |
| WO | WO 2003/095669 | 11/2003 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2008/102120 | 8/2008 |
| WO | WO 2008/102121 | 8/2008 |
| WO | WO 2008/124107 | 10/2008 |
| WO | WO 2009/024775 A1 | 2/2009 |
| WO | WO 2009/035647 | 3/2009 |
| WO | WO 2009/044170 A1 | 4/2009 |
| WO | WO 2009/077734 A2 | 6/2009 |
| WO | WO 2009/143425 A1 | 11/2009 |
| WO | WO 2010/004265 | 1/2010 |
| WO | WO 2010/004273 | 1/2010 |
| WO | WO 2010/034018 | 3/2010 |
| WO | WO 2010/055307 A1 | 5/2010 |
| WO | WO 2010/086602 A1 | 8/2010 |
| WO | WO 2010/086603 | 8/2010 |
| WO | WO 2010/086622 | 8/2010 |
| WO | WO 2010/122293 | 10/2010 |
| WO | WO 2011/067559 | 6/2011 |
| WO | WO 2012/042226 | 4/2012 |
| WO | WO 2012/107778 A2 | 8/2012 |
| WO | WO 2012/164270 A1 | 12/2012 |
| WO | WO 2013/014451 | 1/2013 |
| WO | WO 2013/041878 A1 | 3/2013 |
| WO | WO 2013/057495 | 4/2013 |
| WO | WO 2013/098561 | 7/2013 |
| WO | WO 2013/098562 | 7/2013 |
| WO | WO 2013/109970 A1 | 7/2013 |
| WO | WO 2013/153359 | 10/2013 |
| WO | WO 2014/013259 | 1/2014 |
| WO | WO 2014/013260 | 1/2014 |
| WO | WO 2014/013262 | 1/2014 |
| WO | WO 2014/064443 A1 | 5/2014 |
| WO | WO 2014/064444 A1 | 5/2014 |
| WO | WO 2014/122654 A2 | 8/2014 |
| WO | WO 2014/135838 | 9/2014 |
| WO | WO 2014/153047 A1 | 9/2014 |
| WO | WO 2014/153625 A1 | 10/2014 |
| WO | WO 2015/022544 | 2/2015 |
| WO | WO 2015/051378 A1 | 4/2015 |
| WO | WO 2015/055981 | 4/2015 |
| WO | WO 2015/110777 | 7/2015 |
| WO | WO 2015/124935 | 8/2015 |
| WO | WO 2015/150786 | 10/2015 |
| WO | WO 2015/150787 | 10/2015 |
| WO | WO 2015/166276 A1 | 11/2015 |
| WO | WO 2016/055778 A1 | 4/2016 |
| WO | WO 2016/166232 A1 | 10/2016 |

OTHER PUBLICATIONS

Bourdon et al., Molecular cloning and sequence analysis of a chondroitin sulfate proteoglycan cDNA. Proc Natl Acad Sci U S A. Mar. 1985;82(5):1321-5.

Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.

Cao et al., Structure of the nonameric bacterial amyloid secretion channel. Proc Natl Acad Sci USA. Dec. 16, 2014;111(50):E5439-44. doi: 10.1073/pnas.1411942111. Epub Dec. 1, 2014.

Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.

Franceschini et al., A nanopore machine promotes the vectorial transport of DNA across membranes. Sep. 2013; Nat Commun. 2013;4:2415. doi: 10.1038/ncomms3415.

Goyal et al., Structural and mechanistic insights into the bacterial amyloid secretion channel CsgG. Nature. Dec. 11, 2014;516(7530):250-3. doi: 10.1038/nature13768. Epub Sep. 14, 2014.

(56) References Cited

OTHER PUBLICATIONS

Guasch et al., Detailed architecture of a DNA translocating machine: the high-resolution structure of the bacteriophage phi29 connector particle. J Mol Biol. Jan. 25, 2002;315(4):663-76.
Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.
Pavlenok et al., Hetero-oligomeric MspA pores in *Mycobacterium smegmatis*. FEMS Microbiol Lett. Apr. 2016;363(7). pii: fnw046. doi:10.1093/femsle/fnw046. Epub Feb. 23, 2016.
Pavlenok et al., MspA nanopores from subunit dimers. PLoS One. 2012;7(6):e38726. doi: 10.1371/journal.pone.0038726. Epub Jun. 18, 2012.
Rasko et al., The pangenome structure of *Escherichia coli*: comparative genomic analysis of *E. coli* commensal and pathogenic isolates. J Bacteriol. Oct. 2008;190(20):6881-93. doi:10.1128/JB.00619-08. Epub Aug. 1, 2008.
Robinson et al., Secretion of curli fibre subunits is mediated by the outer membrane-localized CsgG protein. Mol Microbiol. Feb. 2006;59(3):870-81.
Taylor et al., Atomic resolution insights into curli fiber biogenesis. Structure. Sep. 7, 2011;19(9):1307-16. doi: 10.1016/j.str.2011.05.015.
Van Gerven et al., Secretion and functional display of fusion proteins through the curlibiogenesis pathway. Mol Microbiol. Mar. 2014;91(5):1022-35. doi:10.1111/mmi.12515. Epub Feb. 12, 2014.
Wallace et al., *E. coli* hemolysin E (HlyE, ClyA, SheA): X-ray crystal structure of the toxin and observation of membrane pores by electron microscopy. Cell. Jan. 21, 2000;100(2):265-76.
[No Author Listed] Helicos BioSciences Corporation, "Helicos Genetic Analysis System," Specification Sheet retrieved online at: www.helicosbio.com/Portals/0/Documents/Helicos_SalesSpec.pdf, 4 pages. (2008).
Ahern, Biochemical, reagents kits offer scientists good return on investment. The Scientist. Jul. 24, 1995;9(15):20.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Aoki et al., Single channel properties of lysenin measured in artificial lipid bilayers and their applications to biomolecule detection. Proc Jpn Acad Ser B Phys Biol Sci. 2010;86(9):920-5.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Atkins et al., Structure-function relationships of a novel bacterial toxin, hemolysin E. The role of alpha G. J Biol Chem. Dec. 29, 2000;275(52):41150-5.
Avrameas, Coupling of enzymes to proteins with glutaraldehyde. Use of the conjugates for the detection of antigens and antibodies. Immunochemistry. Jan. 1969;6(1):43-52.
Bayley et al., Stochastic sensors inspired by biology. Nature. Sep. 13, 2001;413(6852):226-30.
Bayley et al., Wrestling with native chemical ligation. ACS Chem Biol. Dec. 18, 2009;4(12):983-5. doi: 10.1021/cb900304p.
Bayley, Membrane-protein structure: Piercing insights. Nature. Jun. 4, 2009;459(7247):651-2. doi: 10.1038/459651a.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., A Novel DNA Sensing Technique Using Nanopore MSPA. 54th Annual Meeting of the Biophysical Society, Poster 2182-Plat, 2 pages (2010).
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dorre et al., Techniques for single molecule sequencing. Bioimaging, vol. 5:139-152 (1997).
EBI accession No. GSP:AXX09397. May 13, 2010.
EID et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).

(56) References Cited

OTHER PUBLICATIONS

Eliseev et al., Molecular Recognition of Nucleotides, Nucleosides, and Sugars by Aminocyclodextrins. J. Am. Chem. Soc., vol. 116:6081-6088 (1994).

Engelhardt et al., A tetrameric porin limits the cell wall permeability of *Mycobacterium smegmatis*. J Biol Chem. Oct. 4, 2002;277(40):37567-72. Epub Jul. 18, 2002.

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.

Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.

Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gu et al., Capture of a single molecule in a nanocavity. Science. Jan. 26, 2001;291(5504):636-40.

Gu et al., Electroosmotic enhancement of the binding of a neutral molecule to a transmembrane pore. Proc Natl Acad Sci U S A. Dec. 23, 2003;100(26):15498-503. Epub Dec. 15, 2003.

Gu et al., Interaction of the noncovalent molecular adapter, beta-cyclodextrin, with the staphylococcal alpha-hemolysin pore. Biophys J. Oct. 2000;79(4):1967-75.

Gu et al., Prolonged residence time of a noncovalent molecular adapter, beta-cyclodextrin, within the lumen of mutant alpha-hemolysin pores. J Gen Physiol. Nov. 2001;118(5):481-94.

Gu et al., Reversal of charge selectivity in transmembrane protein pores by using noncovalent molecular adapters. Proc Natl Acad Sci U S A. Apr. 11, 2000;97(8):3959-64.

Gu et al., Stochastic sensing of organic analytes by a pore-forming protein containing a molecular adapter. Nature. Apr. 22, 1999;398(6729):686-90.

Guan et al., Stochastic sensing of TNT with a genetically engineered pore. Chembiochem. Oct. 2005;6(10):1875-81.

Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.

Han et al., Characterization and optimization of an entropic trap for DNA separation. Anal Chem. Jan. 15, 2002;74(2):394-401.

Han et al., RecJ exonuclease: substrates, products and interaction with SSB. Nucleic Acids Res. Feb. 18, 2006;34(4):1084-91. Print 2006.

Haque et al., Solid-State and Biological Nanopore for Real-Time Sensing of Single Chemical and Sequencing of DNA. Nano Today. Feb. 2013;8(1):56-74.

He et al. 2012; The T4 phage SF1 B helicase dda is structurally optimized to perform DNA strand separation. Structure. 20:1189-1200.

Henrickson et al., Driven DNA transport into an asymmetric nanometer-scale pore. Phys Rev Lett. Oct. 2, 2000;85(14):3057-60.

Heron et al., Direct detection of membrane channels from gels using water-in-oil droplet bilayers. J Am Chem Soc. Dec. 26, 2007;129(51):16042-7. Epub Dec. 1, 2007.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

Howorka et al., DNA Duplex Formation of Individual DNA Strands within a Single Protein Pore. Biophysical J. 2002;82:508a.

Howorka et al., Kinetics of duplex formation for individual DNA strands within a single protein nanopore. Proc Natl Acad Sci U S A. Nov. 6, 2001;98(23):12996-3001. Epub Oct. 23, 2001.

Howorka et al., Nanopores as protein sensors. Nat Biotechnol. Jun. 7, 2012;30(6):506-7. doi: 10.1038/nbt.2264.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.

Hwang et al., Electrical behavior of droplet interface bilayer networks: experimental analysis and modeling. J Am Chem Soc. Sep. 26, 2007;129(38):11854-64. Epub Sep. 1, 2007.

Iacovache et al., Structure and assembly of pore-forming proteins. Curr Opin Struct Biol. Apr. 2010;20(2):241-6. doi:10.1016/j.sbi.2010.01.013. Epub Feb. 19, 2010.

Ide et al., Lysenin forms a voltage-dependent channel in artificial lipid bilayer membranes. Biochem Biophys Res Commun. Jul. 21, 2006;346(1):288-92. Epub May 26, 2006.

Ivanov et al., DNA tunneling detector embedded in a nanopore. Nano Lett. Jan. 12, 2011;11(1):279-85. doi: 10.1021/nl1103873a. Epub Dec. 6, 2010.

Jayasinghe et al., The leukocidin pore: evidence for an octamer with four LukF subunits and four LukS subunits alternating around a central axis. Protein Sci. Oct. 2005;14(10):2550-61.

Johnston et al., Coexpression of proteins in bacteria using T7-based expression plasmids: expression of heteromeric cell-cycle and transcriptional regulatory complexes. Protein Expr Purif. Dec. 2000;20(3):435-43.

Jung et al., The internal cavity of the staphylococcal alpha-hemolysin pore accommodates approximately 175 exogenous amino acid residues. Biochemistry. Jun. 28, 2005;44(25):8919-29.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Khulbe et al., DNA translocation through a-hemolysin nanopores with potential application to macromolecular data storage. Journal Applied Physics, vol. 97(104317):1-7 (2005).

Kobayashi et al., Comparative Physiology and Biochemistry, 2005, vol. 22, No. 3-4, pp. 139-148.

Kumar et al., PEG-labeled nucleotides and nanopore detection for single molecule DNA sequencing by synthesis. Sci Rep. 2012;2:684. Epub Sep. 21, 2012.

Langecker et al., Synthetic lipid membrane channels formed by designed DNA nanostructures. Science. Nov. 16, 2012;338(6109):932-6. doi: 10.1126/science.1225624.

Li et al., DNA molecules and configurations in a solid-state nanopore microscope. Nat Mater. Sep. 2003;2(9):611-5. Epub Aug. 24, 2003.

(56) References Cited

OTHER PUBLICATIONS

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Luo et al., Influence of polymer-pore interactions on translocation. Phys Rev Lett. Oct. 5, 2007;99(14):148102. Epub Oct. 1, 2007.

Maglia et al., DNA strands from denatured duplexes are translocated through engineered protein nanopores at alkaline pH. Nano Lett. Nov. 2009;9(11):3831-6. doi: 10.1021/nl9020232.

Maglia et al., Engineering a Biomimetic Biological Nanopore to Selectively Capture Folded Target Proteins. Biophysical J. Feb. 5, 2013;104(2):518a.

Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.

Manrao et al., Nucleotide Discrimination with DNA Immobilized in the MspA Nanopore. PLoS One, vol. 6(10):e25723, 7 pages (2011).

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Manrao et al., Single Nucleotide Discrimination in Single Stranded DNA Immobilized within Biological Nanopre MSPA. 54th Annual Meeting of the Biophysical Society, 3 pages (2010).

Martin et al., Nanoscale protein pores modified with PAMAM dendrimers. J Am Chem Soc. Aug. 8, 2007;129(31):9640-9. Epub Jul. 18, 2007.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Mitchell et al., Chemical tags facilitate the sensing of individual DNA strands with nanopores. Angew Chem Int Ed Engl. 2008;47(30):5565-8. doi:10.1002/anie.200800183.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Moreau et al., Coupling ion channels to receptors for biomolecule sensing. Nat Nanotechnol. Oct. 2008;3(10):620-5. doi: 10.1038/nnano.2008.242. Epub Sep. 7, 2008.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R 1365- R1393 (2003).

Pfeiffer et al., Bivalent cholesterol-based coupling of oligonucletides to lipid membrane assemblies. J Am Chem Soc. Aug. 25, 2004;126(33):10224-5.

Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.

Rhee et al., Nanopore sequencing technology: research trends and applications. Trends Biotechnol. Dec. 2006;24(12):580-6. Epub Oct. 19, 2006.

Rotem et al., Protein detection by nanopores equipped with aptamers. J Am Chem Soc. Feb. 8, 2012;134(5):2781-7. doi:10.1021/ja2105653. Epub Jan. 26, 2012.

Russo et al., Reversible permeabilization of plasma membranes with an engineered switchable pore. Nat Biotechnol. Mar. 1997;15(3):278-82.

Saariaho et al., Characteristics of MuA transposase-catalyzed processing of model transposon end DNA hairpin substrates. Nucleic Acids Res. Jun. 6, 2006;34(10):3139-49.

Sanchez-Quesada et al., Cyclic Peptides as Molecular Adapters for a Pore-Forming Protein. Journal American Chemical Society, vol. 122(48):11757-11766 (2000).

Sanchez-Quesada et al., Single DNA rotaxanes of a transmembrane pore protein. Angew Chem Int Ed Engl. Jun. 7, 2004;43(23):3063-7.

Sanderson, Personal genomes: Standard and pores. Nature. Nov. 6, 2008;456(7218):23-5. doi: 10.1038/456023a.

Sauer-Budge et al., Unzipping kinetics of double-stranded DNA in a nanopore. Phys Rev Lett. Jun. 13, 2003;90(23):238101. Epub Jun. 9, 2003.

Smeets et al., Salt dependence of ion transport and DNA translocation through solid-state nanopores. Nano Lett. Jan. 2006;6(1):89-95.

Soni et al., Synchronous optical and electrical detection of biomolecules traversing through solid-state nanopores. Rev Sci Instrum. Jan. 2010;81(1):014301. doi: 10.1063/1.3277116.

Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012.

Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Sutherland et al., An analysis of mismatched duplex DNA unzipping through a bacterial nanopore. Biochem Cell Biol. Jun. 2004;82(3):407-12.

Van De Goor, Nanopore Detection: Threading DNA Through a Tiny Hole. PharmaGenomics, vol. 4 (3):28-30 (2004).

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.

Wang et al., Nanopores with a spark for single-molecule detection. Nat Biotechnol. Jul. 2001;19(7):622-3.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wanunu, Nanopores: A journey towards DNA sequencing. Phys Life Rev. Jun. 2012;9(2):125-58. doi:10.1016/j.plrev.2012.05.010. Epub May 18, 2012.

(56) References Cited

OTHER PUBLICATIONS

Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
PCT/IB2016/001841, May 31, 2017, International Search Report and Written Opinion.
PCT/IB2016/001841, Jun. 21, 2018, International Preliminary Report on Patentability.
Invitation to Pay Additional Fees for Application No. PCT/IB2016/001841, dated Dec. 21, 2016.
[No Author Listed] Uniprot Accession No. A0A081NL13. Oct. 29, 2014. 4 pages.
[No Author Listed] Uniprot Accession No. A0A0P7DN88. Jan. 20, 2016. 4 pages.
Aravind et al., The DNA-Repair Protein AlkB, EGL-9, and Leprecan Define New Families of 2-oxoglutarate-andiron-Dependent Dioxygenases. Genome Biology. 2001;2:1-8.
Ashton et al., MinION Nanopore Sequencing Identifies the Position and Structure of a Bacterial antibiotic Resistance Island. Nat Biotechnol. Mar. 2015;33(3):296-302.
Bayley, Nanopore Sequencing: From Imagination to Reality. Clin Chem. 2015;61(1):25-31.
Bezrukov et al., Counting Polymers Moving Through a Single Ion Channel. Nature. Jul. 28, 1994;370:279-81.
Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.
Bleijlevens et al., Dynamic States of the DNA Repair Enzyme AlkB regulate Product Release. Eur Mol Biol Org. Jul. 11, 2008;9(9):872-77.
Chin et al., The Metabolite alpha-Ketoglutarate Extends Lifespan by Inhibiting ATP Synthase and TOR. Nature. Jul. 19, 2014;510:397-401.
Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.
Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.
Freedman et al., Single Molecule Unfolding and Stretching of Protein Domains Inside a Solid-State Nanopore by Electric Field. Scientific Reports. Apr. 10, 2013;3(1638):1-8.
Gilbert et al., Two Structural Transitions in Membrane Pore Formation by Pneumolysin, the Pore-Forming Toxin of *Streptococcus pneumoniae*. Cell. May 28, 1999;97:647-655.
Gouridis et al., Conformational Dynamics in Substrate-Binding Domains Influences Transport in the ABC Importer GinPQ. Nat Stuct Mol Biol. Dec. 8, 2014;22(1):57-66.
Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.
Howorka et al., Nanopore Analytics: Sensing of Single Molecules. The Royal Society of Chemistry. Jun. 15, 2009;38:2360-84.
Krylova et al., DNA aptamers for as analytical tools for the quantitative analysis of DNA-dealkylating enzymes. Anal Biochem. 2011;414(2):261-265. doi:10.1016/j.ab.2011.03.010.
Luchian et al., Single-Molecule Covalent Chemistry with Spatially Separated Reactants. Angew. Chem. Int. Ed. 2003;42:3766-771.
Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.
Makaram et al., Trends in Nanomaterial-Based Non-Invasive Diabetes Sensing Technologies. Diagnostics. Apr. 21, 2014;4:27-46.
Mikheyev et al., A First Look at the Oxford Nanopore MinION Sequencer. Mol Ecol Res. 2014;14:1097-1102.
Miles et al., The Staphylococcal Leukocidin Bicomponent Toxin Forms Large Ionic Channels. Biochemistry. Jun. 28, 2001;40:8514-522.
Miyazaki et al., MEGAWHOP Cloning: A Method of Creating Random Mutagenesis Libraries via Megaprimer PCR of Whole Plasmids. Methods in Enzymology. 2011;498:399-406.
Moyer et al., Correlation Between Sweat Glucose and Blood Glucose in Subjects with Diabetes. Diabetes Technol Ther. 2012:14(5):398-402.
Mueller et al., The Structure of Cytolytic alpha-Helical Toxin Pore Reveals its Assembly Mechanism. Nature. Jun. 4, 2009;459:726-731.
Niedzwiecki et al., Inspection of the Engineered FhuA deltaC/delta4L Protein Nanopore by Polymer Exclusion. Biophys J. Nov. 2012;103:2115-124.
Nikolaidou et al., alpha-Ketoglutarate: Biological Effects of a Novel Biomarker of Heart Failure. Heart. Sep. 2010;96(17). 2 pages.
Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.
Oukhaled et al., Dynamics of Completely Unfolded and Native Proteins through Solid-State Nanopores as a Function of Electric Driving Force. Am Chem Soc. 2011 Arp 8;5(5):3628-38.
Plesa et al., Fast Translocation of Proteins through Solid State Nanopores. Nano Lett. Jan. 23, 2013:13:658-663.
Quick et al., A reference Bacterial Genome Dataset Generated on the MinION Portable Single-Molecule Nanopore Sequencer. GigaScience. 2014;3(22):1-6.
Rajagopalan et al., Interaction of Dihydrofolate Reductase with Methotrexate: Ensemble and Single-Molecule Kinetics. PNAS. Oct. 15, 2002:99(21):13481-6.
Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.
Soskine et al., Single-Molecule Analyte Recognition with ClyA Nanopores Equipped with Internal Protein Adaptors. J Am Chem Soc. 2015;137:5793-97.
Trewick et al., Oxidative Demethylation by *Escherichia coli* AlkB Directly Reverts DNA Base Damage. Nature. Sep. 12, 2002:419:174-78.
Van Meervelt et al., Detection of Two Isomeric Binding Configurations in a Protein-Aptamer Complex with a Biological Nanopore. Am Chem Soc. Dec. 10, 2014;8(12):12826-35.
Welford et al., The Selectivity and Inhibition of AlkB. J. Biol. Chem. Mar. 21, 2003;278(12):10157-161.
Wendell et al., Translocation of double-stranded DNA through membrane-adapted phi29 motor protein nanopores. Nat Nanotechnol. 2009;4(11):765-772. doi:10.1038/nnano.2009.259.
White et al., Single Ion-Channel Recordings Using Glass Nanopore Membranes. J Am Chem Soc. 2007;129:11766-775.
Yoo et al., Glucose Biosensors: An Overview of Use in Clinical Practice. Sensores. May 4, 2010;10:4558-4576.
Zhou et al., Ion Channel Probes for Scanning Ion Conductance Microscopy. Langmuir. Nov. 25, 2014;30:15351-355.

\* cited by examiner

SEQUENCE LISTING

```
<160> NUMBER OF SEQ ID NOS: 10

<210> SEQ ID NO 1
<211> LENGTH: 303
<212> TYPE: PRT
<213> ORGANISM: S. typhi

<400> SEQUENCE: 1

Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
                20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Glu Ala Ser Val Leu Val Gly Asp
        50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
                100                 105                 110

Lys Asp Ile Leu Ile Arg Ile Leu Asp Asp Gly Val Lys Lys Leu Asn
            115                 120                 125

Glu Ala Gln Lys Ser Leu Leu Thr Ser Ser Gln Ser Phe Asn Asn Ala
        130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175
```

```
Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
            195                 200                 205

Pro Glu Leu Asn Asn Arg Leu Lys Thr Val Gln Asn Phe Phe Thr Ser
            210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
            245                 250                 255

Thr Glu Thr Thr Arg Phe Tyr Val Asp Tyr Asp Leu Met Leu Ser
            260                 265                 270

Leu Leu Lys Gly Ala Ala Lys Lys Met Ile Asn Thr Cys Asn Glu Tyr
            275                 280                 285

Gln Gln Arg His Gly Lys Lys Thr Leu Phe Glu Val Pro Asp Val
            290                 295                 300
```

<210> SEQ ID NO 2
<211> LENGTH: 312
<212> TYPE: PRT
<213> ORGANISM: S. typhi

<400> SEQUENCE: 2

```
Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Glu Ala Ser Val Leu Val Gly Asp
        50                  55                  60

Ile Lys Val Leu Leu Met Asp Ser Gln Asp Lys Tyr Phe Glu Ala Thr
65                  70                  75                  80

Gln Thr Val Tyr Glu Trp Ala Gly Val Val Thr Gln Leu Leu Ser Ala
            85                  90                  95

Tyr Ile Gln Leu Phe Asp Gly Tyr Asn Glu Lys Lys Ala Ser Ala Gln
            100                 105                 110

Lys Asp Ile Leu Ile Arg Ile Leu Asp Asp Gly Val Lys Lys Leu Asn
            115                 120                 125

Glu Ala Gln Lys Ser Leu Leu Thr Ser Ser Gln Ser Phe Asn Asn Ala
            130                 135                 140

Ser Gly Lys Leu Leu Ala Leu Asp Ser Gln Leu Thr Asn Asp Phe Ser
145                 150                 155                 160

Glu Lys Ser Ser Tyr Tyr Gln Ser Gln Val Asp Arg Ile Arg Lys Glu
            165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Val Glu Gly Lys Leu Ile
            195                 200                 205

Pro Glu Leu Asn Asn Arg Leu Lys Thr Val Gln Asn Phe Phe Thr Ser
            210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
```

|   |   |   | 245 |   |   |   | 250 |   |   |   | 255 |   |   |
|---|---|---|---|---|---|---|---|---|---|---|---|---|---|
| Thr | Glu | Thr | Thr | Arg | Phe | Tyr | Val | Asp | Tyr | Asp | Asp | Leu | Met | Leu | Ser |
|   |   |   | 260 |   |   |   | 265 |   |   |   | 270 |   |   |

Leu Leu Lys Gly Ala Ala Lys Lys Met Ile Asn Thr Ser Asn Glu Tyr
            275                 280                 285

Gln Gln Arg His Gly Arg Lys Thr Leu Phe Glu Val Pro Asp Val Gly
        290                 295                 300

Ser Ser Tyr His His His His
305             310

<210> SEQ ID NO 3
<211> LENGTH: 1194
<212> TYPE: DNA
<213> ORGANISM: S. typhi

<400> SEQUENCE: 3

```
cctgcgtaga taagcaggaa gcaggcagta tttccagctt ctggaatgtt aaagctacaa    60
aagttgtctg gaggtaatag gtaagaatac tttataaaac aggtacttaa ttgcaattta   120
tatatttaaa gaggcaaatg attatgaccg gaatatttgc agaacaaact gtagaggtag   180
ttaaaagcgc gatcgaaacc gcagatgggg cattagatct ttataacaaa tacctcgacc   240
aggtcatccc ctggaagacc tttgatgaaa ccataaaaga gttaagccgt tttaaacagg   300
agtactcgca ggaagcttct gttttagttg gtgattataa agttttgctt atggacagcc   360
aggacaagta ttttgaagcg acacaaactg tttatgaatg gtgtggtgtc gtgacgcaat   420
tactctcagc gtatatttta ctatttgatg aatataatga gaaaaaagca tcagcccaga   480
aagacattct cattaggata ttagatgatg gtgtcaagaa actgaatgaa gcgcaaaaat   540
ctctcctgac aagttcacaa agtttcaaca acgcttccgg aaaactgctg gcattagata   600
gccagttaac taatgatttt tcggaaaaaa gtagttattt ccagtcacag gtggatagaa   660
ttcgtaagga agcttatgcc ggtgctgcag ccggcatagt cgccggtccg tttggattaa   720
ttatttccta ttctattgct gcgggcgtga ttgaagggaa attgattcca gaattgaata   780
acaggctaaa aacagtgcaa aatttctttta ctagcttatc agctacagtg aaacaagcga   840
ataaagatat cgatgcggca aaattgaaat tagccactga aatagcagca attggggaga   900
taaaaacgga accgaaaaca accagattct acgttgatta tgatgattta atgctttctt   960
tattaaaagg agctgcaaag aaaatgatta acacctgtaa tgaataccaa caaagacacg  1020
gtaagaagac gctttttcgag gttcctgacg tctgatacat tttcattcga tctgtgtact  1080
tttaacgccc gatagcgtaa agaaaatgag agacggagaa aaagcgatat caacagccc  1140
gataaacaag agtcgttacc gggctgacga ggttatcagg cgttaagctg gtag        1194
```

<210> SEQ ID NO 4
<211> LENGTH: 945
<212> TYPE: DNA
<213> ORGANISM: S. typhi

<400> SEQUENCE: 4

```
atgacgggta tctttgcgga acagacggtg gaagttgtga aaagtgcgat tgaaacggct    60
gacggtgcgc tggacctgta ataaatatat ctggatcagg tcatcccgtg gaaaaccttt   120
gacgaaacga ttaaagaact gagccgtttc aaacaggaat acagtcaaga agcgtccgtc   180
ctagtgggcg atatcaaagt gctgctgatg gattctcagg acaaatattt tgaagctacc   240
caaacggttt acgaatgggc gggtgtggtt acccagctgc tgtccgcata tattcagctg   300
```

```
ttcgatggat acaatgagaa aaaagcgagc gcgcagaaag acattctgat ccgcattctg    360
gatgacggcg tgaaaaaact gaatgaagcc cagaaatcgc tgctgaccag ctctcaatca    420
tttaacaatg cctcgggtaa actgctggca ctggatagcc agctgacgaa cgacttttct    480
gaaaaaagtt cctattacca gagccaagtc gatcgtattc gtaaagaagc ctacgcaggt    540
gccgcagcag gtattgtggc cggtccgttc ggtctgatta tctcatattc aattgctgcg    600
ggcgttgtcg aaggtaaact gattccggaa ctgaacaatc gtctgaaaac cgttcagaac    660 ttttcacca gtctgtctgc tacggtcaaa caagcgaata agatatcga cgccgcaaaa    720 ctgaaactgg ccacggaaat cgctgcgatt ggcgaaatca aaaccgaaac ggaaaccacg    780
cgcttttatg ttgattacga tgacctgatg ctgagcctgc tgaaaggtgc cgcgaagaaa    840
atgattaata cctctaatga atatcagcag cgtcacggta gaaaaccct gtttgaagtc    900 ccggatgtgg gcagcagcta ccaccatcat caccactaaa agctt                   945
```

<210> SEQ ID NO 5
<211> LENGTH: 90
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: mod_res
<222> LOCATION: (90)..(90)
<223> OTHER INFORMATION: modified by 3' /3Bio/

<400> SEQUENCE: 5

```
ggatgacctg atccagatat ttattataca ggtccagcgc accgtcagcc caatcgcact    60
tttcacaaaa agagagagag atcgattacc                                      90
```

<210> SEQ ID NO 6
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 6

```
ggtaatcgat ctctctctct ttttgtgaaa agtgcgattg ggctgacggt gcgctggacc    60
tgtataataa atatctggat caggtcatcc                                      90
```

<210> SEQ ID NO 7
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: mod_res
<222> LOCATION: (59)..(59)
<223> OTHER INFORMATION: modified by 3' /3Bio/

<400> SEQUENCE: 7

```
ggtaatcgat ctctctctct ttttgtgaaa agtgcgattg ggctgacggt gcgctggac     59
```

<210> SEQ ID NO 8
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:

```
<221> NAME/KEY: mod_res
<222> LOCATION: (31)..(31)
<223> OTHER INFORMATION: modified by 3' /3Bio/

<400> SEQUENCE: 8
ctgtataata aatatctgga tcaggtcatc c                                          31

<210> SEQ ID NO 9
<211> LENGTH: 100
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: mod_res
<222> LOCATION: (1)..(1)
<223> OTHER INFORMATION: modified by 5' /5Bio/

<400> SEQUENCE: 9
ccgtagtttg ggatgacctg atccagatat ttattataca ggtccagcgc accgtcagcc           60
caatcgcact tttcacaaaa agagagagag atcgattacc                                100

<210> SEQ ID NO 10
<211> LENGTH: 50
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: mod_res
<222> LOCATION: (1)..(1)
<223> OTHER INFORMATION: modified by 5' /5Bio/

<400> SEQUENCE: 10
ggtaatcgat ctctctctct ttttgtgaaa agtgcgattg ggctgacggt                      50
```

MODIFIED NANOPORES, COMPOSITIONS COMPRISING THE SAME, AND USES THEREOF

CROSS-REFERENCE TO RELATED APPLICATIONS

This application is a national stage application under U.S.C. § 371 of PCT International Application No. PCT/IB2016/001841, filed Dec. 8, 2016, which claims the benefit under 35 U.S.C. § 119(e) of U.S. provisional application No. 62/264,709 filed Dec. 8, 2015, the contents of each of which are incorporated herein by reference in their entireties.

TECHNICAL FIELD

Provided herein are modified or mutant forms of cytolysin A (ClyA) and compositions comprising the same. Methods for using the modified or mutant forms of ClyA and compositions, for example, for characterizing a target analyte, e.g., a target polynucleotide, are also provided.

BACKGROUND

Transmembrane pores (e.g., nanopores) have been used to identify small molecules or folded proteins and to monitor chemical or enzymatic reactions at the single molecule level. The electrophoretic translocation of DNA across nanopores reconstituted into artificial membranes holds great promise for practical applications such as DNA sequencing, and biomarker recognition. However, translocation of double-stranded or single-stranded DNA through nanopores having internal surface facing negatively charged amino acids are not efficient. In particular, in nanopores having a negative internal surface charge and radii comparable to the Debye length of the solution, the surface potential produced by the electric-double layer (EDL) on the inner nanopore walls overlaps, resulting in a large electrostatic barrier for the entry of DNA into the nanopore. As a consequence, the translocation of DNA across such nanopores has only been observed using large nanopores (e.g., 10 nm) or using small nanopores (e.g., ~3.5 nm) in high ionic strength solutions or under asymmetry salt concentrations.

SUMMARY

The present disclosure is based, at least in part, on the unexpected discovery that while certain protein nanopores, for example, a cytolysin A (ClyA) nanopore, has a negatively-charged narrow constriction (or a region which inhibits or reduces efficiency of translocation), successful capture and translocation of a negatively-charged molecule or polymer (e.g., double stranded or single stranded DNA) through such a protein nanopore having a negatively-charged narrow constriction in low ionic strength solutions can be achieved by introducing positive charges, for example, positively-charged amino acids (e.g., arginines), within the luminal surface of the protein nanopore (e.g., ClyA nanopore) to capture and orient the negatively-charged molecule or polymer (e.g., double stranded or single stranded DNA) within the nanopore. For example, positive charges, e.g., positively-charged amino acids (e.g., arginines) can be introduced within the luminal surface of a protein nanopore having a negatively-charged narrow constriction (e.g., ClyA nanopore) near its opening (e.g., an opening for entry of a negatively-charged molecule or polymer) and within its midsection.

In certain examples, ClyA-AS, an engineered ClyA version selected for its advantageous properties in planar lipid bilayers, were used to create modified ClyA nanopores as described herein. The internal charges of ClyA-AS were rearranged to induce the capture of DNA by the nanopores at physiological ionic strengths. For example, the modified ClyA nanopore comprises a cis opening, a mid-section, and a trans opening, wherein an internal surface of the cis opening comprises a first positively-charged amino acid substitution; an internal surface of the mid-section comprises a second positively-charged amino acid substitution; and the trans opening comprises an electronegative constriction. In some instances, the first positively-charged amino acid substitution (e.g., substitution with arginine) may be positioned within the cis opening so as to permit capture of a DNA into the modified ClyA nanopore and/or the second positively-charged amino acid substitution (e.g., substitution with arginine) may be positioned within the mid-section so as to permit translocation of the DNA through the modified ClyA nanopore. For example, the first positively-charged amino acid substitution may correspond to a S110R mutation in the amino acid sequence of ClyA-AS and/or the second positively-charged amino acid substitution may correspond to a D64R mutation in the amino acid sequence of ClyA-AS.

Accordingly, one aspect of the present disclosure features a modified ClyA nanopore, for example, that permits capture of a negatively-charged polymer into the modified ClyA nanopore and/or translocation of the negatively-charged polymer through the modified ClyA nanopore. The modified ClyA nanopore comprises a first opening, a mid-section, a second opening, and a lumen extending from the first opening through the mid-section to the second opening, wherein a luminal surface of the first opening comprises a first positive charge modification (e.g., a first positively-charged amino acid substitution) and a luminal surface of the mid-section comprises a second positive charge modification (e.g., a second positively charged amino acid substitution). The luminal surface of the second opening defines an electronegative constriction.

In any of the modified ClyA nanopores described herein, the distance within the lumen from the first positive charge modification (e.g., the first positively-charged amino acid substitution) to the second positive charge modification (e.g., the second positively charged amino acid substitution) may vary within a range of about 0.5 nm to about 10 nm. In some embodiments, the distance within the lumen from the first positive charge modification (e.g., the first positively-charged amino acid substitution) to the first opening surface may vary within a range of about 3 nm to about 7 nm.

Any forms of ClyA may be used to produce the modified ClyA nanopore described herein. For example, the amino acid sequences of wild-type ClyA (ClyA-WT) and ClyA-AS, and nucleotide sequences encoding the same are known in the art. Accordingly, in some embodiments, the modified ClyA nanopore may comprise a subunit polypeptide having an amino acid sequence that is at least about 80% (including, e.g., at least about 85%, at least about 90%, at least about 95%, or higher) identical to the amino acid sequence as set forth in SEQ ID NO: 1, which corresponds to the wild-type ClyA. Alternatively, the modified ClyA nanopore may comprise a subunit polypeptide having an amino acid sequence that is at least about 80% (including, e.g., at least about 85%, at least about 90%, at least about 95%, or higher) identical to the amino acid sequence as set forth in SEQ ID NO: 2, which corresponds to ClyA-AS. In some embodiments, the modified ClyA nanopore may comprise up to 15 substitutions compared to the amino acid sequences as set forth in SEQ ID NO: 1 or SEQ ID NO: 2 including the first and second positively-charged amino acid substitutions.

In any of the modified ClyA nanopores described herein, the first positive charge modification (e.g., the first positively-charged amino acid substitution) may be positioned within the first opening so as to permit capture of a negatively charged polymer (e.g., but not limited to a deoxyribonucleic acid (DNA) such as double stranded DNA or single-stranded DNA) within a solution exposed to the first opening. For example, substitution with a positive charge (e.g., a positively-charged amino acid) may take place at one of more of the following positions: E106, D114, D121, D122, E129, E85, E78, D268, D267, D265, E258 of SEQ ID NO: 1 or SEQ ID NO: 2.

In any of the modified ClyA nanopores described herein, the second positive charge modification (e.g., the second positively-charged amino acid substitution) may be positioned within the mid-section so as to permit translocation of the negatively charged polymer (e.g., but not limited to a deoxyribonucleic acid (DNA) such as double stranded DNA or single-stranded DNA) through the lumen of the pore. For example, substitution with a positive charge (e.g., a positively-charged amino acid) may take place at one of more of the following positions: D74, D71, D64, E53, E161, D158, E46, E42, D41 of SEQ NO: 1 or SEQ ID NO: 2.

The distance between the first and second positive charge modifications (e.g., the first and second positively-charged substitutions) is preferably from about 0.5nm to about 10 nm. The distance may be between from about 3 nm to about 7nm.

The modified ClyA nanopore can be homo-multimeric (e.g., all subunits within the nanopore are the same) or hetero-multimeric (e.g., at least one subunit is different from others within the nanopore). The modified ClyA nanopore may comprise any number of subunit polypeptides that are sufficient to form a lumen large enough to permit a target polymer (e.g., polynucleotide) pass through. In some embodiments, the modified ClyA nanopore may comprise 12 subunit polypeptides or more, including, e.g., 13 subunit polypeptides, and 14 subunit polypeptides, wherein at least one or more of the subunit polypeptides comprises the first and second positively-charged amino acid substitutions as described herein.

The first and second positive charge modifications (e.g., the first and second positively-charged amino acid substitutions) may take place in all the subunits of the nanopore.

Accordingly, modified ClyA nanopore subunit polypeptide and polynucleotides comprising nucleotide sequences encoding the modified ClyA nanopore subunit polypeptides are also provided herein. For example, the modified ClyA nanopore subunit polypeptide comprises an amino acid sequence that is at least about 80% (including, e.g., at least about 85%, at least about 90%, at least about 95%, or higher) identical to the amino acid sequence as set forth in SEQ ID NO: 1 or SEQ ID NO: 2, and wherein the amino acid sequence comprises a first positive charge modification (e.g., a first positively-charged amino acid substitution) at a position within a range of 106-78 of SEQ ID NO: 1 or SEQ ID NO: 2 and a second positive charge modification (e.g., a second positively-charged amino acid substitution) at a position within a range of 41-74 of SEQ ID NO: 1 or SEQ ID NO: 2. In one example, the first positive charge modification (e.g., the first positively-charged amino acid substitution) may be located at position 110 of SEQ ID NO: 1 or SEQ ID NO: 2; and/or the second positive charge modification (e.g., the second positively-charged amino acid substitution) may be located at position 64 of SEQ ID NO: 1 or SEQ ID NO:2. Examples of the first and/or second positively-charged amino acid substitutions include, but are not limited to substitution with one of an arginine, a histidine, and a lysine.

Also within the scope of the present disclosure are compositions, for example, for use in characterizing a target polymer, e.g., a target negative-charged polymer such as a target polynucleotide. The composition comprises any of the modified ClyA nanopores described herein. The composition may further comprise a membrane (e.g., an artificial membrane) in which the modified ClyA nanopore is situated. The composition may further comprise a low ionic strength solution, for example, a salt solution having an ionic strength of about 100 mM to about 300 mM or about 150 mM to about 300 mM. More generally the salt solution may have an ionic strength of about 50mM to about 1M. In some embodiments, the composition may further comprise a polynucleotide binding protein, which can be optionally coupled to the modified ClyA nanopore.

The modified ClyA nanopores and compositions as described herein can be used for various biosensor or analyte detection applications, but not limited to polynucleotide sequencing. The analyte may be a protein. In one aspect, a method of translocating a DNA at a low ionic strength is described herein. The method comprises (a) providing, in a low ionic strength solution, any one of the modified ClyA nanopores described herein and a membrane (e.g., an artificial membrane), wherein the modified ClyA nanopore is present in the membrane such that the cis opening of the modified ClyA nanopore is present in a cis side of the low ionic strength solution and the trans opening of the modified ClyA nanopore is present in a trans side of the low ionic strength solution; (b) providing a DNA in the cis side of the low ionic strength solution; and (c) applying an electrical potential across the modified ClyA nanopore so that the DNA is translocated through the modified ClyA nanopore from the cis side to the trans side. In one example, the low ionic strength solution may be a salt solution (e.g., a sodium chloride solution) having an ionic strength of about 150 mM to about 300 mM. Such a method may be used for characterizing a polynucleotide (e.g., DNA or RNA).

Accordingly, a method of characterizing a target polynucleotide is also provided herein. The method comprises (a) providing, in a low ionic strength solution (e.g., of about 150 mM to about 300 mM), any one of the modified ClyA nanopores described herein and a membrane, wherein the modified ClyA nanopore is present in the membrane; (b) adding in the low ionic strength solution of step (a) the target polynucleotide; and (c) measuring, during application of a potential across the nanopore, ion flow through the modified ClyA nanopore, wherein the ion flow measurements are indicative of one or more characteristics of the target polynucleotide. Non-limiting examples of the characteristics of the target polynucleotides that can be determined using the methods described herein include (i) the length of the target polynucleotide, (ii) the identity of the target polynucleotide, (iii) the sequence of the target polynucleotide, (iv) the secondary structure of the target polynucleotide, (v) whether or not the target polynucleotide is modified, and thereby characterizing the target polynucleotide, and any combinations thereof.

In any of the aspects described herein, the target polynucleotide can be a single-stranded DNA or a double-stranded DNA.

In any of the aspects described herein, the method can further comprise adding a polynucleotide binding protein in the low ionic strength solution such that the polynucleotide binding protein binds to the target polynucleotide and controls the movement of the target polynucleotide through the modified ClyA nanopore.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

The electrical recordings were carried out in 15 mM Tris-HCl. pH 7.5 at 22° C. Data were recorded by applying a 10-kHz low-pass Bessel filter and using a 20 µs (50 kHz) sampling rate. An additional 2-kHz low-pass Bessel filter was used for the data collected at 0.15 M NaCl solutions.

Figure 9:
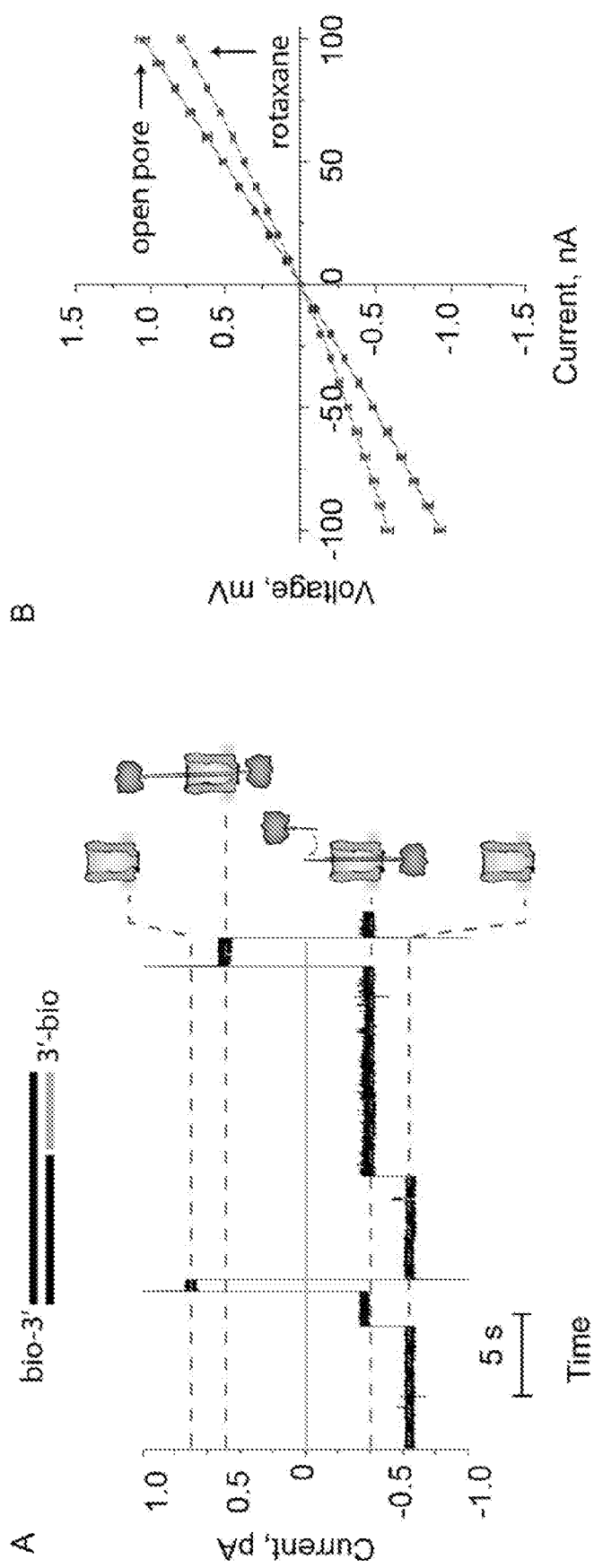

FIG. 9. Formation of a DNA rotaxane from the trans side at 1 M NaCl. Panel A) The dsDNA rotaxane was formed under −70 mV applied potential by adding a hybrid dsDNA/ssDNA thread T1d (1a and 1c, 1.0 µM, Table 3, shown as a black line above the current trace) complexed with neutravidin (1.2 uM, monomer) to the trans nanopore compartment. A 3'biotinylated ssDNA molecule, 1d (1.0 µM, Table 3, corresponding to the grey line above the current trace) complementary to the overhang of T1d was added to the cis compartment. Since the nanopore/DNA rotaxane can only formed if T1d translocates through the nanopore to hybridizes with 1, this experiments proves the translocation of DNA through ClyA from cis to trans. At −70 mV the blocked pore current of the threaded DNA was 64±2.0, average±S.D., N=3). After rotaxane formation, the reversal of the applied potential to +70 mV showed a blocked pore current ($I_{RES}$+70=73±0.5, average±S.D., N=3), indicating that dsDNA occupied the nanopore. Panel B) IV relationship for ClyA-RR and ClyA-RR in a rotaxane configuration.

Figure 10:
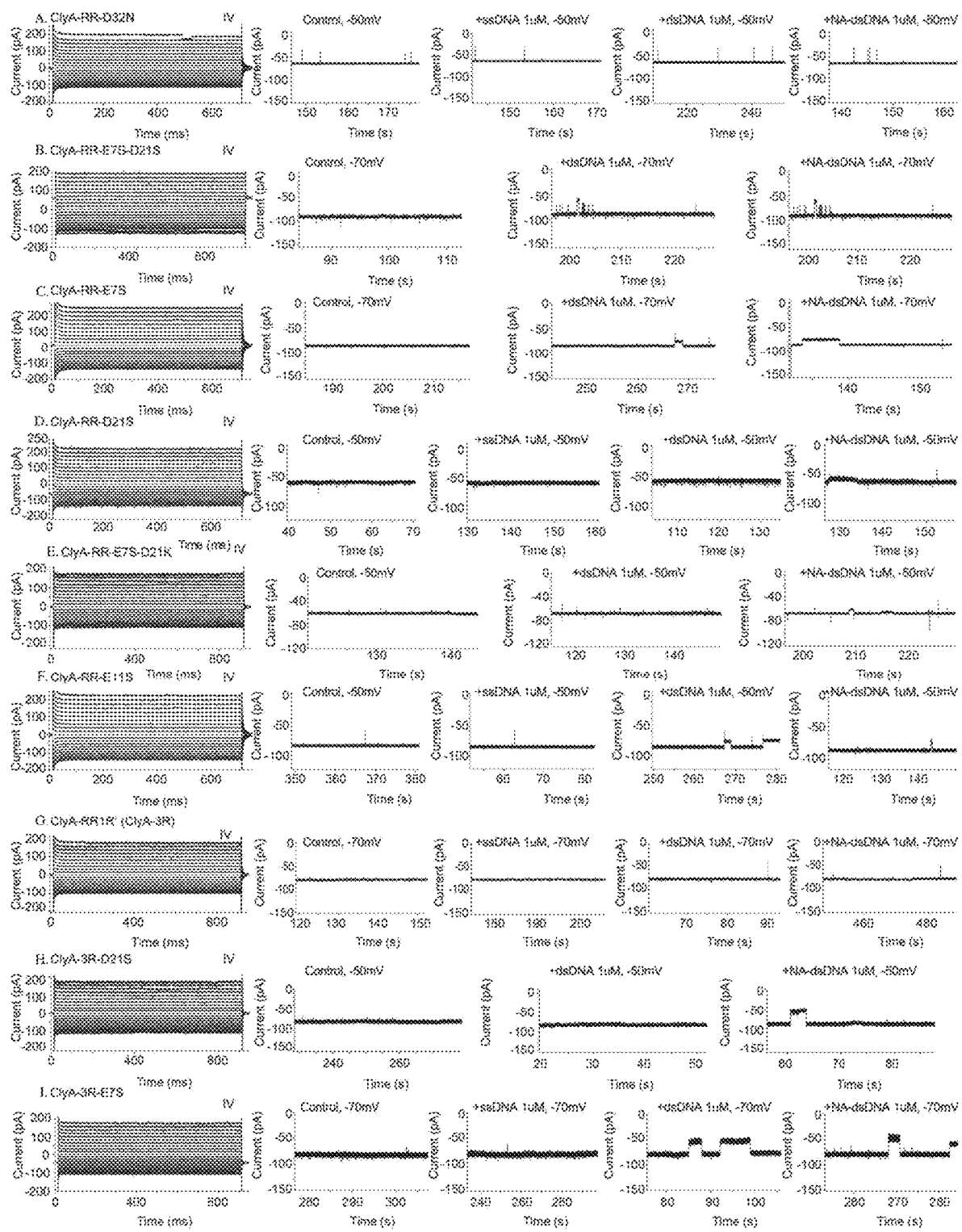

FIG. 10. Pore engineering for observing the translocation of DNA from the trans side in 0.15 M NaCl solutions. For each mutant indicated in Panels A-I, it is reported: the IV relationship (voltage ramp from +100 to −100 mV in 21 s and 10 mV voltage steps) and a representative current trace under positive VG applied potential before and after adding 1 µM of a biotinylated ssDNA (1a, Table 3) to the trans compartment. A variety of current traces are also shown after the subsequent addition of 1.2 µM neutravidin (monomer) and 1 µM of the complementary ssDNA (1b Table 1) to the trans solution. Although ClyA-3R-E7S showed current blockades following the addition of DNA to the trans chamber, a rotaxane could not be formed, suggesting the blockades are not due to the translocation of DNA. The electrical recordings were carried out in 0.15 M NaCl, 15 mM Tris-HCl. pH 7.5 at 22° C. Data were recorded by applying a 2-kHz low-pass Bessel filter and using a 100 µs (10 kHz) sampling rate.

Figure 11:
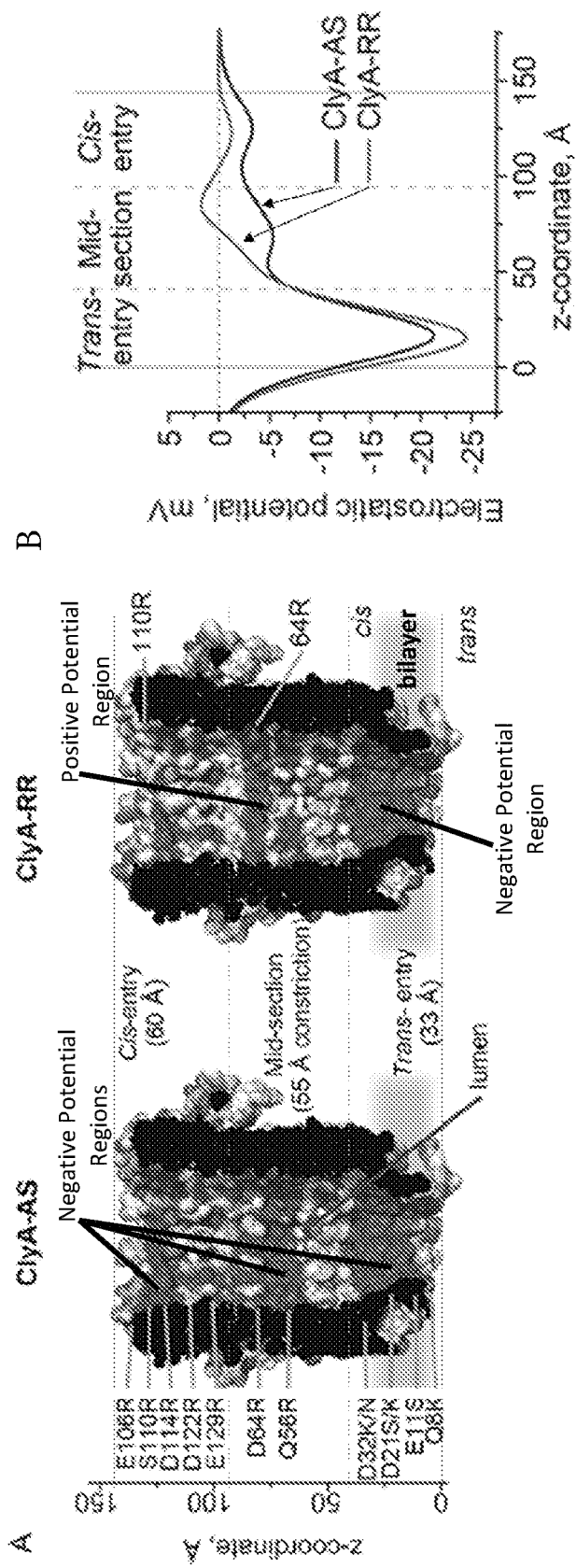

FIG. 11. Engineering the ClyA nanopore for DNA translocation. Panel A) Cross sections of the ClyA-AS (left) and ClyA-RR (right) nanopores imbedded into a lipid bilayer constructed by homology modeling from the *Escherichia coli* ClyA structure using VMD and NAMD (PDB: 2WCD, 90% sequence identity). The inner pore lumen is shown using the solvent-accessible surface area as calculated by PyMOL (version 1.8 Schrodinger, LLC) and shaded according to the electrostatic potential in a 150 mM NaCl solution as calculated by the adaptive Poisson-Boltzmann solver (APBS). Shaded regions correspond to negative and positive potentials (range −2 to +2 kBT/e or −51.4 to +51.4 mV). Panel B) Electrostatic potential at the center of ClyA-AS and ClyA-RR nanopores at 150 mM NaCl concentration.

Figure 12:
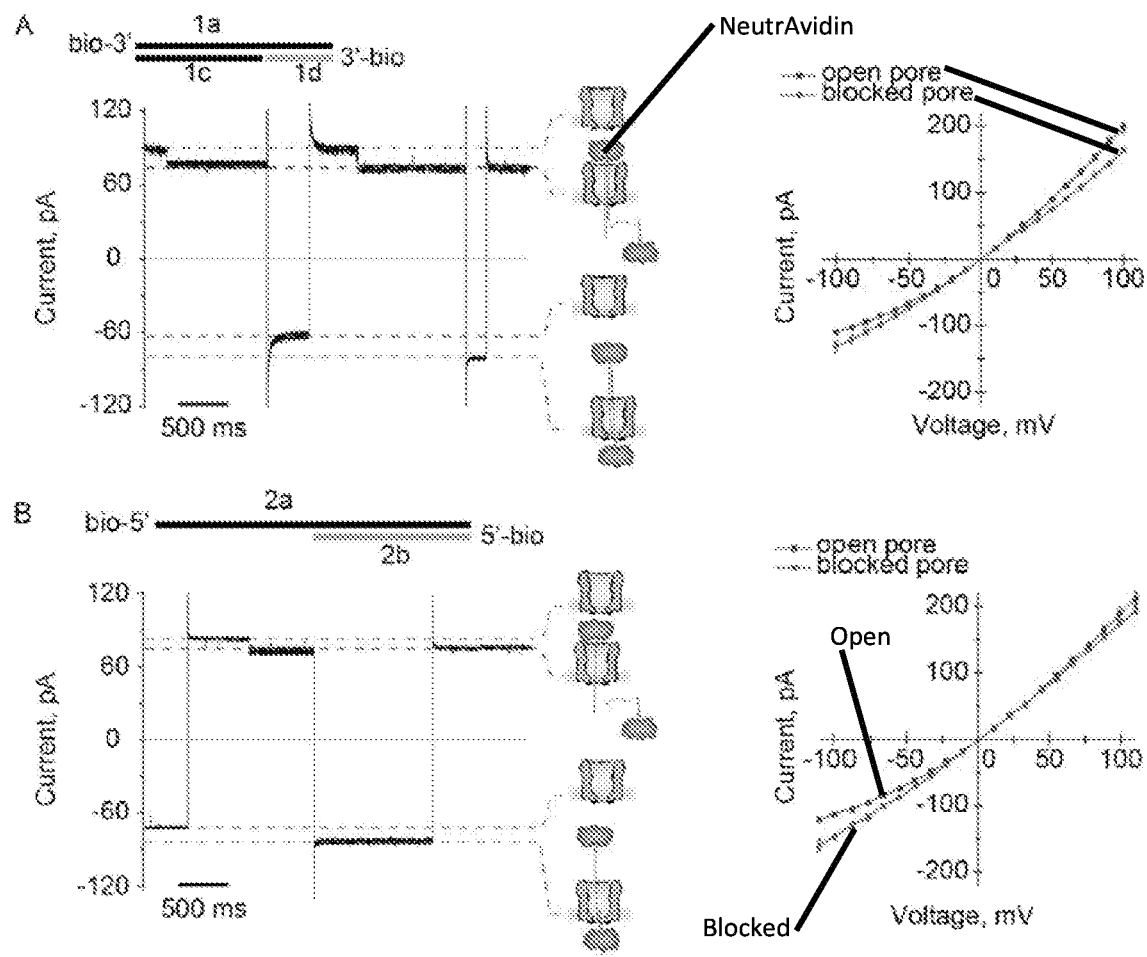

FIG. 12. DNA rotaxane formation in 150 mM NaCl solutions at +50 mV. Panel A) dsDNA rotaxane was formed by adding 1a/1c (1.0 µM, black lines) and 1d (1.0 µM, grey line) to the cis and trans compartments, respectively. Neutravidin (NA, 0.3 µM, tetramer) was also added in both solutions. Panel B) ssDNA/dsDNA hybrid rotaxane was formed by addition of a 5'-biotinylated ssDNA thread 2a (1.0 µLM, black line) to the cis compartment and a 5'-biotinylated ssDNA molecule complementary to the 3' end of 2a (2b, 1.0 µM, grey line) to the trans compartment. NA (0.3 µM, tetramer) was present on both sides. The graphs on the right-hand side of the current traces show the voltage relationship (I-V curve) for ClyA-RR and ClyA-RR in a rotaxane configuration. Experiments were carried out in a buffer containing 150 mM NaCl and 15 mM Tris-HCl (pH 7.5) at 22° C. The DNA sequences are shown in Table 3.

Figure 13:
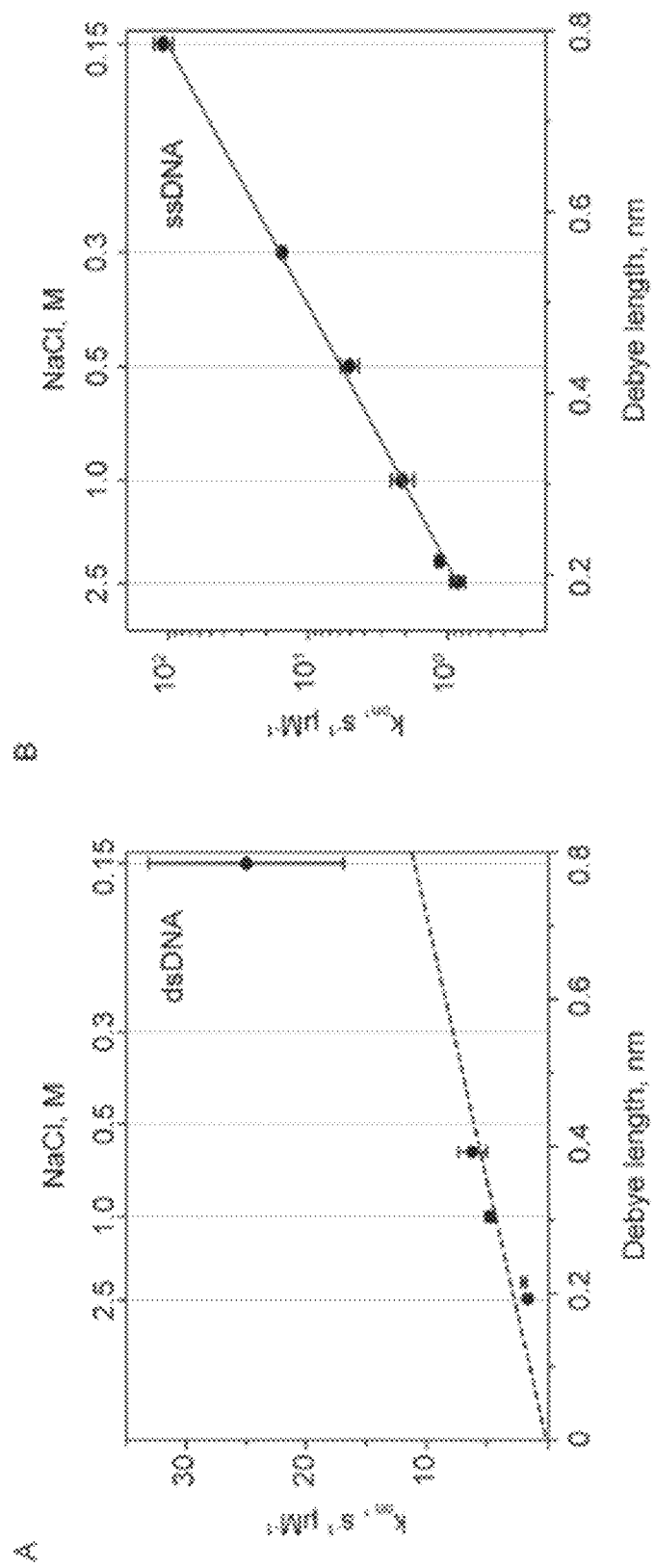

FIG. 13. Ionic strength dependence of DNA translocation and threading under +70 mV. Panels A-B) Debye length dependence of the frequency of dsDNA (Panel A) and ssDNA (Panel B) translocation per 1 µM DNA. The dotted line in (Panel A) depicts the theoretical prediction of translocation frequencies for a diffusion-limited process. The line in (Panel B) is an exponential regression indicating a barrier-limited process.

Figure 14:
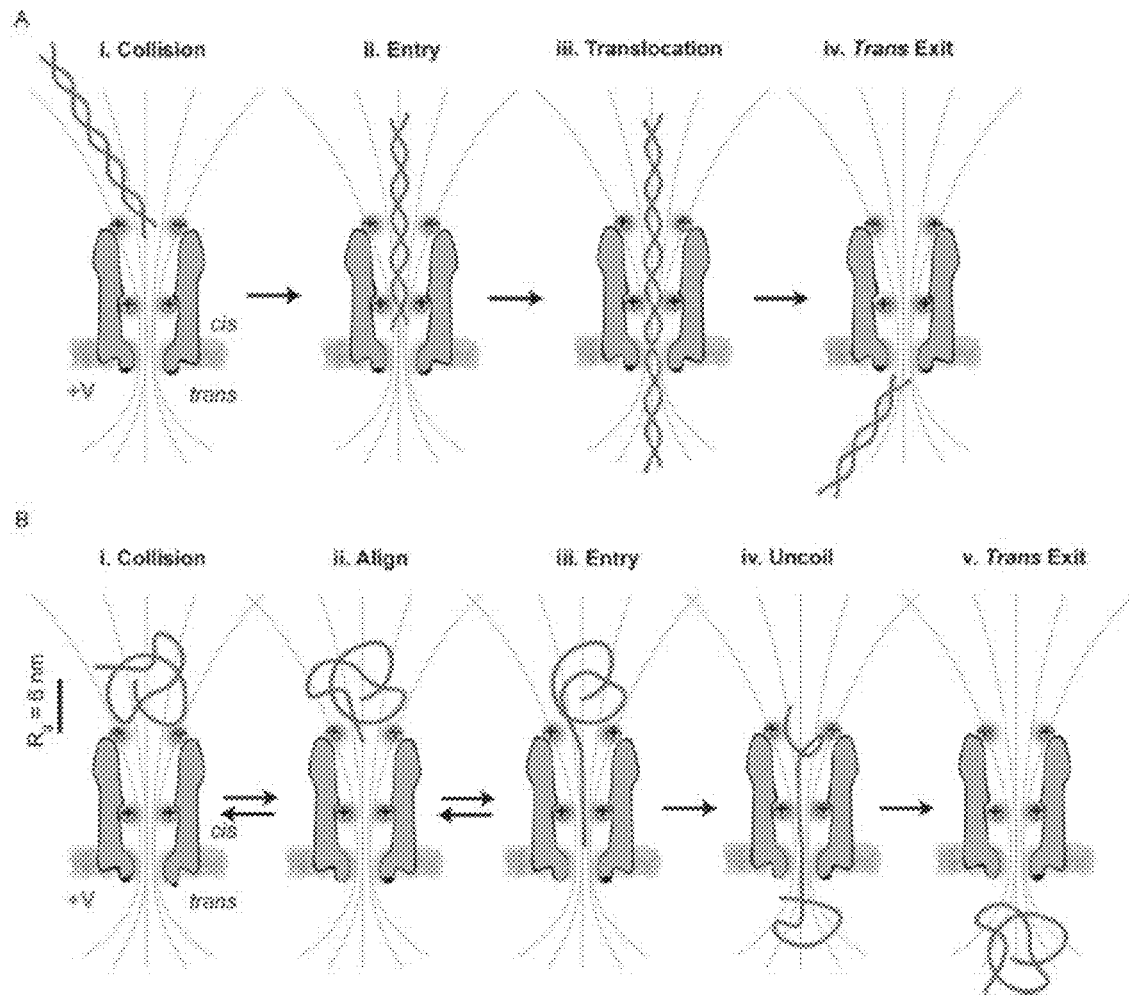

FIG. 14. Mechanism of dsDNA and ssDNA translocation through ClyA-RR nanopores. Panel A) dsDNA translocation is diffusion-limited. (i) dsDNA, which under the experimental conditions is a rigid rod, is aligned by the electric field lines and enters the nanopore with a defined orientation. (ii) dsDNA penetrates inside the nanopore, where it interacts with the second layer of engineered charges. (iii) dsDNA can then translocate the constriction and (iv) exit the pore. The charges at the cis entry of the nanopore aid in the initial capture. Panel B) ssDNA translocation is reaction-limited. (i) ssDNA has a coiled structure with a gyration radius ($R_g \approx 6$ nm), which is about twice the radius of the nanopore. (ii) ssDNA is not yet in the pore, and it searches for the entry. (iii) One end of ssDNA finds the entry of the cis lumen and starts to uncoil. Because there is an entropic energy barrier to enter the nanopore, several attempts can be made before a successful translocation event. (iv) In order to translocate the constriction, ssDNA needs to fully uncoil. (v) DNA exits the nanopore and then recoils. The additional charges at the cis entry most likely mediate the efficient capture of the DNA inside the nanopore. The DNA molecules and the nanopore are drawn to scale.

Figure 15:
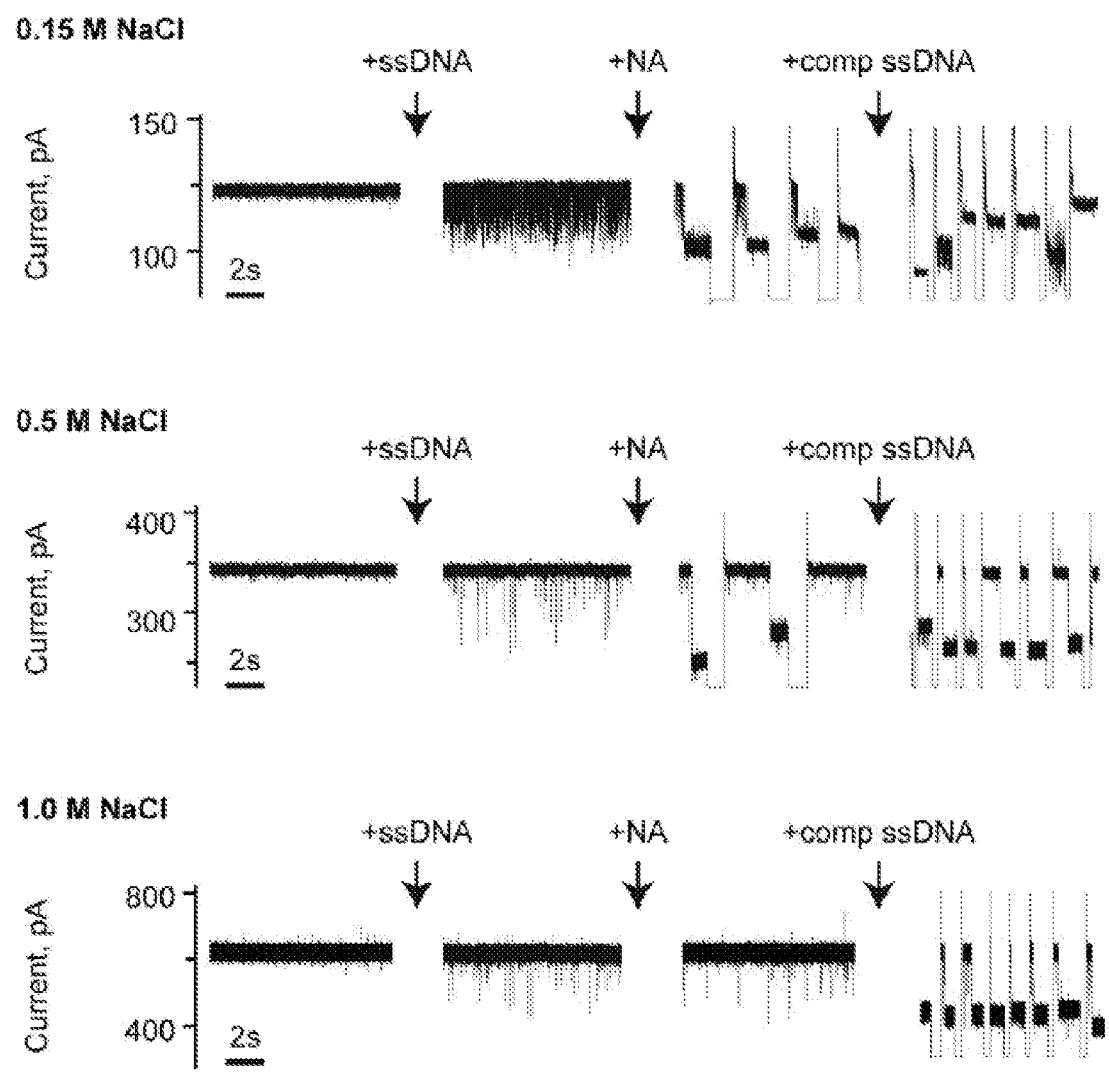

FIG. 15. Ionic strength dependency of DNA threading. ssDNA (1a, 1.0 µM) was first added to the cis side of ClyA-RR, then Neutravidin (NA, 0.3 µM, cis), and finally the complementary ssDNA (1b, 1 µM, cis). In 150 and 500 mM NaCl solutions the ssDNA:NA complex induced long-lasting current blockades, which are most likely due to the threading of ssDNA. In 1.0 M NaCl solution (or higher) the ssDNA:NA blockades were transient, suggesting that ssDNA could not fully thread the pore. The dsDNA:NA complex induced permanent blockades at all ionic strengths. Spikes above and below the open pore current level represent capacitive transients following the manual potential reversal used to free the nanopore from the DNA. The electrical recordings were carried out in 15 mM Tris-HCl, pH 7.5, at 22° C.

Figure 16:
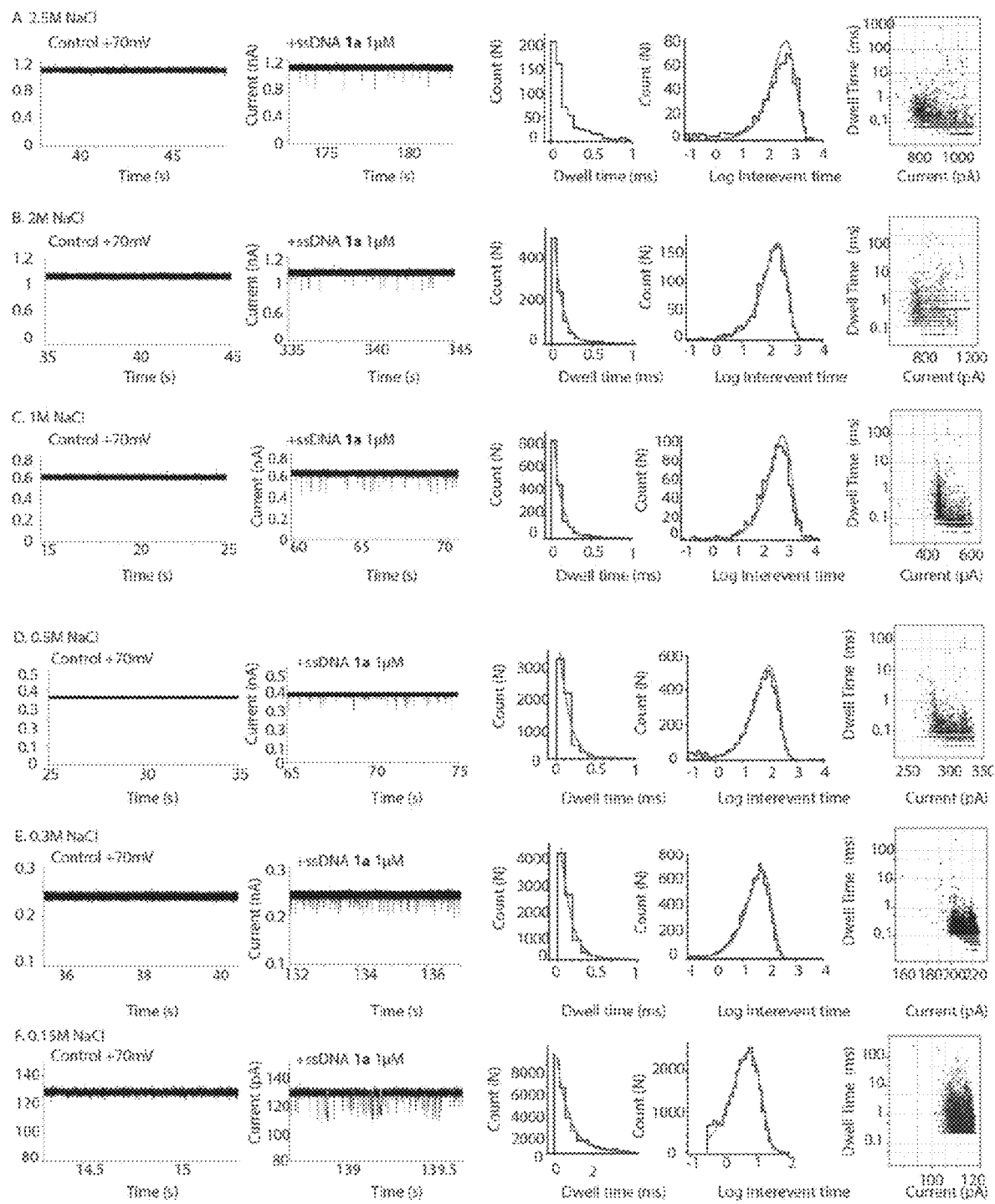

FIG. 16. Ionic strength dependency of ssDNA translocation through ClyA-RR nanopores. Panels A-F show data for different salt concentrations or ionic strengths. The current traces show the open pore current of ClyA-RR before and after adding 1.0 µM of a biotinylated ssDNA (1a, Table 3) to the cis side of the pore under +70 mV at different NaCl concentrations. The histograms on the right side of the traces represent dwell times (left histogram, conventional binning single exponential fit) and inter-event times (right histogram, logarithmic base 10, exponential logarithmic probability fit) of the dsDNA translocation events. The scattered plots represent currents versus dwell times. The electrical recordings were carried out in 15 mM Tris-HCl. pH 7.5 at 22° C. Data were recorded by applying a 10-kHz low-pass Bessel filter and using a 20 µs (50 kHz) sampling rate. An additional 2-kHz low-pass Bessel filter was used for the data collected at 0.15 M NaCl solutions.

Figure 17:
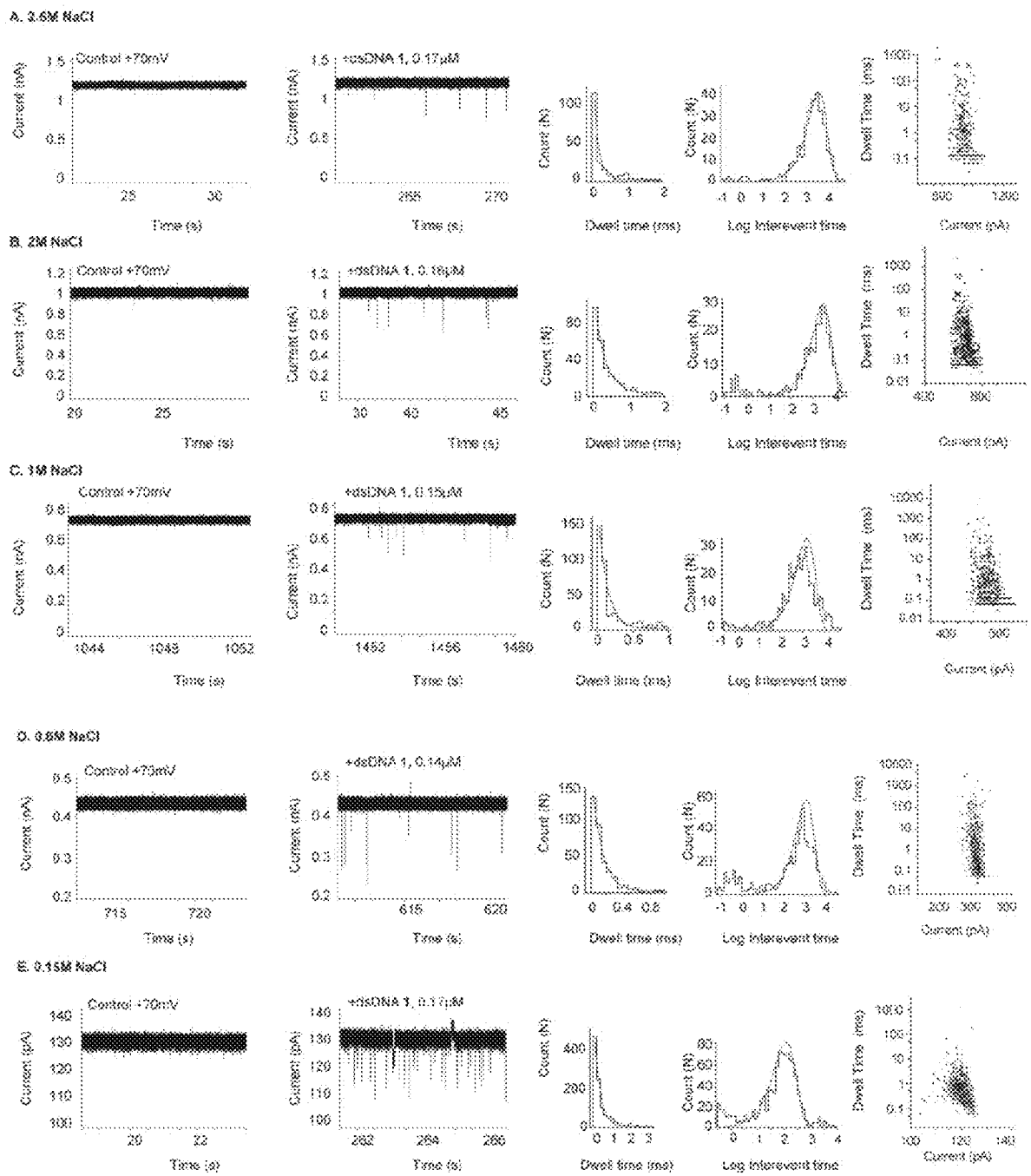

FIG. 17. Ionic strength dependency of dsDNA translocation through ClyA-RR nanopores. Panels A-E show data for different salt concentrations or ionic strengths. The current traces show the open pore current of ClyA-RR before and after adding 140-170 nM of a biotinylated dsDNA (1, Table 3) to the cis side of the pore under +70 mV at different NaCl concentrations. The histograms on the right side of the traces represent dwell times (left histogram, conventional binning single exponential fit) and inter-event times (right histogram, logarithmic base 10, exponential logarithmic probability fit) of the dsDNA translocation events. The scattered plot represents currents versus dwell times. The electrical recordings were carried out in 15 mM Tris-HCl pH 7.5 at 22° C. Data were recorded by applying a 10-kHz low-pass Bessel filter and using a 50 kHz sampling rate. An additional 2-kHz low-pass Bessel filter was used for the data collected at 0.15 M NaCl solutions.

Figure 18:
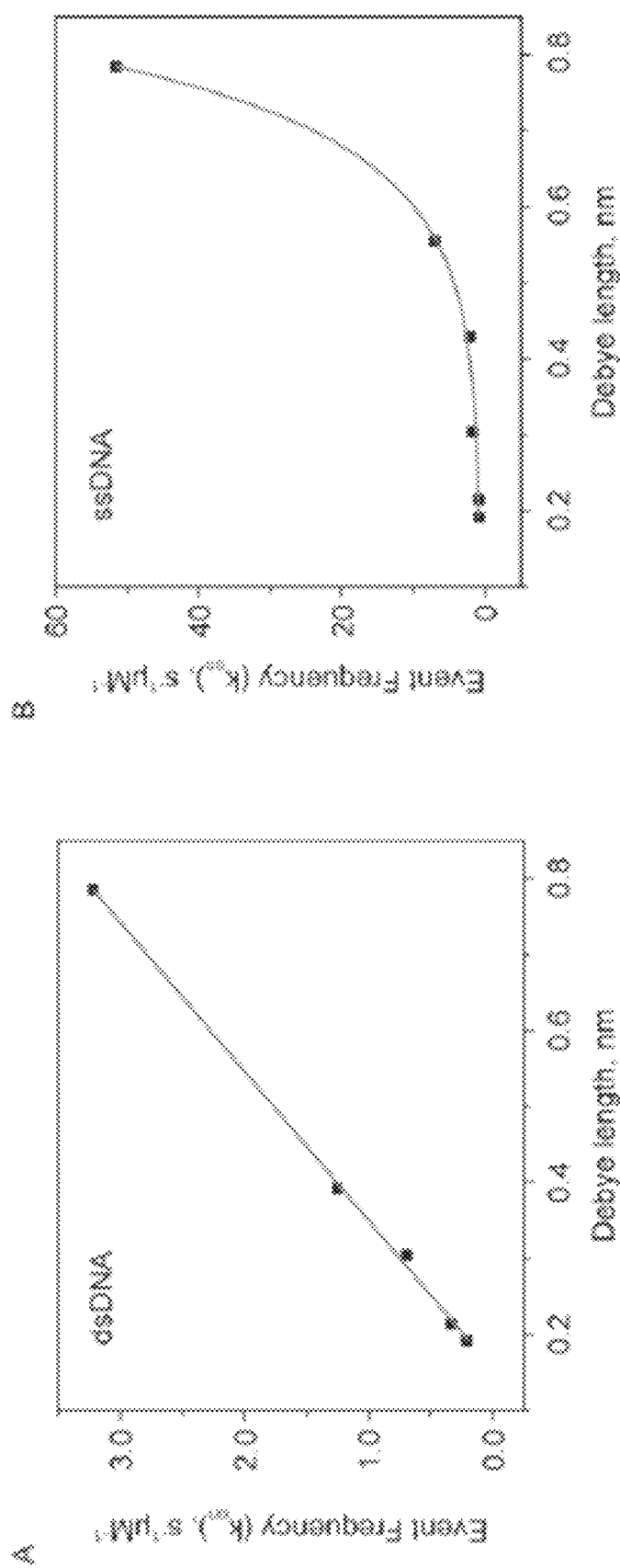

FIG. 18. Ionic strength dependency of the DNA translocation frequency filtered at 1 kHz. Salt dependency of the event frequencies for (Panel A) dsDNA and (Panel B) ssDNA as determined from current traces filtered using a 1 kHz digital Gaussian filter (Clampfit, Molecular Devices). The lines show linear (Panel A) and exponential (Panel B) regression fits.

Figure 19:
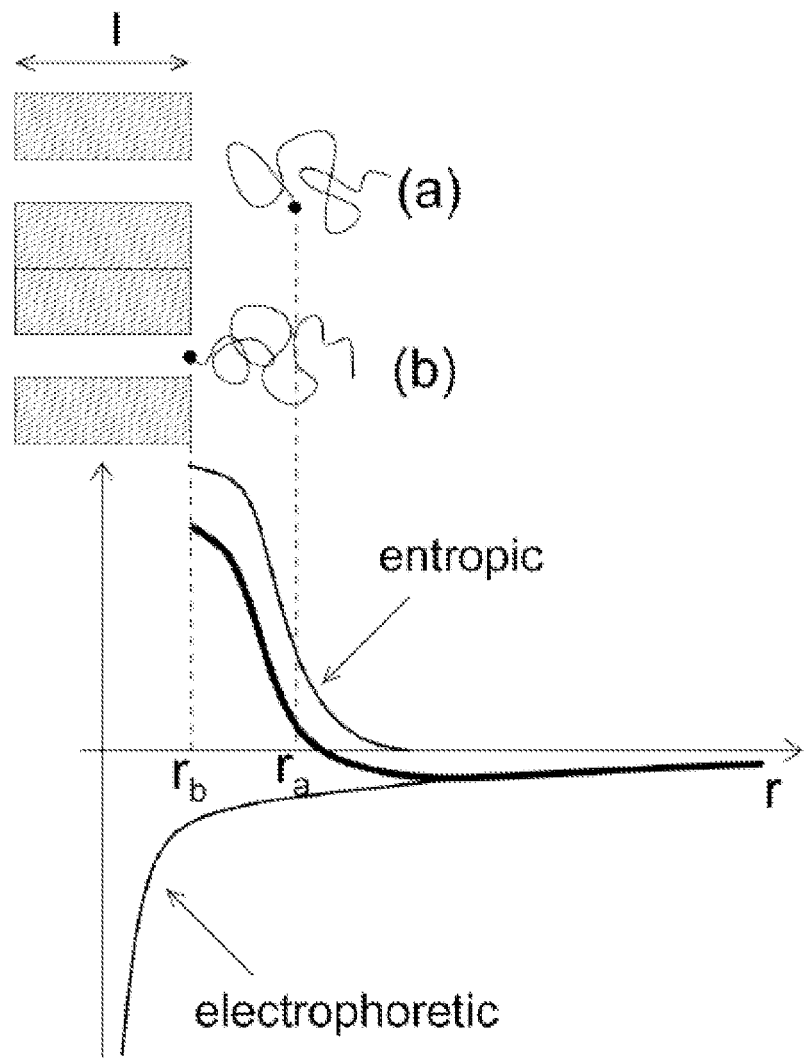

FIG. 19. Entropic and electrophoretic forces acting on ssDNA near a nanopore. ssDNA has a coiled shape and is expected to be captured by the pore via a barrier crossing (reaction-limited process). The barrier originates from a repulsive force of entropic origin in the vicinity of the pore which acts on top of the attractive electrophoretic force. The free energies for these two contributions are indicated with thin lines, while the thick line is the sum of the two (Eq. (15)). The top part of the figure shows two characteristic configurations of the ssDNA characterized by reaction coordinates ra and rb, respectively. The configuration (b) has a lower entropy and corresponds to a state close to the top of the barrier.

Figure 20:
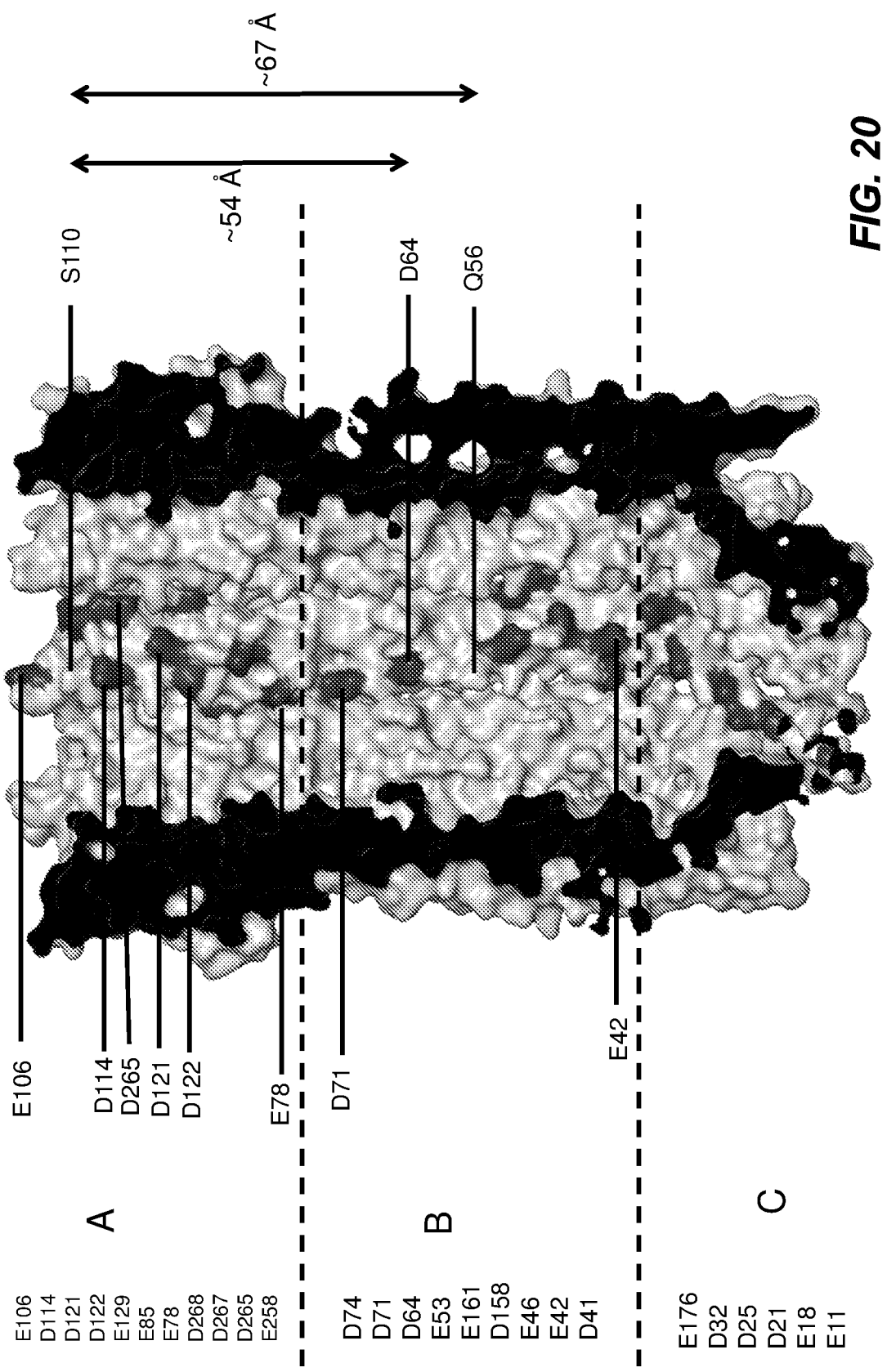

FIG. 20 shows the structure of ClyA and the cis section denoted as A, the mid-section, denoted as B and the trans section, denoted as C. The negatively charged amino-acids D and E are shown at the left hand side of the figure (along with the polar uncharged amino-acids S and Q). Substitution of one of more of the polar uncharged amino-acid or the negatively charged amino-acids can take place in A, substitution of one or more of the negatively charged amino-acids can take place in B. Region C which contains a number of negatively charged amino-acids can remain as it is, with no substitutions with neutral or positively charged amino-acids.

DETAILED DESCRIPTION OF THE INVENTION

While transmembrane pores (e.g., protein nanopores or solid state nanopores) are useful as sensors to detect or characterize a biopolymer, translocation of a biopolymer, e.g., a polynucleotide through certain nanopores at low ionic strengths (e.g., about 150 mM to about 300 mM) could be challenging. In particular, nanopores having a portion with a negative internal surface charge and radii comparable to the size of a negatively-charged biopolymer (e.g., ~2.2 nm for the B-form of dsDNA and ~1 nm for ssDNA) can create a large electrostatic barrier for the entry of the negative-charged biopolymer into the nanopore at low ionic strengths. Accordingly, there is a need to engineer transmembrane nanopores that permit more efficient capture and/or translocation of a negatively-charged biopolymer, e.g., a polynucleotide, across the nanopores, which can be useful for practical applications such as polynucleotide mapping or sequencing.

The present disclosure is based, at least in part, on the unexpected discovery that positive charges can be introduced into the luminal surface of a transmembrane nanopore, for example, a cytolysin A (ClyA), at certain positions to overcome the entropic and electrostatic barriers for DNA translocation through the negatively charged narrow constriction (e.g., with a dimension of about 3.3 nm). For example, it was discovered that introduction of positive changes (e.g., positively-charged amino acids such as arginines) at the wider entry (the cis side) and midsection of the ClyA nanopore are sufficient to "grab" and orient the DNA (e.g., double stranded or single stranded) for effective electrophoretic-driven sliding through the narrow and negatively charged trans constriction, even in the absence of any modifications to the negatively charged trans constriction itself. Further, it was discovered that such modifications permit DNA translocation at low ionic strengths, e.g., as low as 50 mM. In principle the modifications allow the methods of any aspects described herein to be carried out at even lower ionic strengths than 50 mM. However lower ionic strengths may give rise to correspondingly lower ionic currents and therefore, in some circumstances, may not be desirable. Without such modifications, translocation of single-stranded or double-stranded DNA through the nanopore was only observed above 2.0 M ionic strength.

Accordingly, in some aspects, the present disclosure provides modified ClyA nanopore subunit polypeptide (e.g., for forming a modified ClyA nanopore) and nanopores comprising the same. The modified ClyA nanopores as described herein can be used for various practical applications such as characterizing a polynucleotide. Accordingly, described herein are also methods and compositions for characterizing a polynucleotide such as a double stranded or single stranded polynucleotide. The methods and compositions described herein provide efficient translocation of doubled stranded or single stranded polynucleotide at physiological ionic strengths (e.g., 50 mM-300 mM) or low ionic strengths (e.g., less than 2 M or less than 1 M).

The modified ClyA nanopores and methods described herein permit unidirectional translocation of a polynucleotide, namely the polynucleotide is unable to enter and transit the nanopore in the trans to cis direction. This enables for example the filtering of polynucleotide (e.g., DNA) in the cis to trans direction.

It is also contemplated that other nanostructures having a similar nanopore structure as that of the ClyA nanopore (e.g., a cylindrical lumen with a larger diameter (e.g., 5-7 nm) at the cis opening and a negatively charged narrower constriction (e.g., 3-4 nm in diameter) at the trans opening can adopt similar modification strategy to allow DNA translocation in low ionic strength solutions.

Modified ClyA Nanopore Subunit Polypeptides

One aspect of the present disclosure provides modified ClyA nanopore subunit polypeptides. A modified ClyA nanopore subunit polypeptide is a polypeptide whose sequence varies from that of a reference ClyA amino acid sequence. The amino acid sequence of the modified ClyA nanopore subunit polypeptide comprises (i) a cis opening-forming amino acid sequence, (ii) a midsection-forming amino acid sequence, and (iii) a trans opening-forming amino acid sequence. The cis opening-forming amino acid sequence is a portion of the amino acid sequence that forms part of a cis opening of a nanopore when the modified ClyA nanopore subunit polypeptide interacts with other subunit polypeptides to form the nanopore in a membrane. The midsection-forming amino acid sequence is a portion of the amino acid sequence that forms part of a mid-section of the nanopore when the modified ClyA nanopore subunit polypeptides interacts with other subunit polypeptides to form the nanopore in a membrane. The trans opening-forming amino acid sequence is a portion of the amino acid sequence that forms part of a trans opening of a nanopore when the modified ClyA nanopore subunit polypeptide interacts with other subunit polypeptides to form the nanopore in a membrane. Methods to identify portions of the ClyA amino acid sequence that correspond to the cis portion, mid-section, and trans portion of a ClyA nanopore are known in the art and also described in the Examples. For example, a nanopore, a portion of which is embedded into a membrane can be constructed by homology modeling from a known ClyA structure using VMD, e.g., as described in Humphrey et al., "VMD: Visual Molecular Dynamics" J. Mol. Graphics (1996) 14: 33-38; and NAMD, e.g., as described in Phillips et al., "Scalable Molecular Dynamics with NAMD" J. Comput. Chem. (2005) 26: 1781-1802. See, e.g., FIG. 1A.

As used herein, the term "reference ClyA amino acid sequence" refers to a known amino acid sequence of a ClyA nanopore subunit. Various forms of ClyA nanopore subunits are known in the art, including, e.g., but not limited to ClyA wild-type (ClyA-WT), ClyA-SS, ClyA-CS, and ClyA-AS. See, e.g., Soskine et al. "Tuning the size and properties of ClyA nanopores assisted by directed evolution" J Am Chem Soc. (2013) 135: 13456-13463, which describes different mutations in ClyA-SS, ClyA-CS, and ClyA-AS, relative to ClyA-WT, and methods of making them. Any ClyA amino acid sequences described in WO 2016/166232 and WO 2014/153625 can also be used as a reference ClyA amino acid sequence. In one embodiment, the reference ClyA amino acid sequence is an amino acid sequence of ClyA-WT as set forth in SEQ ID NO: 1. In one embodiment, the reference amino acid is an amino acid sequence of ClyA-AS as set forth in SEQ ID NO: 2, which contains the following mutations: C87A, L99Q, E103G, F166Y, I203V, C285S, K294R, as compared to the amino acid sequence of ClyA-WT as set forth in SEQ ID NO: 1. In some embodiments, the amino acid sequence of ClyA-AS can further include H307Y, as compared to the amino acid sequence of ClyA-WT.

In some embodiments, the modified ClyA nanopore subunit polypeptide comprises an amino acid sequence that is at least about 80% (including, e.g., at least about 85%, at least about 90%, at least about 95%, at least about 96%, at least about 97%, at least about 98%, at least about 99% or higher) identical to a reference ClyA amino acid sequence. Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S.F et al (1990) J Mol Biol 215:403-10. Software for performing BLAST analyses is publicly available through the National Center for Biotechnology Information (http://www.ncbi.nlm.nih.gov/).

The amino acid sequence of the modified ClyA nanopore subunit polypeptide comprises (i) a first positive charge modification (e.g., a first positively-charged amino acid substitution) at a position within the cis opening-forming amino acid sequence; and (ii) a second positive charge modification (e.g., a second positively-charged amino acid substitution) at a position within the midsection-forming amino acid sequence. The first and second positive charge modifications (e.g., the first and second positively-charged substitutions) are selected to provide higher frequency of capture and/or translocation of a negatively-charged polymer (e.g., a polynucleotide such as double stranded or single stranded DNA) through the nanopore, as compared to a reference ClyA amino acid sequence.

In one embodiment, the first positive charge modification (e.g., the first positively-charged amino acid substitution) may be at position 110 of the amino acid sequence as set forth in SEQ ID NO: 1 or SEQ ID NO: 2. In some embodiments, substitution with a positive charge (e.g., a positively-charged amino acid) may take place at one of more of the following positions: E106, D114, D121, D122, E129, E85, E78, D268, D267, D265, E258 of SEQ ID NO: 1 or SEQ ID NO: 2. In some embodiments, a ClyA amino acid sequence (e.g., as set forth in SEQ ID NO 1 or 2) may be modified or engineered to include additional amino acids "MI" at its N-terminus.

In one embodiment, the second positive charge modification (e.g., the second positively-charged amino acid substitution) may be at position 64 of the amino acid sequence as set forth in SEQ ID NO: 1 or SEQ ID NO: 2. In some embodiments, substitution with a positive charge (e.g., a positively-charged amino acid) may take place at one of more of the following positions: D74, D71, D64, E53, E161, D158, E46, E42, D41 of SEQ NO: 1 or SEQ ID NO: 2.

The term "positively-charged amino acid substitution" as used herein refers to a modification to a reference amino acid that increases the net positive charge, or decreases the net negative charge, of the reference amino acid, e.g., as detected at pH 7.0-8.0 (e.g., at pH 8.0) and at room temperature, e.g., at 20-25° C. For example, a positively-charged amino acid substitution can include, but is not limited to, (i) replacement of a negatively-charged amino acid with a less negatively charged amino acid, neutral amino acid, or positively-charged amino acid, (ii) replacement of a neutral amino acid with a positively-charged amino acid, or (iii) replacement of a positively charged amino acid with a more positively-charged amino acid. In some embodiments, a positively-charged amino acid substitution may include deletion of a negatively-charged amino acid or addition of a positively-charged amino acid. In some embodiments, a positively-charged amino acid substitution may include one or more chemical modifications of one or more negatively charged amino acids which neutralize their negative charge. For instance, the one or more negatively charged amino acids may be reacted with a carbodiimide.

A positively-charged amino acid is an amino acid having an isoelectric point (pI) that is higher than the pH of a solution so that the amino acid in the solution carries a net positive charge. For example, examples of a positively-charged amino acid as detected at pH 7.0-8.0 (e.g., at pH 8.0) and at room temperature, e.g., at 20-25° C., include, but are not limited to arginine (R), histidine (H), and lysine (K). A negatively-charged amino acid is an amino acid having a pI that is lower than the pH of a solution so that the amino acid in the solution carries a net negative charge. Examples of a negatively-charged amino acid as detected at pH 7.0-8.0 (e.g., at pH 8.0) and at room temperature, e.g., at 20-25° C., include, but are not limited to aspartic acid (D), glutamic acid (E), serine (S), glutamine (Q). A neutral amino acid is an amino acid having an isoelectric point (pI) that is same as the pH of a solution so that the amino acid in the solution carries no net charge. The pI values of amino acids are known in the art. By comparing the pI value of an amino acid of interest to the pH of a solution, one of ordinary skill in the art will readily determine whether the amino acid present in the solution is a positively charged amino acid, a neutral amino acid, or a negatively-charged amino acid. As used herein, the term "amino acid" can be an naturally-occurring or synthetic amino acid.

In some embodiments, the first and/or second positively-charged amino acid substitutions, e.g., as detected at pH 7.0-8.0 (e.g., at pH 8.0) and at room temperature, e.g., at 20-25° C., include, but are not limited to substitution of a reference amino acid with one of an arginine, a histidine, and a lysine.

In some embodiments, the first positively-charged amino acid substitution is S110R, wherein position 110 corresponds to amino acid 110 of SEQ ID NO: 1 or SEQ ID NO: 2.

In some embodiments, the second positively-charged amino acid substitution is D64R, wherein position 64 corresponds to amino acid 64 of SEQ ID NO: 1 or SEQ ID NO: 2.

In addition to the first and second positively-charged amino acid substitutions described herein, amino acid substitutions may be made to a reference ClyA amino acid sequence, for example up to 1, 2, 3, 4, 5, 6, 7, 8, 9, 10, 15, 20, or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

Conservative amino acid changes are well-known in the art and may be selected in accordance with the properties of the 20 main amino acids as defined in Table A below. Where amino acids have similar polarity, this can also be determined by reference to the hydropathy scale for amino acid side chains in Table A.

TABLE A

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE B

| Hydropathy scale | |
|---|---|
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |

TABLE B-continued

Hydropathy scale

| Side Chain | Hydropathy |
|---|---|
| Asp | −3.5 |
| Asn | −3.5 |
| Lys | −3.9 |
| Arg | −4.5 |

One or more amino acid residues of the amino acid sequence of SEQ ID NO: 1 or 2 may additionally be deleted from the polypeptides described above. Up to 1, 2, 3, 4, 5, 10, 20 or 30 residues may be deleted, or more.

One or more amino acids may be alternatively or additionally added to the polypeptides described above. An extension may be provided at the amino terminal or carboxy terminal of the amino acid sequence of SEQ ID NO: 1 or 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence, e.g., an amino acid sequence of a modified ClyA nanopore subunit polypeptide. Other fusion proteins are discussed in more detail below.

Methods for modifying amino acids (e.g., by substitution, addition, or deletion) are well known in the art. For instance, a reference amino acid may be substituted with a target amino acid by replacing the codon for the reference amino acid with a codon for the target amino acid at the relevant position in a polynucleotide encoding the modified ClyA nanopore subunit polypeptide. The polynucleotide can then be expressed as discussed below. If the amino acid is a non-naturally-occurring amino acid, it may be introduced by including synthetic aminoacyl-tRNAs in the IVTT system used to express the modified ClyA nanopore subunit polypeptide. Alternatively, it may be introduced by expressing the modified ClyA nanopore subunit polypeptide in E. coli that are auxotrophic for specific amino acids in the presence of synthetic (i.e., non-naturally-occurring) analogues of those specific amino acids. They may also be produced by naked ligation if the modified ClyA nanopore subunit polypeptide is produced using partial peptide synthesis.

In some embodiments, the trans opening-forming amino acid sequence of the modified ClyA nanopore subunit polypeptide may carry a net negative charge, e.g., as detected at pH 7.0-8.0 (e.g., at pH 8.0) and room temperature (e.g., at 20-25° C.), which is comparable to (e.g., within 10%, within 5%, within 4%, within 3%, within 2%, within 1%, or lower) the net negative charge of the corresponding trans opening-forming portion of a reference ClyA amino acid sequence. For example, in some embodiments, the trans opening forming amino acid sequence of the modified ClyA nanopore subunit polypeptide can be at least about 95% or higher (including, e.g., at least about 96%, at least about 97%, at least about 98%, at least about 99% or up to 100%) identical to the corresponding trans opening-forming portion of a reference ClyA amino acid sequence, e.g., as set forth in SEQ ID NO: 1 or SEQ ID NO: 2. In one embodiment, the trans opening-forming amino acid sequence of the modified ClyA nanopore subunit polypeptide is 100% identical to the corresponding trans opening-forming portion of the amino acid sequence as set forth in SEQ ID NO: 2.

The modified ClyA nanopore subunit polypeptides described herein may be used to form a homo-multimeric nanopore or hetero-multimeric nanopore as described herein. Accordingly, in some embodiments, the modified ClyA nanopore subunit polypeptide retains the ability to form a nanopore with other subunit polypeptides. Methods for assessing the ability of modified monomers to form nanopores are well-known in the art. For instance, a modified ClyA nanopore subunit polypeptide may be inserted into an amphiphilic layer along with other appropriate subunits and its ability to oligomerize to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

The modified ClyA nanopore subunit polypeptides may contain non-specific modifications as long as they do not interfere with nanopore formation. A number of non-specific side chain modifications are known in the art and may be made to the side chains of the amino acids. Such modifications include, for example, reductive alkylation of amino acids by reaction with an aldehyde followed by reduction with NaBH4, amidination with methylacetimidate or acylation with acetic anhydride.

The modified ClyA nanopore subunit polypeptides can be produced using standard methods known in the art. The modified ClyA nanopore subunit polypeptides may be made synthetically or by recombinant means. For example, the modified ClyA nanopore subunit polypeptides may be synthesized by in vitro translation and transcription (IVTT). Suitable methods for producing pores and modified ClyA nanopore subunit polypeptides are discussed in International Application Nos. PCT/GB09/001690 (published as WO 2010/004273), PCT/GB09/001679 (published as WO 2010/004265) or PCT/GB10/000133 (published as WO 2010/086603).

The modified ClyA nanopore subunit polypeptides as described herein may be produced using D-amino acids. For instance, the modified ClyA nanopore subunit polypeptides as described herein may comprise a mixture of L-amino acids and D-amino acids. This is conventional in the art for producing such proteins or peptides.

In some embodiments, the modified ClyA nanopore subunit polypeptides may be chemically modified. The modified ClyA nanopore subunit polypeptides can be chemically modified in any way and at any site. For instance, the modified ClyA nanopore subunit polypeptides may be chemically modified by attachment of a dye or a fluorophore. In some embodiments, the modified ClyA nanopore subunit polypeptide may be chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art.

In some embodiments, the modified ClyA nanopore subunit polypeptide may be chemically modified with a molecular adaptor that facilitates the interaction between a nanopore comprising the modified ClyA nanopore subunit polypeptide and a target nucleotide or target polynucleotide sequence. The presence of the adaptor improves the host-guest chemistry of the nanopore and the nucleotide or polynucleotide sequence and thereby improves the sequencing ability of pores formed from the modified ClyA nanopore subunit polypeptides. The principles of host-guest chemistry are well-known in the art. The adaptor has an effect on the physical or chemical properties of the nanopore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore.

In some embodiments, the molecular adaptor may be a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

In some embodiments, the molecular adaptor can be covalently attached to the modified ClyA nanopore subunit polypeptide. The adaptor can be covalently attached to the nanopore using any method known in the art. The adaptor is typically attached via chemical linkage. If the molecular adaptor is attached via cysteine linkage, one or more cysteines can be introduced to the modified ClyA nanopore subunit polypeptide by substitution.

In other embodiment, the modified ClyA nanopore subunit polypeptide may be attached or coupled to a polynucleotide binding protein, e.g., helicases, exonucleases, and polymerases. In some embodiments, the modified ClyA nanopore subunit polypeptide may be attached or coupled to a helicase, e.g., a DNA helicase. Examples of helicases, exonucleases, and polymerases that are suitable for use in nanopore sequencing are known in the art. In some embodiments, the modified ClyA nanopore subunit polypeptide may be attached or coupled to a helicase, e.g., a DNA helicase, a He1308 helicase (e.g., as described in WO 2013/057495), a RecD helicase (e.g., as described in WO2013/098562), a XPD helicase (e.g., as described in WO201/098561), or a Dda helicase (e.g., as described in WO2015/055981). This forms a modular sequencing system that may be used in the methods of characterizing a target polynucleotide. Polynucleotide binding proteins are discussed below. The translocation speed control may be determined by the type of polynucleotide binding protein and/or amount of fuel (ATP) added to the system. For example, the rate of translocation of the double stranded DNA analyte may be controlled by a double stranded DNA translocase such as FtsK. Depending upon the fuel (ATP) added to the system, the translocation speed of a target polynucleotide can be between about 30 B/s and 1000 B/s.

In some embodiments, the polynucleotide binding protein can be covalently attached to the modified ClyA nanopore subunit polypeptide. The polynucleotide binding protein can be covalently attached to the modified ClyA nanopore subunit polypeptide using any method known in the art. The modified ClyA nanopore subunit polypeptide and the polynucleotide binding protein may be chemically fused or genetically fused. The modified ClyA nanopore subunit polypeptide and the polynucleotide binding protein are genetically fused if the whole construct is expressed from a single polynucleotide sequence. Genetic fusion of a modified ClyA nanopore subunit polypeptide to a polynucleotide binding protein is discussed in International Application No. PCT/GB09/001679 (published as WO 2010/004265).

The modified ClyA nanopore subunit polypeptide may be chemically modified with a molecular adaptor and a polynucleotide binding protein.

Any of the proteins described herein, such as the modified ClyA nanopore subunit polypeptides and nanopores described herein, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the modified ClyA nanopore subunit polypeptide and nanopores described herein, may be labelled with a detectable label. The detectable label may be any suitable label which allows the protein to be detected. Suitable labels include, but are not limited to, fluorescent molecules, radioisotopes, e.g., 125I, 35S, enzymes, antibodies, antigens, polynucleotides and ligands such as biotin.

Any of the proteins described herein, including the modified ClyA nanopore subunit polypeptide described herein, can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Polynucleotides Encoding the Modified ClyA Nanopore Subunit Polypeptides

Provided herein are also polynucleotide sequences encoding any one of the modified ClyA nanopore subunit polypeptides as described herein.

Polynucleotide sequences may be derived and replicated using standard methods in the art. Chromosomal DNA encoding wild-type ClyA may be extracted from a pore producing organism, such as *Salmonella typhi*. The gene encoding the pore subunit may be amplified using PCR involving specific primers. The amplified sequence may then undergo site-directed mutagenesis. Suitable methods of site-directed mutagenesis are known in the art and include, for example, combine chain reaction. Polynucleotides encoding any one of the modified ClyA nanopore subunit polypeptides can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art.

Another aspect of the disclosure includes a method of producing a modified ClyA nanopore subunit polypeptide or a construct described herein. The method comprises expressing a polynucleotide encoding any embodiment of the modified ClyA nanopore subunit polypeptides in a suitable host cell. The polynucleotide is preferably part of a vector and is preferably operably linked to a promoter.

Modified ClyA nanopores

One aspect of the present disclosure features a modified ClyA nanopore, for example, that permits capture of a negatively-charged polymer (e.g., polynucleotide such as DNA or RNA) into the modified ClyA nanopore and/or translocation of the negatively-charged polymer through the modified ClyA nanopore. The modified ClyA nanopore comprises a first opening, a mid-section, a second opening, and a lumen extending from the first opening through the mid-section to the second opening, wherein a luminal surface of the first opening comprises a first positively-charged amino acid substitution and a luminal surface of the mid-section comprises a second positively charged amino acid substitution. The luminal surface of the second opening defines an electronegative constriction. The first positive-charged amino acid substitution and the second charged amino acid substation are described in detail in the section "Modified ClyA nanopore subunit polypeptide" above.

Figure 1:
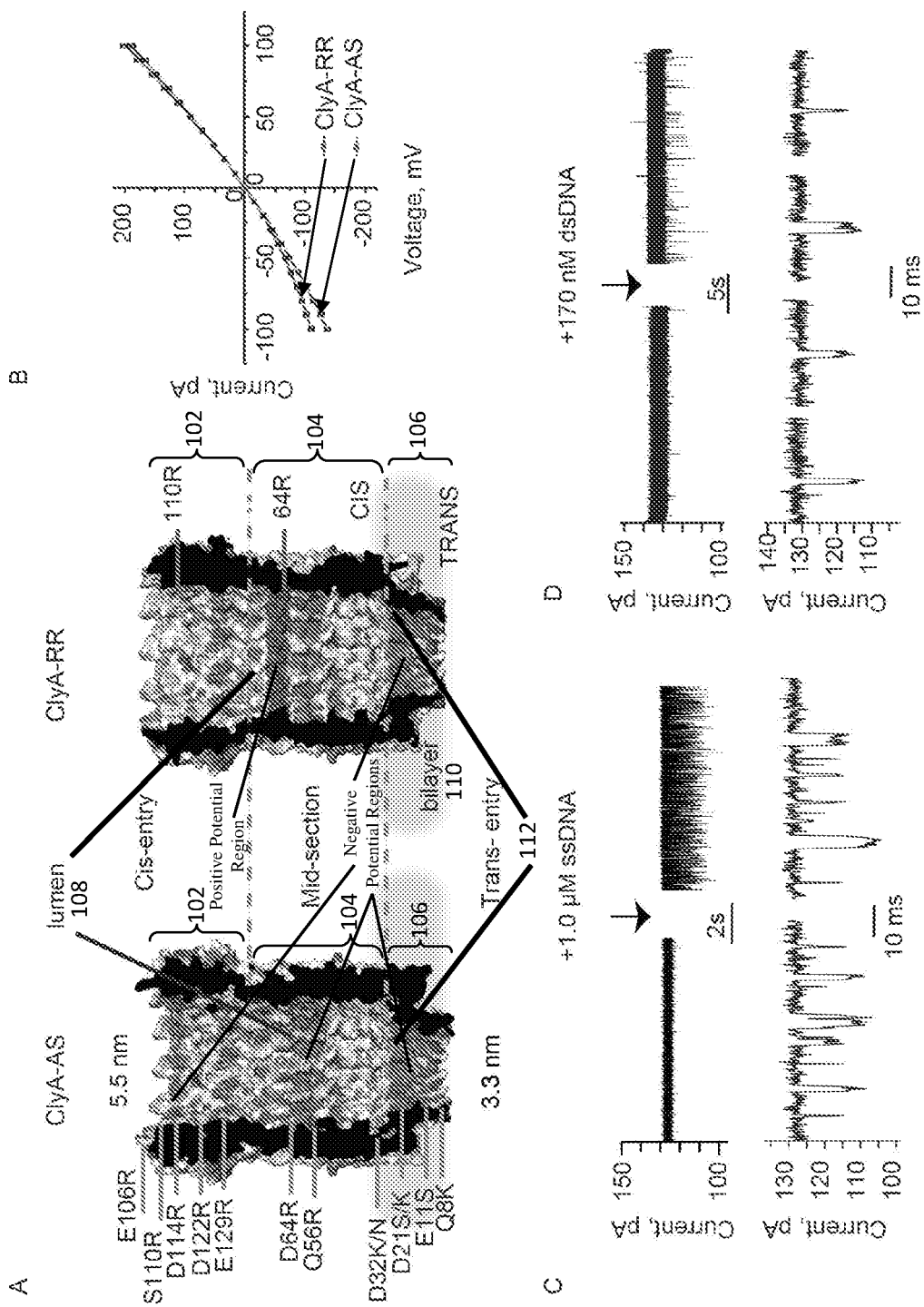
FIG. 1. Engineering ClyA nanopore for DNA translocation. Panel A) Cross section for ClyA-AS and ClyA-RR nanopores imbedded into a lipid bilayer constructed by homology modeling from the E. coli ClyA structure (PDB: 2WCD, 90% sequence identity). The inner pore lumen is shown as surface representation and shaded according to the "in vacuo" electrostatics (darker shade for negative regions, and lighter shade for positive regions, Pymol). The amino acid substitution that were tested are indicated in ClyA-AS (left). ClyA-RR pores contain two additional arginine residues per proteomer at positions 110 and 64 (right). Panel B) Current versus voltage relationship for ClyA-AS and ClyA-RR. Panel C) ssDNA (1a, 1 µM) and (Panel D) dsDNA (1, 170 nM) translocation through ClyA-RR nanopores at physiological ionic strength at +70 mV. The bottom current traces show a magnification of the DNA translocation events. The current signal was acquired at 10 kHz applying a 2-kHz low-pass Bessel filter. The buffer was 150 mM NaCl, 15 mM Tris HCl, pH 7.5, and the temperature 22° C.

For illustrative purpose only, FIG. 1 (panel A) shows a modified ClyA nanopore according to one embodiment described herein. The modified ClyA nanopore comprises a first opening 102, a mid-section 104, and a second opening 106. The lumen 108 extends from the first opening 102 through the mid-section 104 to the second opening 106 and has a total length of about 13 nm to about 15 nm. The first opening 102 and the mid-section 104 have a diameter of about 5 nm to about 7 nm. The luminal surface of the second opening 106 defines an electronegative constriction 112, wherein the narrowest cross-section has a diameter of about 3 nm to about 4 nm. The second opening 106 (with a length of about 3 nm to about 5 nm) of the modified ClyA nanopore is inserted into a membrane (e.g., a bilayer) 110 such that a solution in which the modified ClyA nanopore is present is separated into two sides and the first opening 102 is present in one side of the solution while the electronegative constriction 112 is present in another side of the solution. When a target polymer (e.g., target polynucleotide) is added on the same side as the first opening 102, the first opening 102 is a cis opening and the second opening 106 is a trans opening.

As used herein, the term "luminal surface" refers to the internal surface of a lumen that is exposed to a solution.

As used interchangeably herein, the term "electronegative constriction" or "negatively-charged constriction" refers to a constriction having a net negative surface charge. For example, the luminal surface of the second opening that defines an electronegative constriction has a net negative surface charge as shown in FIG. 1 (panel A).

In any of the modified ClyA nanopores described herein, the distance within the lumen from the first positive charge modification (e.g., the first positively-charged amino acid substitution) to the second positive charge modification (e.g., the second positively charged amino acid substitution) may vary within a range of about 0.5 nm to about 10 nm, or about 3 nm to about 7 nm. In some embodiments, the distance within the lumen from the first positive charge modification (e.g., the first positively-charged amino acid substitution) to the second positive charge modification (e.g., the second positively charged amino acid substitution) may be about 1 nm, about 2 nm, about 3 nm, about 4 nm, about 5 nm, about 6 nm, about 7 nm, about 8 nm, or about 9 nm.

Any forms of ClyA may be used to produce the modified ClyA nanopore described herein. For example, as described above, the amino acid sequences of various forms of ClyA, including, e.g., but not limited to wild-type ClyA (ClyA-WT) and ClyA-AS, and nucleotide sequences encoding the same are known in the art. Accordingly, in some embodiments, the modified ClyA nanopore may comprise a subunit polypeptide having an amino acid sequence that is at least about 80% (including, e.g., at least about 85%, at least about 90%, at least about 95%, or higher) identical to a reference ClyA amino acid sequence as described herein. In some embodiments, the modified ClyA nanopore may comprise a subunit polypeptide having an amino acid sequence that is at least about 80% (including, e.g., at least about 85%, at least about 90%, at least about 95%, or higher) identical to the amino acid sequence as set forth in SEQ ID NO: 1, which corresponds to the wild-type ClyA. Alternatively, the modified ClyA nanopore may comprise a subunit polypeptide having an amino acid sequence that is at least about 80% (including, e.g., at least about 85%, at least about 90%, at least about 95%, or higher) identical to the amino acid sequence as set forth in SEQ ID NO: 2, which corresponds to the amino acid sequence of ClyA-AS. In some embodiments, the modified ClyA nanopore may comprise up to 15 substitutions (e.g., 2, 3, 4, 5, 6, 7, 8, 9, 10, 11, 12, 13, 14, or 15 substitutions) compared to the amino acid sequences as set forth in SEQ ID NO: 1 or SEQ ID NO: 2 including the first and second positive charge modifications (e.g., the first and second positively-charged amino acid substitutions).

In any of the modified ClyA nanopores described herein, the first positive charge modification (e.g., the first positively-charged amino acid substitution) may be positioned within the first opening so as to permit capture of a negatively charged polymer (e.g., but not limited to a deoxyribonucleic acid (DNA) such as double stranded DNA or single-stranded DNA) within a solution exposed to the first opening. For example, the first positive charge modification (e.g., the first positively-charged amino acid substitution) may be located at position E106, S110, D114, D121, D122, E129, E85, E78, D268, D267, D265, E258, or combinations thereof in the amino acid sequence as set forth in SEQ ID NO: 1 or SEQ ID NO: 2.

In any of the modified ClyA nanopores described herein, the second positive charge modification (e.g., the second positively-charged amino acid substitution) may be positioned within the mid-section so as to permit translocation of the negatively charged polymer (e.g., but not limited to a deoxyribonucleic acid (DNA) such as double stranded DNA or single-stranded DNA) through the lumen of the pore. For example, the second positive charge modification (e.g., the second positively-charged amino acid substitution) may be located at position D74, D71, D64, E53, E161, D158, E46, E42, D41, or combinations thereof in the amino acid sequence as set forth in SEQ NO: 1 or SEQ ID NO: 2.

The modified ClyA nanopore can be homo-multimeric (e.g., all subunits within the nanopore are the same) or hetero-multimeric (e.g., at least one subunit is different from others within the nanopore). The modified ClyA nanopore may comprise any number of subunit polypeptides that are sufficient to form a lumen large enough to permit a target polymer (e.g., polynucleotide) pass through. In some embodiments, the modified ClyA nanopore may comprise 12 subunit polypeptides or more, including, e.g., 13 subunit polypeptides, and 14 subunit polypeptides, wherein at least one or more of the subunit polypeptides comprises the first and second positively-charged amino acid substitutions as described herein.

The modified ClyA nanopores can be used for distinguishing double stranded polynucleotides from single stranded polynucleotides, e.g., based on the dwell time in the nanopore and the current flowing through the pore. In addition, the modified ClyA nanopores can be used for characterizing, such as sequencing, polynucleotide sequences. The modified ClyA nanopores can also be used to distinguish modified bases, e.g., between methylated and unmethylated nucleotides.

The modified ClyA nanopores described herein provide higher frequency of capture and/or translocation of a polynucleotide through the nanopores in low ionic strength solutions, as compared to a ClyA nanopore without the first and second positively-charged substitutions described herein.

As used herein, the term "low ionic strength solution" refers to a solution with an ionic strength of less than 2 M, including, e.g., less than 1 M, less than 900 mM, less than 800 mM, less than 700 mM, less than 600 mM, less than 500 mM, less than 400 mM, less than 300 mM, less than 200 mM, less than 150 mM, or lower. In some embodiments, a lower ionic strength solution has an ionic strength of at least about 50 mM, at least about 100 mM, at least about 150 mM, at least about 200 mM, at least about 300 mM, at least about 400 mM, at least about 500 mM, at least about 600 mM, at least about 700 mM, at least about 800 mM, at least about 900 mM, at least about 1 M, or higher. Combinations of the above-references ranges are also encompassed. For example, a low ionic strength solution may have an ionic strength of about 100 mM to about 600 mM, or about 150 mM to about 300 mM. Any salt can be used to yield a solution with appropriate ionic strength. In some embodiments, alkaline salt (e.g., but not limited to potassium chloride or sodium chloride) can be used in the low ionic strength solution.

The modified ClyA nanopores can discriminate between different nucleotides under a range of conditions. In particular, the pores can discriminate between nucleotides under conditions that are favorable to the characterizing, such as sequencing, of nucleic acids. The extent to which the modified ClyA nanopores can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The modified ClyA nanopores may also be used to identify polynucleotide polymers from the interaction with one or more monomers rather than on a nucleotide by nucleotide basis.

In some embodiments, modified ClyA nanopores provided herein may be used for characterizing nucleic acid-protein interactions. In some embodiments, the nanopores can be used interrogate protein-nucleic acids using different sensing modes such as, for example, by scanning and mapping the locations of binding sites along a nucleic acid and/or by probing the strength of interactions between a protein and nucleic acid. In some embodiments, native charges of a nucleic acid may be leveraged to apply an electrophoretic force to a nucleic acid-protein complex. For example, in some embodiments, DNA-protein interactions may be evaluated using voltage-driven threading of single DNA molecules through a protein nanopore. In such embodiments, electrical force applied to an individual DNA protein complex (e.g., a DNA-exonuclease I complex, a DNA-helicase complex, a DNA-clamp complex) may pull the two molecules apart, while at the same time ion current changes may be used to evaluate the dissociation rate of the complex. In some embodiments, modified ClyA nanopores provided herein may be used for detection and characterization of nucleic acid-protein interactions involving nucleic acid and other nucleic acid binding proteins such as transcription factors, enzymes, DNA packaging proteins and others.

The modified ClyA nanopores may be isolated, substantially isolated, purified or substantially purified. The modified ClyA nanopores can be isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, one or more of the modified ClyA nanopores may be present in a membrane. Suitable membranes are discussed below.

The modified ClyA nanopore may be present as an individual or single pore. Alternatively, the modified ClyA nanopores may be present in a homologous or heterologous population of two or more pores. In some embodiments, the modified ClyA nanopores may be arranged in an array of microwells, wherein each microwell contains at least one nanopore is in a membrane.

Homo-Multimeric ClyA Nanopores

Homo-multimeric nanopores comprising identical modified ClyA nanopore subunit polypeptides are also provided herein. The homo-multimeric nanopore may comprise any embodiment of the modified ClyA nanopore subunit polypeptides described herein. The homo-multimeric nanopore can be used for characterizing, such as sequencing, polynucleotides, and/or detecting the presence or absence of single stranded polynucleotide vs double stranded polynucleotide. The homo-multimeric nanopore described herein may have any of the advantages discussed above.

The homo-multimeric pore may contain any number of modified ClyA nanopore subunit polypeptides. The pore typically comprises at least 10, at least 11, at least 12, at least 13, or at least 14 identical modified ClyA nanopore subunit polypeptides, such as 12, 13, or 14 identical modified ClyA nanopore subunit polypeptides.

Methods for making pores are discussed in more detail below.

Hetero-Multimeric ClyA Nanopores

Hetero-multimeric nanopores comprising at least one modified ClyA nanopore subunit polypeptides are also provided herein. The hetero-multimeric nanopores can be used for characterizing, such as sequencing, polynucleotides, and/or detecting the presence or absence of single stranded polynucleotide vs double stranded polynucleotide. Hetero-multimeric nanopores can be made using methods known in the art (e.g., Protein Sci. 2002 July; 11(7):1813-24).

The hetero-multimeric pore contains sufficient subunit polypeptide to form the pore. The subunit polypeptides may be of any type. The pore typically comprises at least 10, at least 11, at least 12, at least 13, or at least 14 subunit polypeptides, such as 12, 13, or 14 subunit polypeptides.

In some embodiments, all of the subunit polypeptides (such as 12, 13, or 14 of the subunit polypeptides) are modified ClyA nanopore subunit polypeptides and at least one of them differs from the others. In some embodiments, the pore comprises 12 or 13 modified ClyA nanopore subunit polypeptides and at least one of them differs from the others. They may all differ from one another.

In some embodiments, at least one of the subunit polypeptides is not a modified ClyA nanopore subunit polypeptide as described herein. In this embodiment, the remaining monomers may be any one of the modified ClyA nanopore subunit polypeptides described herein. Hence, the pore may comprise 12, 11, 10, 9, 8, 7, 6, 5, 4, 3, 2, or 1 modified ClyA nanopore subunit polypeptide(s). The modified ClyA nanopore subunit polypeptide(s) that form the nanopore can be the same or different.

Methods for making pores are discussed in more detail below.

Polynucleotide Characterization

Another aspect of the present disclosure provides a method of characterizing a target polynucleotide. The method comprises: (a) providing, in a low ionic strength solution of about 50 mM to about 1 M, a modified ClyA nanopore according to any embodiment described herein and a membrane, wherein the modified ClyA nanopore is present in the membrane; (b) adding in the low ionic strength solution of step (a) the target polynucleotide; and (c) measuring, during application of a potential across the nanopore, ion flow through the modified ClyA nanopore, wherein the ion flow measurements are indicative of one or more characteristics of the target polynucleotide. In some embodiments, the target polynucleotide is added to the cis side of the low ionic strength solution.

In some embodiments, the low ionic strength solution may have an ionic strength of about 50 mM to about 300 mM, or about 150 mM to about 300 mM.

The target polynucleotide may also be called the template polynucleotide or the polynucleotide of interest.

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e., lack a nucleobase). A nucleotide may also lack a nucleobase and a sugar.

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated. For instance, the method described herein may concern characterizing 2, 3, 4, 5, 6, 7, 8, 9, 10, 20, 30, 50, 100 or more polynucleotides. If two or more polynucleotides are characterized, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

The polynucleotide may comprise an attached species such as a protein or analyte. The polynucleotide may comprise a hybridized probe.

Sample

Each analyte is typically present in any suitable sample. The method can be carried out on two or more samples that are known to contain or suspected to contain the analytes. Alternatively, the method may be carried out on two or more samples to confirm the identity of two or more analytes whose presence in the samples is known or expected. In some embodiments, the method may be carried out on samples to distinguish double stranded polynucleotides from single-stranded polynucleotides.

The first sample and/or second sample may be a biological sample. The methods described herein may be carried out in vitro using at least one sample obtained from or extracted from any organism or microorganism. The first sample and/or second sample may be a non-biological sample. The non-biological sample can be a fluid sample. Examples of non-biological samples include surgical fluids, water such as drinking water, sea water or river water, and reagents for laboratory tests.

The first sample and/or second sample is typically processed prior to being used in the methods described herein, for example by centrifugation or by passage through a membrane that filters out unwanted molecules or cells, such as red blood cells. The first sample and/or second sample may be measured immediately upon being taken. The first sample and/or second sample may also be typically stored prior to assay, preferably below −70° C.

Characterization

The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the methods described herein, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The target polynucleotide is contacted with any one of the modified ClyA nanopores described herein. The pore is typically present in a membrane. Suitable membranes are discussed below. The method may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in International Application No. PCT/GB08/000562 (WO 2008/102120).

A variety of different types of measurements may be made. This includes without limitation: electrical measurements and optical measurements. Possible electrical measurements include: current measurements, impedance measurements, tunneling measurements (Ivanov AP et al., Nano Lett. 2011 Jan. 12; 11(1):279-85), and FET measurements (International Application WO 2005/124888). Optical measurements may be combined with electrical measurements (Soni GV et al., Rev Sci Instrum. 2010 January; 81(1): 014301). The measurement may be a transmembrane current measurement such as measurement of ionic current flowing through the pore. Alternatively the measurement may be a fluorescence measurement indicative of ion flow through the channel such as disclosed by Heron et al, J. Am. Chem. Soc., 2009, 131 (5), 1652-1653 or measurement of a voltage across the membrane using a FET.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method can be carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This may be described as strand sequencing.

The method may involve measuring the current passing through the pore as the polynucleotide moves with respect to the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations. While the modified ClyA nanopores described herein can be used to characterize a polynucleotide at high salt solution, the modified ClyA nanopores can permit efficient capture and/or translocation of a polynucleotide (e.g., double stranded DNA or single stranded DNA) through the nanopore even in low ionic strength solutions as described above.

The method is typically carried out in the presence of a buffer. In the exemplary apparatus discussed above, the buffer is present in the aqueous solution in the chamber. Any buffer may be used in the methods described herein. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5 or 8.0.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Polynucleotide Binding Protein

In some embodiments, the method for characterizing a target polynucleotide may include adding a polynucleotide binding protein in the low ionic strength solution such that the polynucleotide binding protein binds to the target polynucleotide and controls the movement of the target polynucleotide through the modified ClyA nanopore.

The polynucleotide binding protein may be any protein that is capable of binding to the polynucleotide and controlling its movement through the pore. Examples of the polynucleotide binding proteins include, but are not limited to helicases, polymerases, exonucleases, DNA clamps, etc. The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein.

Helicase(s) and Molecular Brake(s)

In one embodiment, the method comprises:

(a) providing the polynucleotide with one or more helicases and one or more molecular brakes attached to the polynucleotide;

(b) adding the polynucleotide in the low ionic strength solution that comprises a modified ClyA nanopore present in a membrane, and applying a potential across the pore such that the one or more helicases and the one or more molecular brakes are brought together and both control the movement of the polynucleotide through the pore;

(c) measuring, during application of a potential across the nanopore, ion flow through the modified ClyA nanopore, as the polynucleotide moves with respect to the pore wherein the ion flow measurements are indicative of one or more characteristics of the polynucleotide and thereby characterizing the polynucleotide. This type of method is discussed in detail in International Application No.PCT/GB2014/052737.

Membrane

The modified ClyA nanopores described herein may be present in a membrane. In the method of characterizing a polynucleotide, the polynucleotide is typically contacted with a modified ClyA nanopore in a membrane. Any membrane may be used. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic or lipophilic, whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviors from vesicles through to laminar membranes. Membranes formed from these triblock copolymers hold several advantages over biological lipid membranes. Because the triblock copolymer is synthesized, the exact construction can be carefully controlled to provide the correct chain lengths and properties to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

The membrane is most preferably one of the membranes disclosed in International Application No. PCT/GB2013/052766 or PCT/GB2013/052767.

The amphiphilic molecules may be chemically-modified or functionalized to facilitate coupling of the polynucleotide.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately 10-8 cm s−1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

In some embodiments, the polynucleotide can be coupled to the membrane comprising any one of the modified ClyA nanopores described herein. The method may comprise coupling the polynucleotide to the membrane comprising any one of the modified ClyA nanopores described herein. The polynucleotide is preferably coupled to the membrane using one or more anchors. The polynucleotide may be coupled to the membrane using any known method.

Double Stranded Polynucleotide Sequencing

In some embodiments, the polynucleotide may be double stranded. If the polynucleotide is double stranded, the method may further comprises before the contacting step ligating a hairpin adaptor to one end of the polynucleotide. The two strands of the polynucleotide may then be separated as or before the polynucleotide is contacted or interacted with a modified ClyA nanopore as described herein. The two strands may be separated as the polynucleotide movement through the pore is controlled by a polynucleotide binding protein, such as a helicase, or molecular brake. This is described in International Application No. PCT/GB2012/051786 (published as WO 2013/014451). Linking and interrogating both strands on a double stranded construct in this way increases the efficiency and accuracy of characterization.

Round the Corner Sequencing

In a preferred embodiment, a target double stranded polynucleotide is provided with a hairpin loop adaptor at one end and the method comprises contacting the polynucleotide with any one of the modified ClyA nanopores described herein such that both strands of the polynucleotide move through the pore and taking one or more measurements as the both strands of the polynucleotide move with respect to the pore wherein the measurements are indicative of one or more characteristics of the strands of the polynucleotide and thereby characterizing the target double stranded polynucleotide. Any of the embodiments discussed above equally apply to this embodiment.

Leader Sequence

Before the contacting step, the method preferably comprises attaching to the polynucleotide a leader sequence which preferentially threads into the pore. The leader sequence facilitates any of the methods described herein. The leader sequence is designed to preferentially thread into any one of the modified ClyA nanopores described herein and thereby facilitate the movement of polynucleotide through the nanopore. The leader sequence can also be used to link the polynucleotide to the one or more anchors as discussed above.

Modified Polynucleotides

Before characterization, a target polynucleotide may be modified by contacting the polynucleotide with a polymerase and a population of free nucleotides under conditions in which the polymerase forms a modified polynucleotide using the target polynucleotide as a template, wherein the polymerase replaces one or more of the nucleotide species in the target polynucleotide with a different nucleotide species when forming the modified polynucleotide. The modified polynucleotide may then be provided with one or more helicases attached to the polynucleotide and one or more molecular brakes attached to the polynucleotide. This type of modification is described in International Application No. PCT/GB2015/050483. Any of the polymerases discussed herein may be used.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. A primer or a 3' hairpin is typically used as the nucleation point for polymerase extension.

Characterization, such as sequencing, of a polynucleotide using a transmembrane pore typically involves analyzing polymer units made up of k nucleotides where k is a positive integer (i.e., 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e., high values of k, it can become difficult to resolve the measurements produced by different k-mers, to the detriment of deriving information about the polynucleotide, for example an estimate of the underlying sequence of the polynucleotide.

By replacing one or more nucleotide species in the target polynucleotide with different nucleotide species in the modified polynucleotide, the modified polynucleotide contains k-mers which differ from those in the target polynucleotide. The different k-mers in the modified polynucleotide are capable of producing different current measurements from the k-mers in the target polynucleotide and so the modified polynucleotide provides different information from the target polynucleotide. The additional information from the modified polynucleotide can make it easier to characterize the target polynucleotide. In some instances, the modified polynucleotide itself may be easier to characterize. For instance, the modified polynucleotide may be designed to include k-mers with an increased separation or a clear separation between their current measurements or k-mers which have a decreased noise.

The polymerase preferably replaces two or more of the nucleotide species in the target polynucleotide with different nucleotide species when forming the modified polynucleotide. The polymerase may replace each of the two or more nucleotide species in the target polynucleotide with a distinct nucleotide species. The polymerase may replace each of the two or more nucleotide species in the target polynucleotide with the same nucleotide species.

If the target polynucleotide is DNA, the different nucleotide species in the modified typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the target polynucleotide is RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcytidine. The different nucleotide species may be any of the universal nucleotides discussed above.

The polymerase may replace the one or more nucleotide species with a different nucleotide species which comprises a chemical group or atom absent from the one or more nucleotide species. The chemical group may be a propynyl group, a thio group, an oxo group, a methyl group, a hydroxymethyl group, a formyl group, a carboxy group, a carbonyl group, a benzyl group, a propargyl group or a propargylamine group.

The polymerase may replace the one or more nucleotide species with a different nucleotide species which lacks a chemical group or atom present in the one or more nucleotide species. The polymerase may replace the one or more of the nucleotide species with a different nucleotide species having an altered electronegativity. The different nucleotide species having an altered electronegativity preferably comprises a halogen atom.

The method preferably further comprises selectively removing the nucleobases from the one or more different nucleotides species in the modified polynucleotide.

Other Characterization Method

In another embodiment, a polynucleotide is characterized by detecting labelled species that are released as a polymerase incorporates nucleotides into the polynucleotide. The polymerase uses the polynucleotide as a template. Each labelled species is specific for each nucleotide. The polynucleotide is contacted with a modified ClyA nanopore described herein, a polymerase and labelled nucleotides such that phosphate labelled species are sequentially released when nucleotides are added to the polynucleotide(s) by the polymerase, wherein the phosphate species contain a label specific for each nucleotide. The polymerase may be any of those discussed above. The phosphate labelled species are detected using the pore and thereby characterizing the polynucleotide. This type of method is disclosed in European Application No. 13187149.3 (published as EP 2682460). Any of the embodiments discussed above equally apply to this method.

Kits

Another aspect of the present disclosure also provides a kit for characterizing a target polynucleotide. The kit comprises any one of the modified ClyA nanopores described herein and the components of a membrane. The membrane is preferably formed from the components. The pore is preferably present in the membrane. The kit may comprise components of any of the membranes disclosed above, such as an amphiphilic layer or a triblock copolymer membrane.

The kit may further comprise a polynucleotide binding protein.

The kit may further comprise one or more anchors for coupling the polynucleotide to the membrane.

The kit may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in any one of the methods described herein or details regarding for which organism the method may be used.

Apparatus

Another aspect described herein also provides an apparatus for characterizing a target polynucleotide. The apparatus comprises a plurality of modified ClyA nanopores as described herein and a plurality of membranes. In some embodiments, the plurality of the modified ClyA nanopores are present in the plurality of membranes. In some embodiments, the numbers of modified ClyA nanopores and membranes are equal. In one embodiment, a single modified ClyA nanopore is present in each membrane.

The apparatus can further comprises instructions for carrying out any of the methods as described herein. The apparatus may be any conventional apparatus for polynucleotide analysis, such as an array or a chip. Any of the embodiments discussed above with reference to the methods, e.g., for characterizing a target polynucleotide, are equally applicable to the apparatus described herein. The apparatus may further comprise any of the features present in the kit described herein.

In some embodiments, the apparatus is set up to carry out any of the methods described herein, e.g., for characterizing a target polynucleotide.

In one embodiment, the apparatus comprises: (a) a sensor device that is capable of supporting the plurality of modified ClyA nanopores and membranes and that is operable to perform polynucleotide characterization using the nanopores and membranes; and (b) at least one port for delivery of material for performing the characterization.

Alternatively, the apparatus may comprise: (a) a sensor device that is capable of supporting the plurality of modified ClyA nanopores and membranes and that is operable to perform polynucleotide characterization using the nanopores and membranes; and (b) at least one reservoir for holding material for performing the characterization.

In another embodiment, the apparatus may comprise: (a) a sensor device that is capable of supporting the membrane and plurality of modified ClyA nanopores and membranes and that is operable to perform polynucleotide characterizing using the pores and membranes; (b) at least one reservoir for holding material for performing the characterizing; (c) a fluidics system configured to controllably supply material from the at least one reservoir to the sensor device; and (d) one or more containers for receiving respective samples, the fluidics system being configured to supply the samples selectively from one or more containers to the sensor device.

The apparatus may be any of those described in International Application No. No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Precise Nanoscale Engineering of Nanopores to Enable DNA Translocation at Physiological Ionic Strengths Many important processes in biology involve the translocation of a biopolymer through nanometer-scale pores, such as nucleic acid transport across nuclear pores, protein translocation through membrane channels, and viral DNA injection into target cells. Moreover, biological and artificial nanopores embedded in insulating membranes provide useful tools to investigate this process and may find applications in rapid DNA or protein sequencing, single molecule DNA sequencing and analysis, and biomarker sensing. The mechanism of DNA translocation across nanopores has been particularly investigated. The crystal structure of several portal bacteriophage proteins revealed that during DNA packing and injection, dsDNA translocates across a narrow nanopore (~3.5 nm) with a strong negative surface that is decorated by rings of positive charges. The electronegative inner surface of the nanopore is proposed to facilitate the sliding of negatively charged DNA, while the role of the positive charges is thought to facilitate this process. In this Example, it is found that at physiological ionic strengths the electrophoretic translocation of DNA across ClyA nanopores, which have the same a fold, size and overall internal charge of portal proteins, can be observed only if two rings of positive charges are engineered at wide-entrance and mid-section of the nanopore. Surprisingly, the strongly electronegative 3.3 nm internal constriction of the nanopore did not require modifications. The findings indicate that the engineered positive charges are important to align the DNA in order to overcome the entropic and electrostatic barriers for DNA translocation through the narrow constriction. Without wishing to be bound by theory, in order to translocate through narrow nanopores with negative charge density a DNA molecule should be oriented.

The ionic current flowing through biological nanopores reconstituted into lipid membranes has been used to identify small molecules or folded proteins and to monitor chemical or enzymatic reactions at the single-molecule level. The electrophoretic translocation of DNA across nanopores reconstituted into artificial membranes holds great promise for practical applications such as DNA sequencing, and biomarker recognition. ɸ29 portal protein, which is not a membrane protein per se, was found to insert into black lipid bilayers and such nanopores electrophoretically translocated dsDNA at 1.0/0.5 mM NaCl. However, the exact hydrophobic modifications of the nanopore that allowed membrane insertion were not known. Indeed, ɸ29 nanopores occasionally released from the lipid membranes, thus posing limitations in practical applications. dsDNA has been shown to translocate through artificial nanopores prepared on solid-state membranes, which with the exception of atom-thin material such as graphene or bilayer of molybdenum disulfide, mostly have a negative internal surface charge. In such nanopores with radii comparable to the Debye length of the solution, the surface potential produced by the electric-double layer (EDL) on the inner nanopore walls overlaps, resulting in a large electrostatic barrier for the entry of DNA into the nanopore. As a consequence, the translocation of DNA across solid-state nanopores at physiological ionic strength using large nanopores (10 nm) or using small nanopores (~3.5 nm) in 340 nM salt or under asymmetry salt concentrations. Additionally, the translocation of DNA across solid-state nanopores with diameters comparable to the size of DNA (~2.2 nm for the B-form of dsDNA and ~1 nm for ssDNA) has yet to be observed at physiological ionic strengths.

The ClyA nanopore, a dodecameric protein with an internal constriction of ~3.3 nm (FIG. 1, Panel A) has been used as a tool to investigate folded proteins. Although dsDNA translocation across the nanopore was observed at 2.5 M NaCl solutions, the strong negative interior of the pore (FIG. 1, Panel A) prevented DNA translocation at lower ionic strengths. In this Example, the ClyA nanopore was engineered, enabling it to translocate of DNA at physiological ionic strengths. This is useful in many applications where electrostatic interactions between molecules and DNA are important, for example in DNA sequencing or mapping where enzymes are used to control the translocation of DNA across the nanopore or to study DNA-protein interactions. The DNA translocation was observed after two rings of positive charges were added at wider cis side of the nanopore, while modification of the more constricted trans entry of the nanopore did not improve the efficiency of DNA translocation. In addition, the modifications did not change the ion selectivity of the nanopore and mirrored the charge distribution of φ29 portal protein. Further, the engineered pores allowed the translocation of DNA only from the wide-side of the nanopore. Interestingly, many proteins that slide on DNA display a surface charge similar to the engineered ClyA nanopores, indicating that the alternation of positive and negative charges might provide a general mechanism for improving the translocation of DNA across nanoscales. This Example shows that the precise engineering of the shape and internal surface charge of the nanopore is important for the translocation and sliding of DNA across nano-scale pores with diameter similar to that of DNA.

Results

Engineering ClyA Nanopores to Capture DNA

ClyA-AS (FIG. 1, Panel A; FIG. 11, Panel A) is an engineered version of cytolysin A from *Salmonella typhi* selected for its favorable proprieties in planar lipid bilayers and in which the translocation of ssDNA or dsDNA is only observed above 2.0 M NaCl ionic strengths. Most likely, at low ionic strengths, the strong negative electrostatic potential inside the nanopore (FIG. 11, Panel B) prevents DNA entry and translocation, while at high ionic strengths, the charges of the nanopore surface are effectively screened. To induce the capture of DNA by the nanopores at physiological ionic strengths, the internal charges of the ClyA-AS nanopore were modified (Tables 1 and 2 and FIG. 1, Panel A; FIG. 11, Panel A). Occasionally ClyA variants showed transient reduction of the open pore conductance (gating). As a measurement of gating the gating voltage ($V_G$), defined as the applied voltage at which a typical nanopore remained open for a 30 seconds timespan (Table 1) was used. The translocation of DNA through the modified nanopore was tested at $V_G$ by adding 1 µM of a 90 meric 3'-biotinylated ssDNA molecule (FIG. 1, Panel A, Table 3), followed by its complementary strand at equimolar concentration (FIG. 1, Panel B, Table 3), and finally neutravidin (1.2 µM, monomer).

Figure 6:
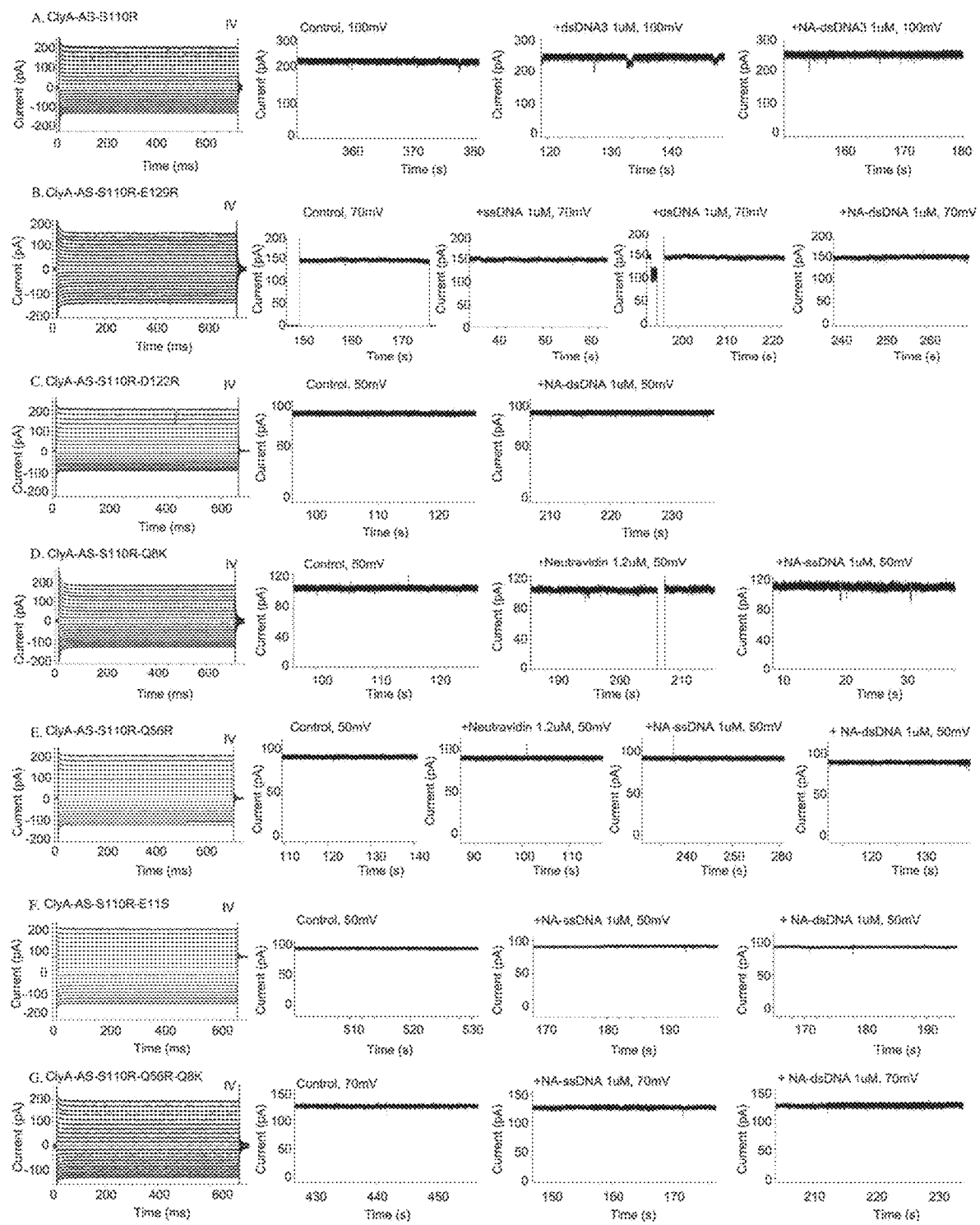
FIG. 6. DNA translocation from the cis side of ClyA nanopores in 0.15 M NaCl solutions. For each indicated mutant (Panels A-G) it is reported: the IV relationship (voltage ramp from +100 to −100 mV in 21 s and 10 mV voltage steps) and a representative current trace under positive VG applied potential (Table 5) before and after adding 1 µM of a biotinylated ssDNA (1a, Table 3) to the cis compartment. A variety of current traces is also shown after the subsequent addition of 1.2 µM neutravidin (monomer) and 1 µM of the complementary ssDNA (1b Table 1) to the cis solution. The electrical recordings were carried out in 0.15 M NaCl, 15 mM Tris-HCl. pH 7.5 at 22° C. Data were recorded by applying a 2-kHz low-pass Bessel filter and using a 100 µs (10 kHz) sampling rate.

A single ring of positive charges in the form of arginine residues was introduced at the cis entry of ClyA-AS (S110R, ClyA-R, FIG. 1, Panel A; FIG. 11, Panel A), and then three sections of the nanopore: the cis entry, the midsection, and the trans constriction were modified (FIG. 1, Panel A; FIG. 11, Panel A). The substitution of neutral residues with positive residues at the cis opening of ClyA-R showed no DNA translocation in 150 mM NaCl (Table 1, Table 2). Additional positive charges at the cis opening showed either no channel insertion into planar lipid bilayers (ClyA-R-E106R and ClyA-R-D114R) or no DNA translocation in 150 mM NaCl (ClyA-R-D122R and ClyA-R-D129R). Arginine rings in the midsection of the ClyA-R nanopore induced ssDNA (FIG. 1, Panel C) and dsDNA (FIG. 1, Panel D) translocation when the negatively charged glutamate residues at position 64 were replaced by arginine (D64R, ClyA-RR) but not when a neutral side chain at a nearby position was substituted with arginine (Q56R). The substitution of either a neutral side chain at a nearby position with arginine (Q56R), the removal of negatively charged residues in the transmembrane region (ClyA-R-E11S) or the addition of a positively charged residue (ClyA-R-Q8K) induced no DNA translocation events in 150 mM NaCl solutions (FIG. 6). Surprisingly, the substitution of neutral residues with positively charged residues in both the midsection and trans entry of ClyA-R (ClyA-R-Q56R-Q8K) also did not induce DNA translocation events (FIG. 6). All mutations tested except ClyA-R-D129R reduced the gating voltage (Table 1). ClyA-RR was the only ClyA mutant that showed DNA induced current events following the addition of either ssDNA or dsDNA to the cis side of the nanopore (+70 mV, FIGS. 1C-D and 6). Despite the observation that only ClyA-RR allowed DNA translocation, ClyA-RR, ClyA-R and ClyA-AS all showed the same ion selectivity ($P_{Na+}/P_{Cl-}$=1.9±0.7, 2.0±1.6, 1.9±0.9, respectively, Table 4), indicating that the ion selectivity of the nanopore is dominated by the charge distribution of the transmembrane region of the nanopore and is not induced by an enhanced electro-osmotic flow through the nanopore.

More generally, the substitution of the first amino acid in Region A (as denoted in FIG. 20) may have at least a delta 1 of added positive charge (namely substitution of a neutral amino acid by a positively charged amino acid) and the substitution in Region B may have at least a delta 2 of added positive charge (namely substitution of a negatively charged amino-acid by a positively charged amino acid).

In order to obtain a greater insight into the changes of the electrostatic potential caused by the two additional arginine rings, full-atom homology models of ClyA-AS and ClyA-RR were constructed using VMD (Humphrey et al. J. Mol. Graphics (1996) 14: 33-38) and NAMD (Phillips et al., J. Comput. Chem. (2005) 26: 1781-1802) starting from the *E. coli* ClyA crystal structure. The adaptive Poisson-Boltzmann solver (APBS), e.g., described in Baker et al., PNAS (2001) 98: 10037-10041; Dolinsky et al., Nucleic Acids Res. (2004) 32: W665-W667; and Dolinsky et al., *Nucleic Acid Res.* (2007) 35: W522-W525) was employed to calculate the electrical potential distribution of both pores in 150 mM NaCl (FIG. 11, Panel B). In ClyA-AS, the potential at the center of the pore was found to be increasingly negative moving from the cis entry, through the midsection, and to the trans entry (averaging −2.6, −4.8, and −15.2 mV, respectively). In the case of ClyA-RR, a rise in the potential could be observed at both the cis entry and the midsection of the pore (averaging −0.3 and −1.1 mV, respectively). The potential in the trans constriction appeared to decrease further to an average of −17.3 mV. It should be noted that these values are calculated when no external bias is applied.

TABLE 1

Table 1: Electrical properties of engineered ClyA nanopore variants. The activities of the nanopores were tested by adding ~0.1 ng of oligomeric proteins to the cis chamber. A negative activity indicates that no channel insertions were observed. VG is the gating voltage and represents the highest applied voltage at which no gating events were observed within a 30-second timespan. DNA translocation indicates that a dsDNA rotaxane could be formed. Each data point is the average of at least three experiments and the error is the standard deviation. Experiments were carried out in 0.15 M NaCl, 15 mM Tris HCl, pH 7.5 solutions.

| Pore variants | Bilayer activity | IO + 100 mV IO1 − 00 Mv (pA) | Rectification ratio | VG (mV) | DNA Capture (cis) | DNA Translocation (cis) |
|---|---|---|---|---|---|---|
| ClyA-AS | + | +190 ± 13 −138 ± 6 | 1.4 ± 0.1 | +100 | − | − |
| ClyA-AS-S110R (ClyA-R) | + | +198 ± 1 −127 ± 2 | 1.6 ± 0.0 | +100 | − | − |
| ClyA-R-E106R | − | − | − | − | − | − |
| ClyA-R-D114R | − | − | − | − | − | − |
| ClyA-R-D122R | + | +207 ± 2 −99.8 ± 2 | 2.1 ± 0.1 | +50 | − | − |
| ClyA-R-E129R | + | +171 ± 25 −161 ± 24 | 1.1 ± 0.2 | +100 | − | − |
| ClyA-R-D64R (ClyA-RR) | + | +198 ± 8 −110 ± 4 | 1.8 ± 0.1 | +70 | + | cis |
| ClyA-R-Q56R | + | +202 ± 8 −128 ± 3 | 1.6 ± 0.1 | +50 | − | − |
| ClyA-R-Q8K | + | +202 ± 15 −147 ± 18 | 1.4 ± 0.2 | +50 | − | − |
| ClyA-R-E11S | + | +194 ± 4 −154 ± 0 | 1.3 ± 0.03 | +70 | − | − |
| ClyA-R-Q56R-Q8K | + | +207 ± 20− 150 ± 15 | 1.4 ± 0.2 | +50 | | |

DNA Rotaxane as a proof of DNA Translocation

A rotaxane is a dumbbell shaped molecule formed by a macrocycle that encircles a thread locked by two stoppers. In this Example, two nanopore/DNA rotaxanes were formed in 150 mM NaCl solutions to prove the translocation of ssDNA and dsDNA through the nanopore. The first rotaxane was formed using a 100 mer 5'-biotinylated ssDNA molecule as the initial thread (2a, Table 3) added to the cis compartment. The second rotaxane was formed using a 3'-biotinylated 59 base pairs dsDNA molecule extended with a 31 bases 3' biotin overhang (1a/1c, Table 3). The rotaxanes were locked by adding on the opposite side of the nanopore another biotinylated ssDNA molecule, 2b (50 mer, 5'-biotinylated) or 1d (31 mer, 3'-biotinylated), designed to hybridize with the overhangs of 2a or 1a/1c, respectively. Both cis and trans solutions contained Neutravidin (NA, 0.3 µM), which complexed with biotin and prevented the full translocation of the DNA strands across the nanopore.

Figure 2:
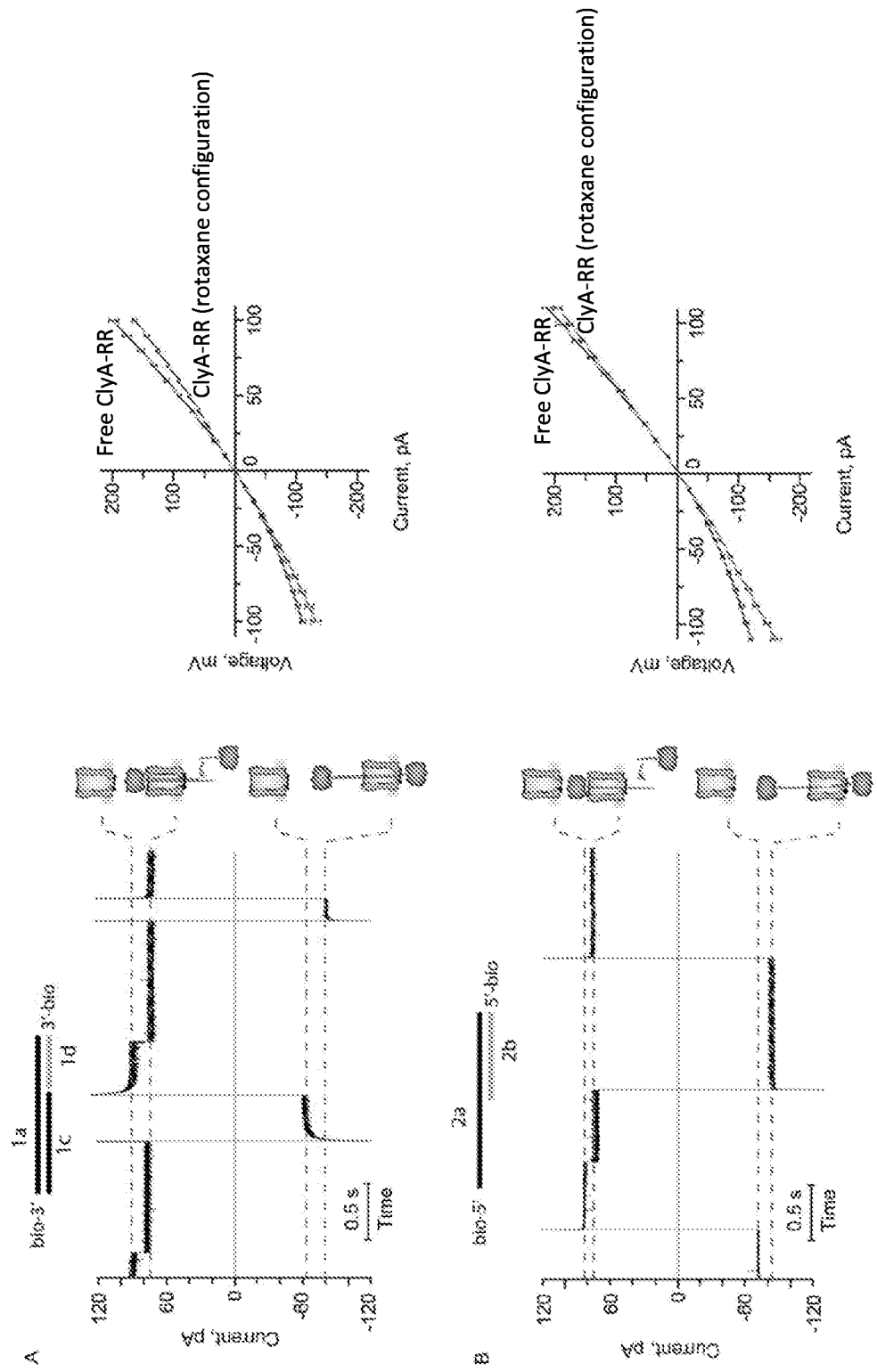
FIG. 2. DNA rotaxane formation in 150 mM NaCl solutions. Panel A) A dsDNA rotaxane was formed at +50 mV by adding a hybrid dsDNA/ssDNA thread 1a/1c (1.0 µM) complexed with neutravidin (1.2 µM, monomer) to the cis compartment a 31 bases single stranded overhang at the 5' that was used to hybridize with 1d (1.0 µM), a biotinylated ssDNA molecule complementary to the ssDNA overhang of 1a/1c. Thus, a nanopore/DNA rotaxane is formed only if 1a/1c translocates the nanopore. When DNA occupied the lumen of ClyA the open pore current was reduced at positive applied potentials ($I_{RES}$+50=84±7, average±S.D., N=3) and enhanced at negative applied potentials ($I_{RES}$−50=1.11±0.06, average±S.D., N=3). Panel B) A ssDNA/dsDNA hybrid rotaxane was formed at +50 mV by adding a 5' biotinylated ssDNA thread 2a (1.0 µM, black line) complexed with neutravidin (1.2 µM, monomer) to the cis compartment of a ClyA-RR nanopore. A second 5' biotinylated ssDNA molecule 2b (1.0 µM) complementary to the 3' end of 2a and complexed with neutravidin (1.2 µM, monomer) was added to the trans compartment. Upon rotaxane formation, the reversal of the applied potential to −50 mV induced a current enhancement ($I_{RES}$−50=1.16±0.03, average±S.D., N=3), indicating that the hybrid ssDNA/dsDNA is assembled. The right of the current traces show the voltage relationship (IV curve) for free ClyA-RR and ClyA-RR in a rotaxane configuration. The black and grey lines in FIG. 2, Panels A and B, indicate the DNA configuration of the two rotaxanes. The buffer used was 15 mM Tris HCl, pH 7.5, and the temperature 22° C. The DNA sequences are shown in Table 3.
Figure 3:
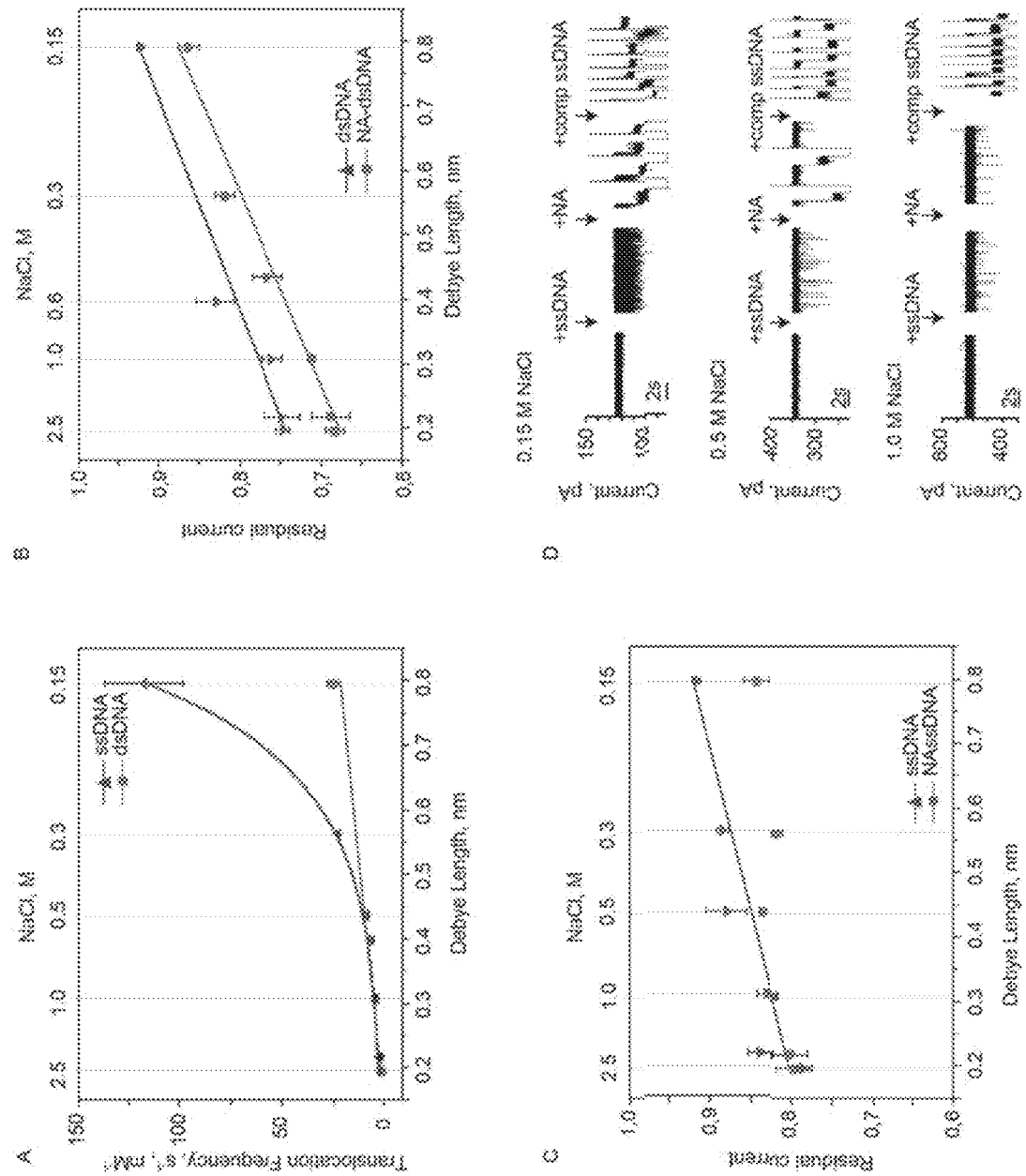
FIG. 3. Ionic strength dependency of DNA translocation and threading. Panel A) Debye strength dependency of the frequency of translocation for dsDNA (circles) and ssDNA (triangles). The frequency of dsDNA translocation events fitted well to a linear regression ($R^2$=0.98), while the frequency of ssDNA fitted better to a single exponential ($R^2$=0.99) than a linear regression ($R^2$=0.78). Panel B) Dependency of the residual current of dsDNA (triangles) and Neutravidin:dsDNA complex (circles) blockades on the solution Debye length. The lines represent linear regressions. Panel C) Same as in Panel B but for ssDNA. Panel D) Ionic strength dependency of DNA threading. Under +70 mV applied potential, the initial addition of ssDNA (1a, 1 µM) to the cis side of ClyA-RR induced fast current blockades to ClyA-RR open pore current. The subsequent addition of Neutravidin (1.2 µM, cis) induced long lasting current blockades in 150 and 300 mM NaCl solutions, which are most likely due to the threading of ssDNA. This was not observed in 1 M NaCl solution (or higher), where the blockades remained transient. Further addition of the complimentary ssDNA (1a, 1 µM, cis) induced permanent blockades at all ionic strengths due to the threading of dsDNA. After each permanent DNA capture event, the open pore was regenerated by manual reversal of the potential to −70 mV. Spikes above and below the open pore current level represent capacitive transients following the potential reversal. The electrical recordings were carried out in 15 mM Tris HCl, pH 7.5, at 22° C. Data were by applying a 10-kHz low-pass Bessel filter and using a 20 µs (50 kHz) sampling rate and are listed in Table 7. At 150 mM NaCl and additional digital 2-kHz low-pass Bessel filter was applied to the current traces.
Figure 7:
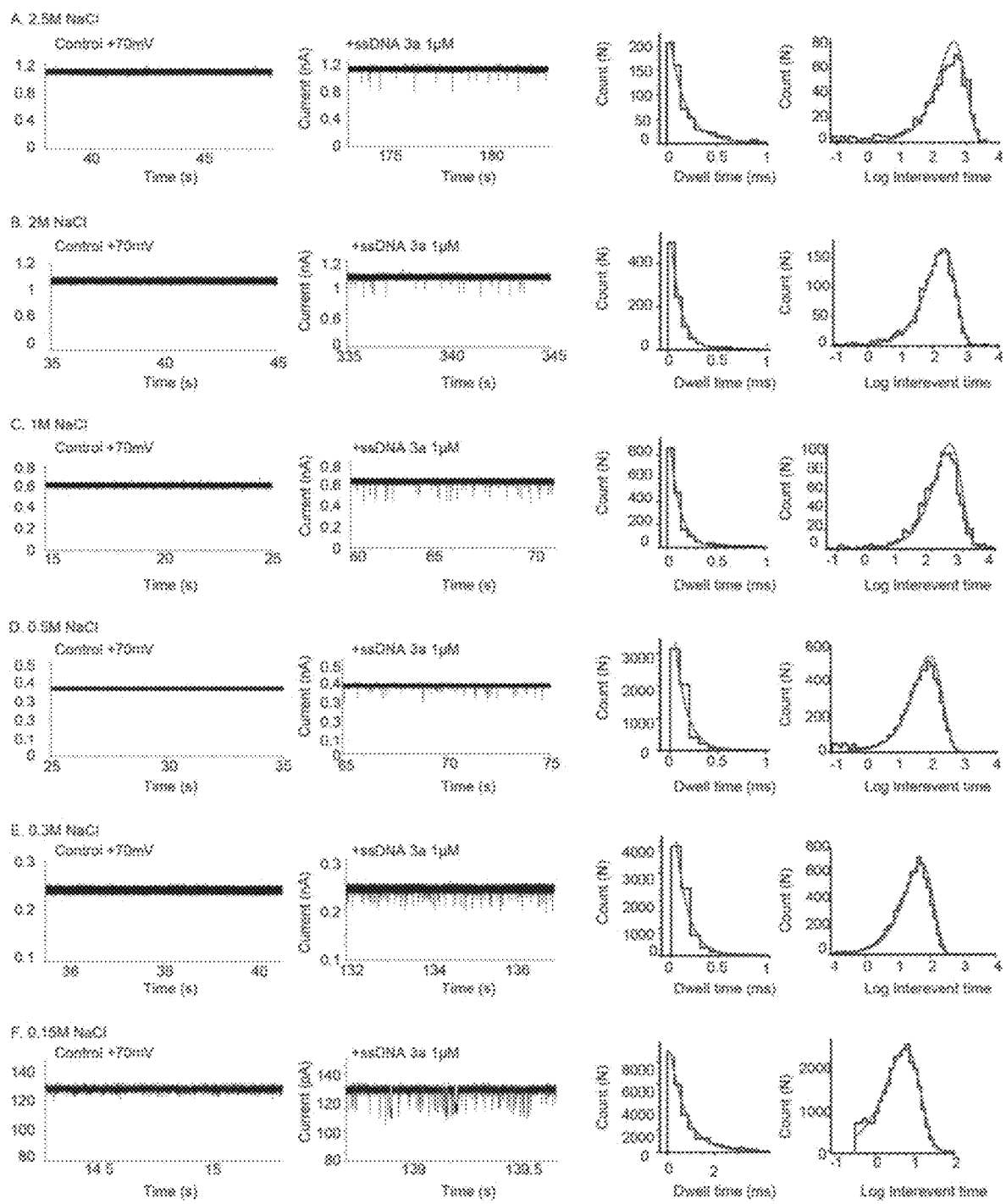
FIG. 7. Ionic strength dependency of ssDNA translocation. Panels A-F show data for different salt concentrations or ionic strengths. (Left side) Representative current trace showing the open pore current of ClyA-RR nanopores before and after adding 1 µM of a biotinylated ssDNA (1a, Table 3) to the cis side of the pore under +70 mV at different NaCl concentrations. The histograms on the right side represent the dwell times ($t_{OFF}$, left histogram) and inter-event time ($t_{ON}$, right histogram) of individual ssDNA translocation events. Individual toff and inter-event time ton events were collected individually by using the "single channel search" function in the Clampfit Software (Molecular devices) using a data acquisition threshold of 0.05 ms. The average DNA translocation dwell times $t_{OFF}$ were calculated from single exponential fits from cumulative histograms. The inter-event times $t_{ON}$ were calculated from exponential logarithmic probability fitting from histograms using logarithmic bins (base 10). The electrical recordings were carried out in 15 mM Tris-HCl. pH 7.5 at 22° C. Data were recorded by applying a 10-kHz low-pass Bessel filter and using a 20 µs (50 kHz) sampling rate. An additional 2-kHz low-pass Bessel filter was used for the data collected at 0.15 M NaCl solutions.
Figure 8:
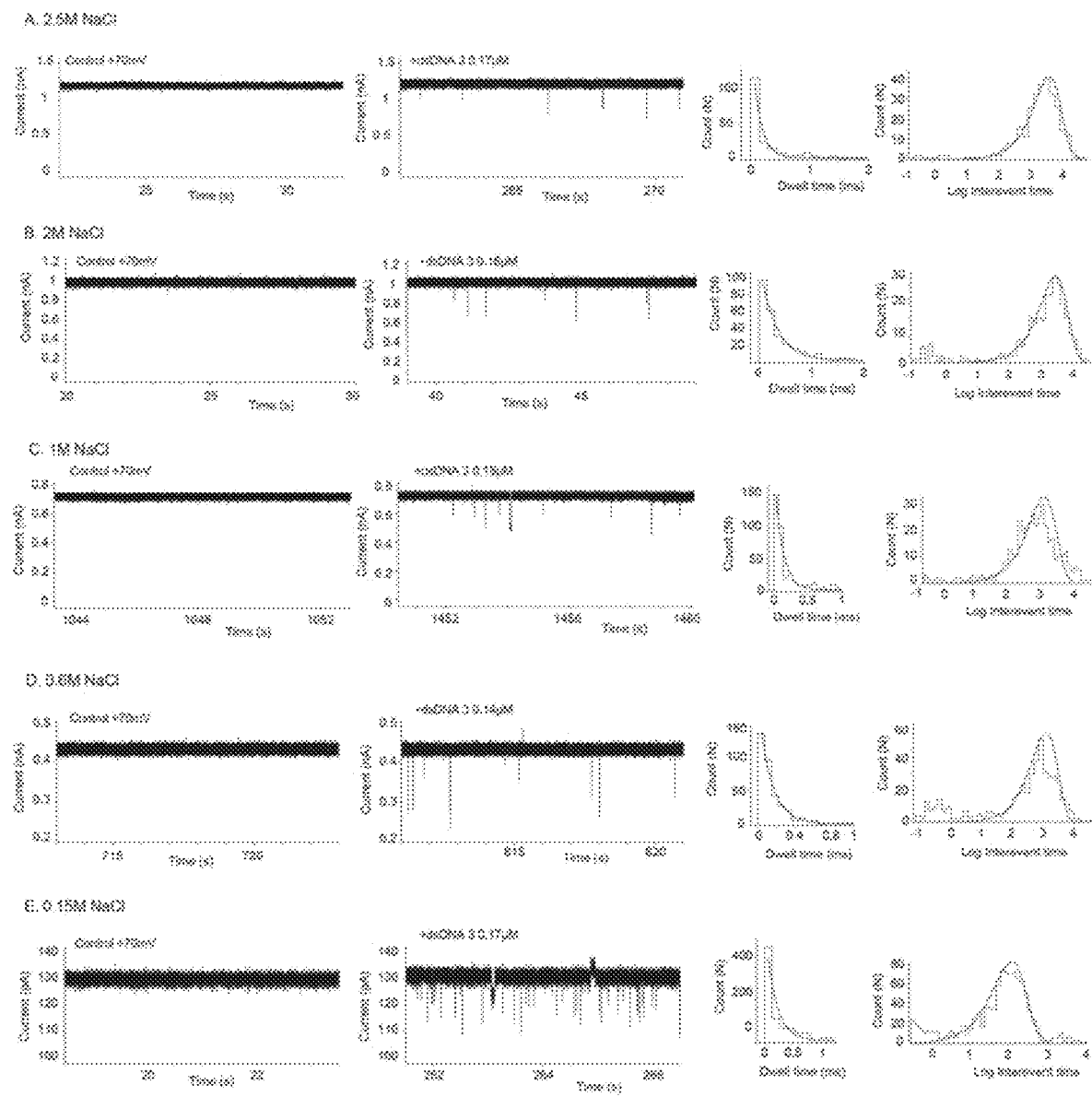
FIG. 8. Ionic strength dependency of dsDNA translocation. Panels A-E show data for different salt concentrations or ionic strengths. The current traces show the open pore current of ClyA-RR nanopores before (left) and after (right) the addition of 170 nM dsDNA (1, Table 3) added to the cis side of the pore under +70 mV and at indicated NaCl concentrations. The histograms on the right side represent the dwell times ($t_{OFF}$, left histogram) and inter-event time ($t_{ON}$, right histogram) of individual ssDNA translocation events. Individual tOFF and inter-event time tON events were collected individually by using the "single channel search" function in the Clampfit Software (Molecular devices) using a data acquisition threshold of 0.05 ms. The average DNA translocation dwell times $\tau_{off}$ were calculated from single exponential fits from cumulative histograms. The inter-event times $\tau_{on}$ were calculated from exponential logarithmic probability fitting from histograms using logarithmic bins (base 10).

In 150 mM NaCl and at +50 mV, both ssDNA and dsDNA/ssDNA threaded the nanopore ($I_{RES}$+50 92±0.02, and 0.84±0.07, respectively, N=3), but were ejected from the pore when the applied potential was reversed to −50 mV (FIG. 2, Panels A-B). The subsequent addition of the DNA:neutravidin stoppers to the trans solutions induced a permanent blockade at both potentials, indicating the assembly of a DNA rotaxane, and showing that both threads translocated the nanopore. At negative applied potentials the blocked ionic current was higher than the open pore current for both rotaxanes ($I_{RES}$−50=1.16±0.03 and 1.11±0.06, for ssDNA and dsDNA/ssDNA threads, respectively, N=3 independent nanopore experiments, FIG. 2, Panels, A-B; FIG. 12, Panels A-B). This effect was previously observed for the translocation of DNA through 10 nm solid-state nanopores at low ionic strengths and was explained by the accumulation of counterions inside the DNA blocked pore. By contrast, at positive applied potential the open pore current was higher than the blocked current (FIG. 1, Panels C-D and FIG. 2, Panels A-B; FIG. 12, Panels A-B), indicating that in this configuration neutravidin might interact with the lumen of the nanopore and that the accumulation of counterions on the DNA differs at the cis and trans sides of the nanopore. DNA Capture/Threading and Translocation Depends on the Ionic Strength of the Solution The capture rate $k_{on}$, which is the inverse of the inter-event time inverse of the inter-event time $\tau_{on}$ (Table 7, +70 mV, 1 µM DNA), increased with the Debye length of the solution ($\lambda_D$) for both ssDNA and dsDNA (FIG. 3, Panels B-C; FIG. 13, Panels A-B). However, while the dsDNA capture rate increased linearly with $\lambda_D$ (FIG. 13, Panel A), ssDNA capture rate increased exponentially with $\lambda_D$ (FIG. 13, Panel B). This indicate, therefore, different capture mechanisms for dsDNA and ssDNA. The frequency of dsDNA translocation, added on the cis side, increased linearly with the Debye length of the solution (+70 mV, FIGS. 3A, 7 and 8), indicating that the electrostatic interactions between the DNA and the nanopore are important for DNA entry and translocation. As reported before with solid-state nanopores, the residual current of DNA blocked nanopores increased as the ionic strength of the solution decreased (e.g., from 0.78±0.09 in 2.5 M NaCl to 0.92±0.02 in 150 mM NaCl). Interestingly, it was found a linear relationship between the IRES of the DNA blockades and the Debye length of the solution (FIG. 3, Panels B-C). For dsDNA in complex with Neutravidin the residual current was ~10% lower than during free DNA translocation, indicating that Neutravidin contributed to the overall ionic current of the blockade, most likely by interacting with the nanopore lumen.

The frequency of ssDNA translocation increased exponentially ($R^2=0.99$) rather than linearly ($R^2=0.78$) with the Debye length of the solution (FIG. 3, Panel C), indicating that additional factors other than the interaction between the engineered positive charges in the ClyA lumen and DNA play an important role for the nanopore entry and/or translocation. At 150 mM NaCl, ssDNA molecules in complex with Neutravidin showed permanent blockades to ClyA-RR nanopores, while at 1 M NaCl or higher, the blockades were transient (FIG. 3, Panel D, FIG. 10). A likely explanation for these data is that at high ionic strengths ssDNA entered and escaped the pore from the cis side. At ionic strengths ≥1 M the IRES values for ssDNA in the presence and absence of Neutravidin were the same (FIG. 3, Panel C; FIG. 10), indicating that under these conditions ssDNA might not fully thread the nanopore, preventing Neutravidin from interacting with the lumen of ClyA.

Unidirectional Entry of DNA into ClyA Nanopores

Figure 4:
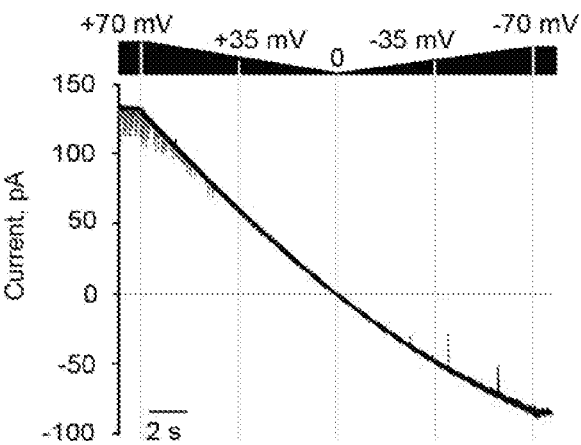
FIG. 4. Unidirectional DNA translocation through ClyA-RR nanopores. Panel A) In 150 mM NaCl solutions, the addition of 3 µM of dsDNA 1 to both the cis and trans sides of a ClyA-RR nanopores induced transient current blockades (grey vertical lines) only under positive applied potentials. Panel B) In 1.0 M NaCl solutions, the DNA blockades are observed under both applied potentials. DNA induced blockades are shown as grey vertical lines. The applied potential was automatically changed from +70 to −70 mV (Panel A) or from +100 to −100 mV (Panel B) in 21 seconds. The electrical recordings were carried out in 15 mM Tris HCl, pH 7.5, at 22° C. Data were recorded by applying a 2-kHz (Panel A) and 10-kHz (Panel B) low-pass Bessel filter and using a 100 µs (10 kHz, Panel A) and 50 kHz (Panel B) sampling rate.
Figure 4:
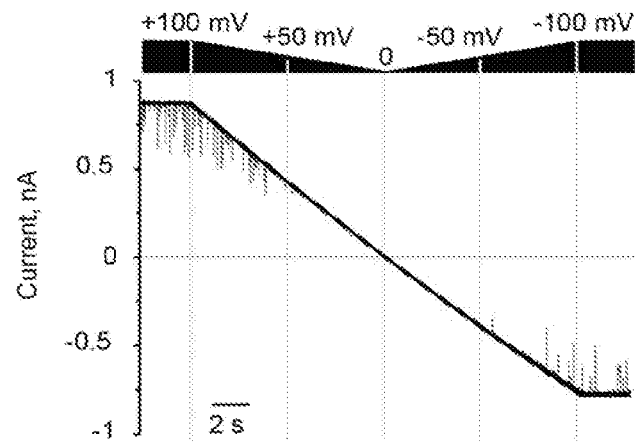

In 150 mM NaCl solutions and under negative applied potentials (up to −100 mV), the addition of 1 µM of ssDNA or dsDNA to the cis and trans compartments of ClyA-RR did not induced DNA blockades, indicating that DNA cannot enter the nanopore from the trans entrance of the nanopore (FIG. 4, Panel A). Under a positive applied bias, the current blockades appeared at potentials higher than ~+50 mV, suggesting the existence of a voltage threshold for the translocation of ssDNA from the cis side of the nanopore. The entry (FIG. 4, Panel B) and translocation (FIG. 9) of DNA from the trans compartment, however, was observed in 1 M NaCl solutions, indicating that the energy barrier that prevents the translocation from the trans compartment at 150 mM NaCl is electrostatic in nature.

To observe the entry of DNA from the trans compartment under physiological ionic strengths, the charges of the transmembrane region of ClyA-RR nanopores were remodeled (Table 5 and FIG. 10). It was found that the substitution of the negatively charged residue in the transmembrane region of the nanopore did not induce current blockades upon the addition of 1 µM of dsDNA 1 to the trans chamber under negatively applied potentials (FIG. 10), indicating a relatively large asymmetric barrier for the translocation of DNA from the cis and trans sides of the ClyA-RR nanopore under these conditions.

Discussion

Precise Nanopore Engineering Supports DNA Translocation at Physiological Ionic Strength In this Example, ClyA nanopores were engineered to allow the electrophoretic translocation of DNA at physiological ionic strengths. DNA translocation was observed when two sets of positive charges were introduced at the entry and in the midsection of the ClyA nanopore (FIG. 11, Panel A). Surprisingly, the trans entry of the nanopore, which provides the highest entropic and electrostatic barriers for DNA translocation (FIG. 11, Panels A-B), did not require modification. Further, despite extensive remodeling to the charge of the trans entry of ClyA (Tables 1-2), DNA translocation could be observed only when initiated from the wider cis entry of the nanopore. Moreover, the frequency of dsDNA translocation through ClyA-RR nanopores increased with the Debye length of the solution (FIG. 13, Panel A), showing that the favorable electrostatic interactions of dsDNA with the cis entry of ClyA-RR dominate over the unfavorable electrostatic repulsion of the DNA with the nanopore constriction. It should be noted that the stiffness of dsDNA does not change significantly over the range of ionic strength tested. Further, the increased electro-osmotic flow as the ionic strength is lowered cannot account for the increased frequency of DNA translocation because the electro-osmotic flow opposes DNA entry and translocation. These data indicate, therefore, that the cis lumen of the nanopore is important to initiate the translocation of DNA through the constriction of the nanopore.

A DNA molecule translocating through a nanopore is subjected to the electrical driving force, and the hydrodynamic viscous drag force arising from the electroosmotic flow (EOF) inside the nanopore that opposes the translocation of DNA. ClyA and most solid-state nanopores have a negative surface charge that is electrostatically balanced by a layer of cations in the immediate contact with the surface usually called electric double layers (EDL). Under the applied electric field, the movement of the ions in the EDLs induces the preferential translocation of the counterion, which in turn generate an EOF and makes the nanopore ion selective (e.g., ClyA-AS $P_{Na}/P_k=1.9$, Table 2). Due to the screening by the electrolyte, the EDL force decays in an exponential fashion over the diffuse layer. The range of this force is given by the Debye length and its strength by the surface potential. In narrow nanopores, especially in the regime of low salt concentration, the thickness of the EDLs including the diffuse layer might be comparable to the size of the nanopores, yielding overlapped EDLs. Under this regime a DNA molecule (diameter 2.2 nm) approaching such nanopores will experience a strong surface potential that for nanopores with negative surface charge will oppose the entry of DNA into the nanopore.

Mechanism of dsDNA and ssDNA Translocation Through ClyA Nanopores

Figure 5:
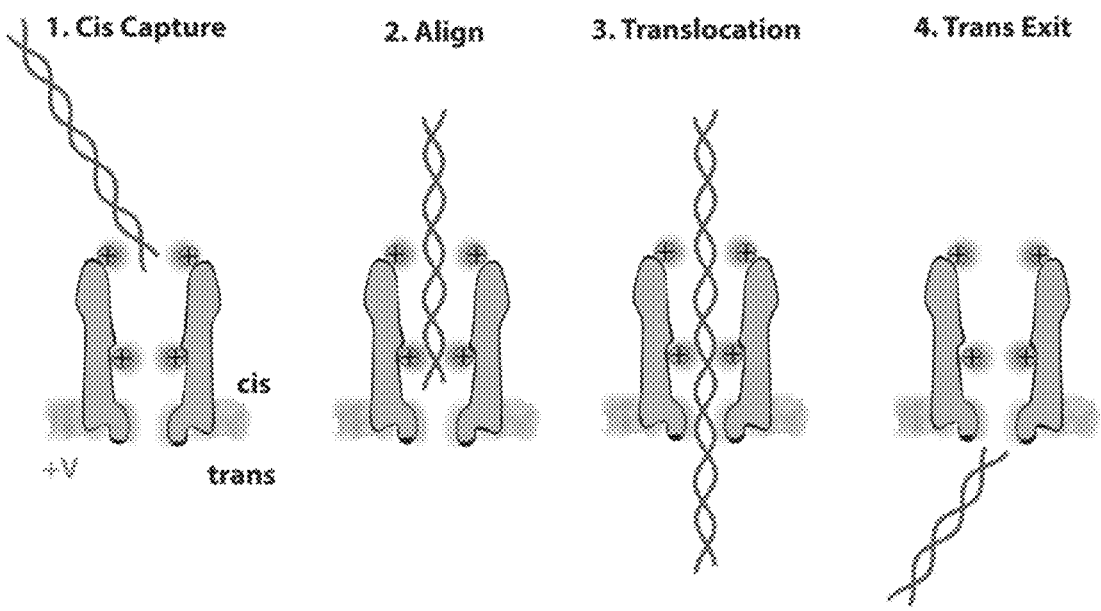
FIG. 5. Mechanism of dsDNA and ssDNA translocation through ClyA nanopores. Panel A) dsDNA translocation. (1) dsDNA initially interact with the charges at the cis entrance of the nanopore. (2) dsDNA penetrate inside the nanopore where it interacts with the second engineered charge. Both charges are important to align the DNA for productive translocation through the negatively charged trans constriction. (3) The dsDNA can then translocate and then (4) exit the pore. Panel B) (1) The additional charges at the cis entrance mediate the efficient capture of the DNA inside the nanopore. (2) ssDNA enters the cis lumen most likely as a coiled structure. (3) In order to translocate the trans constriction, ssDNA needs to uncoil to then recoil outside the nanopore. (4) DNA exit the nanopore. The DNA molecules and the nanopore are drawn in scale. Rg indicates the gyration radius of ssDNA. Under the experimental conditions, dsDNA is a rigid rod and ssDNA is a coiled structure with a gyration radius of ~6 nm.
Figure 5:
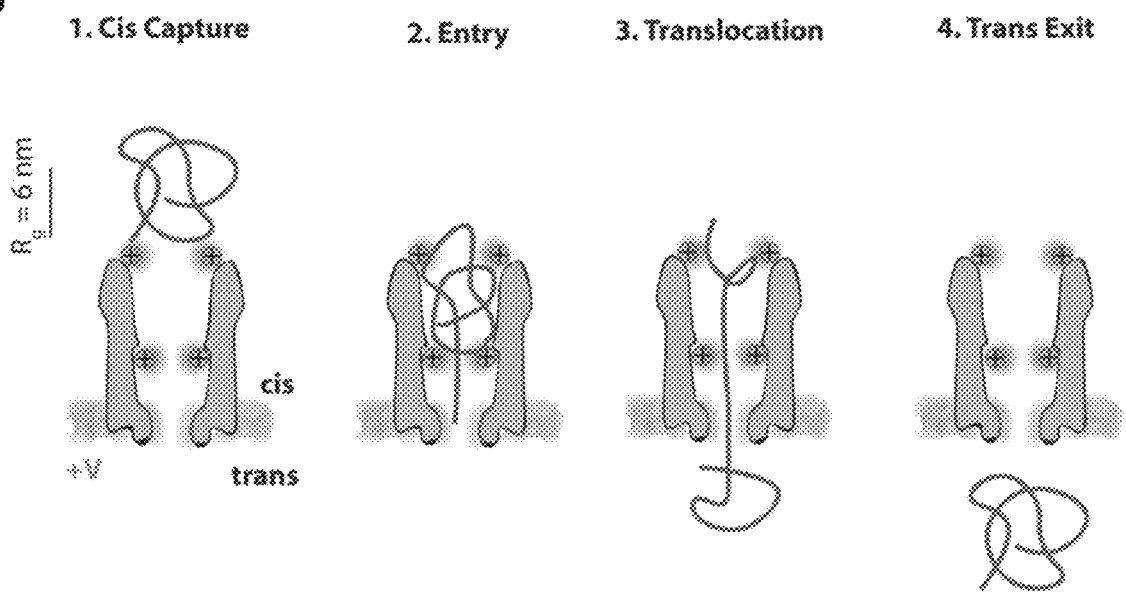

ClyA can be approximated by a cylindrical cis lumen (5.5 nm diameter and 10 nm length) followed by a smaller and negatively charged trans constriction (3.3 nm diameter and 3.0 nm length, FIG. 1), which is expected to oppose the main electrophoretic and entropic barrier for DNA translocation. Surprisingly, the translocation of DNA through ClyA nanopores was observed when a set of positive charges was added to the cis lumen of the nanopore (ClyA-RR); while the constriction of the nanopore did not require any modification. Despite extensive modification to the trans entrance of ClyA (Table 2), DNA translocation could be observed only when initiated from the wider cis side of the nanopore, suggesting that the cis lumen of the nanopore is important to initiate the translocation of DNA through the nanopore. The frequency of double stranded DNA translocation through ClyA-RR nanopores increased linearly with the Debye length of the solution (FIG. 3, Panel A), indicating that the electrostatic interactions of dsDNA with the engineered charges in ClyA-RR favor rather than oppose the translocation process. A model is proposed for where the translocation of dsDNA through the trans constriction at physiological ionic strengths is obtained when the dsDNA strand is pre-aligned by the cis lumen of the nanopore (FIG. 5, Panel A). In this view, the dsDNA initially interacts with the charges at the cis entry and then enter the lumen of the pore where it further interacts with the arginine residues at the mid-section of the nanopore (FIG. 1, Panel A). These electrostatic interactions "grab" the phosphate groups of DNA preventing the exit of the DNA back to the cis solution. In this configuration, the dsDNA is aligned to enter the trans constriction, where the electrophoretic force is the strongest, allowing the smooth translocation of DNA across the nanopore (FIG. 5, Panel A).

It was observed that the Debye length dependency of ssDNA blockades fitted well to a single exponential (FIG. 3, Panel A) rather than a linear function as observed for dsDNA, suggesting that additional factors influence the translocation of ssDNA compare to dsDNA. In the experiments, the DNA contour length, which is the total length of the DNA when it is stretched completely, is lower than the persistence length of dsDNA (~50 nm), indicating that the dsDNA molecules translocate as a rigid rod (FIG. 5, Panel A). By contrast, ssDNA has a coiled structure (persistence length ~1.5 nm) with a gyration radius, which is the average squared distance of any point in the polymer coil from its center of mass, of ~6 nm. Since the gyration radius is similar to the diameter of the cis entrance of the nanopore (FIG. 5, Panel B), ssDNA most likely enters the cis side of the nanopore as a partially coiled structure (FIG. 5, Panel B). As the ssDNA moves from the cis reservoir to the trans side, it must then gradually uncoil in order to navigate through the trans constriction of the nanopore and then recoil on the opposite side (FIG. 5, Panel B). This entropic uncoiling and recoiling force related to the conformational change of DNA in transition, which at high ionic strengths promotes the cis ejection of immobilized ssDNA from the nanopore against the applied potential (FIG. 3, Panel D), decreases with decreasing the ionic strength of the solution, augmenting the efficiency of DNA translocation as the ionic strength of the solution is reduced. It should be noted that the ion concentration and Debye length inside the DNA blocked nanopores are not known. Nonetheless, both correlate to the nanopore current, which in turn is linked to the concentration of bulk electrolyte (FIG. 3, Panels B and C).

Mechanism of DNA Translocation: dsDNA Capture is Diffusion-Limited and ssDNA Capture is Reaction-Limited The DNA translocation experiments at different salt concentrations showed two different capture mechanisms for dsDNA and ssDNA (FIG. 13, Panels A-B, and FIG. 14, Panels A-B, respectively). The behavior of dsDNA is consistent with a diffusion-limited capture process. This is because the dsDNA used in this work is shorter than its persistence length (150 bp) and behaves as a rigid uniformly charged rod. Within the capture radius (about 50 nm from the nanopore center for a $\lambda_D$ of 0.5 nm), the electric field attracts the DNA toward the pore and aligns it along the field lines so that it hits the pore entry with one end (FIG. 14, Panel A, i). Once inside the pore, the engineered charges interact with the DNA, preventing the retraction back to the cis solution (FIG. 14, Panel A,ii-iv). Therefore, the dynamics of DNA capture can be approximated by that of a diffusing particle in a purely attractive potential of electrophoretic origin. In this case, the electrophoretic mobility of the dsDNA is proportional to the Debye length of the solution and the corresponding drift-diffusion equation can be solved exactly, which is further described in detail below. By approximating the geometry of the ClyA nanopore with a cylinder of length l=13 nm and a capture diameter d=6 nm (FIG. 11, Panel A), the capture frequency can be estimated by the following:

$$k_{on} \sim 14 \lambda_D (s\ nm\ \mu M)^{-1}$$

This is in remarkably good agreement with the experimental data for (at high salt concentrations, FIG. 13, Panel A). This is striking because no fitting parameters are used. However, some care should be taken in this comparison, as the choice of the pore parameters is to some extent arbitrary since ClyA's geometry deviates significantly from a perfect cylinder. At low salt concentrations (0.15 M NaCl, $\lambda_D$=0.8 nm), the capture rate is higher than predicted by the equation above (FIG. 13, Panel A). Likely, the positive charges at the ClyA-RR entry, which are not taken into account in the model, speed up the capture at low salt concentrations, while at higher salt concentrations, these charges are more effectively screened.

For ssDNA, the relation between $k_{on}$ and $\lambda_D$ is exponential, which is consistent with a barrier crossing (reaction-limited process). In solution, the ssDNA assumes a coiled conformation while it is pulled toward the nanopore by the electrophoretic force as DNA approaches the nanopore (FIG. 14, Panel B,i). In the vicinity of the entry of the pore, however, a successful translocation event can only take place if one end of the strand faces the pore entry (FIG. 14, Panel B,ii) and if the ssDNA is uncoiled (FIG. 14, Panel B,iii,iv). This additional repulsive force of entropic origin effectively results in an energy barrier that must be crossed prior to translocation. The theory of such barrier-limited translocation has been discussed and on general grounds, the capture rate is given by: $k_{on} = \omega c^{-\Delta F_b/k_B T}$ Here, $\Delta F_b$ is the barrier height and $\omega$ is a characteristic attempt rate for barrier crossing. The exponential factor gives the probability of a successful crossing event. Estimating $\Delta F_b$ from model inputs can be accomplished; it was shown that the probability of successful translocation contains a term proportional to the electrophoretic mobility, which in turn is proportional to $\lambda_D$. This would explain the exponential dependence of $k_{on}$ on $\lambda_D$ (FIG. 13, Panel B). It should be noticed that while $k_{on}$ is obtained from the inverse inter-event time, not all measured current blockades necessarily describe a translocation event. Part of these blockades may be due to the entry of a DNA strand followed by a retraction back to the cis side (FIG. 14, Panel B, iii to i). Nevertheless, the formation of rotaxanes shows that at least some molecules successfully translocate. In any case, the argument leading to an exponential dependence of $k_{on}$ on $\lambda_D$ remains valid.

Biological Significance

Interestingly, the modifications that allowed the translocation of DNA through ClyA nanopores are also observed in proteins which biological function is to slide along DNA. In bacteriophages, DNA is transferred into the procapsid by packing proteins that align and push the DNA through portal proteins that have similar dimension, stoichiometry, internal surface charge, and internal constructions size similar to that of ClyA. A negative internal surface charge appears to be important for the smooth translocation of DNA across the portal proteins, as it is observed in other proteins that encircle and slide along DNA such as β-clamp proteins. Portal proteins and β-clamp proteins also have positively charged rings that have been proposed to play a direct role in genomic DNA packaging by interacting with the negatively charged phosphate backbone of the translocating DNA. The electrophoretic translocation of DNA through ClyA nanopores could be observed when two rings of positive charged residues are introduced at the cis entrance and mid-section of the nanopore, aligning the DNA for the passage through the narrow and electronegative constriction. In the absence of such interactions, that is, during the threading from the trans side, DNA translocation could not be observed. The results presented herein indicate, therefore, that in connector proteins such rings of positive charges might be important to initiate the ejection of the DNA out of the capsid into the infected cell.

Presented in this Example is an engineered ClyA dodecameric nanopore, ClyA-RR, upon introduction of two rings of positive charges, to translocate dsDNA and ssDNA at physiological ionic strengths. ClyA-RR can be used to study protein-DNA interactions at the single-molecule level and can be employed in DNA mapping and sequencing applications, where an enzyme controls the translocation of the nucleic acid through the nanopore. It was found that the introduction of rings of positive charges, attractive interactions, at the wider entry (the cis side) of the nanopore is important to induce DNA translocation through the narrow and negatively charged trans constriction. Surprisingly, the constriction itself did not require modifications. These results indicate that attractive interactions at the entry and in the middle of the nanopore are important to "grab" and orient the DNA for effective electrophoretic-driven sliding through the narrow and negatively charged trans constriction. Interestingly, the charge distribution in ClyA-RR is mirrored in viral portal proteins, indicating that the precise engineering of biological nanopores is important for the efficient packing and ejection of DNA in and out the viral capsid. Further, the linear and exponential ionic strength dependencies of the frequency of dsDNA and ssDNA translocations, respectively, indicate a likely mechanism where the dsDNA capture follows a diffusion-limited process, while the ssDNA capture a reaction-limited process. It was also showed that ssDNA enters the nanopore as a coiled structure that needs to be uncoiled in order to translocate through the constriction of the nanopore. These finding can be used to help the engineering of solid-state nanopores. For example, a nano-scale chamber with a favorable surface charge and a diameter similar to the gyration radius of DNA placed above the nanopore should favor the translocation of DNA, especially at low ionic strengths. In addition, it was found that the modifications to the ClyA nanopore that allow DNA translocation are mirrored in viral portal proteins, indicating that the precise engineering of biological nanopores is important for the efficient packing and ejection of DNA in and out the viral capsid.

Exemplary Materials and Methods

DNA was purchased from Integrated DNA Technologies (IDT). Neutravidin was acquired from Thermo Fisher and 1,2-diphytanoyl-sn-glycero-3-phosphocholine from Avanti Polar Lipids. β-Dodecyl maltoside (DDM) was purchased from GLYCON Biochemicals GmbH. Enzymes were bought from Fermentas and all other materials from Sigma, unless otherwise specified.

Protein purification. Single-point mutations to the ClyA-AS gene were performed by using the "mega primer" method as described in Soskine et al., *J. Am. Chem. Soc.* (2013) 135: 13456-13463 and Miyazaki et al., Methods Enzymol. (2011) 498: 399-406. ClyA was expressed in E. cloni® EXPRESS BL21 (DE3) cells by using a pT7 plasmid. Monomers were purified by using Ni-NTA affinity chromatography and oligomerized in the presence of 0.5% β-dodecyl maltoside (GLYCON Biochemicals GmbH) as described in Waduge et al., *ACS Nano* (2015) 9: 7352-7359. Monomers (containing a C-terminal oligo-histidine tag) were expressed in *E. coli* BL21 cells and the soluble fraction purified using Ni-NTA affinity buffer (150 mM NaCl, 15 mM Tris HCl, pH 7.5, 0.2% DDM and 1 mM EDTA) and stored at 4° C.

DNA preparation. dsDNA 1 was prepared by first mixing equimolar concentrations of 1a and 1b (Table 3). The mix was brought to 95° C. and the temperature stepped down at regular intervals. The DNA was purified from the excess of ssDNA with affinity chromatography using a biotin-binding column containing monomeric avidin immobilized on agarose beads (Thermo Scientific Pierce). The ds DNA was then eluted from the column according to the manufacturer's protocol. The elution fraction was concentrated and further purified using a PCR quick purification kit (QIAGEN). Typically, a DNA concentration of 0.2 µg/mL was obtained. 1a/1c duplex was annealed as explained for 1 but not purified.

Ion permeability. I-V curves under asymmetric conditions (Table 6) were collected by adding ClyA to the cis chamber under symmetric conditions (150 mM NaCl, 15 mM Tris-HCl pH 7.5 in both cis and trans solutions). The electrodes were then balanced, and the electrolyte concentration in cis was increased up to 1 M by adding aliquots of 5 M NaCl stock solutions to the cis compartment. The volume of the trans chamber was adjusted by adding the same volume added to the cis side using the same buffer of the cis solution (150 mM NaCl).

Permeability ratios ($P_{Na+}/P_{Cl-}$, Table 4) were calculated using the Goldman-Hodgkin-Katz equation (below) using the measured reverse potential (Vr) values, which were extrapolated from the I-V curves.

$$P_{Na^+}/P_{Cl^-} = \frac{[a_{Cl^-}]_{trans} - [a_{Cl^-}]_{cis}e^{V_rF/RT}}{[a_{Na^+}]_{trans}e^{V_rF/RT} - [a_{Na^+}]_{cis}}$$

R is the universal gas constant (8.314 J K$^{-1}$ mol$^{-1}$), T the temperature in Kelvin, F the Faraday's constant (96 485 C mol$^{-1}$), $P_{Na+}$ and $P_{Cl-}$ are the relative membrane permeability for the ions Na$^+$ or Cl$^-$, and $\alpha_{Na+}$ and $\alpha_{Cl-}$ are their respective activities. The cis chamber was the ground. Ag/AgCl electrodes with 2.5% agarose bridges containing 2.5 M NaCl were used to perform all of the experiments.

Electrical Recordings. Ionic currents were measured by recording from planar bilayers formed from diphytanoyl-sn-glycero-3-phosphocholine (Avanti Polar Lipids, Alabaster, Ala.). Currents were measured with Ag/AgCl electrodes submerged in agar bridges (3% w/v low-melt agarose in 2.5 M NaCl buffer) using a patch-clamp amplifier (Axopatch 200B, Axon Instruments, Foster City, Calif.) as described in Ho et al., *Sci. Adv.* (2015) 1, e1500905; and Maglia et al., *Methods Enzymol.* (2010) 475: 591-623. Single channels were characterized by measuring the current versus applied voltage relationship (I-V curve, the potential was applied in 10 mV steps from −100 to +100 mV in 21s , FIGS. 6, 10 and Table 5). In 0.15 M NaCl, ionic currents were recorded by applying a 2 kHz low-pass Bessel filter and using a 10 kHz sampling rate. At higher salt concentrations, ionic currents were sampled at 50 kHz and the low-pass Bessel filter was set at 10 kHz. Current traces at 0.3 and 0.5 M NaCl were filtered post-acquisition with a 4 kHz Bessel digital filter (FIGS. 16, 17). The use of different filtering frequencies influences the overall number of detected events. For example, applying a 2 kHz digital Gaussian filter to a trace sampled at 50 kHz while applying a 10 kHz Bessel filter increases the inter-event time by about 50% (from 221 to 311 ms, 0.17 µM dsDNA, 1 M NaCl, average dwell time of 0.12 ms). Therefore, to test the effect of excessive filtering on the Debye length dependence of the DNA capture frequency, the data described in FIG. 13, Panel A were plotted after applying a 1 kHz Gaussian filter to all current traces (FIG. 18). It was found that the ssDNA and dsDNA blockades fitted well to an exponential and a linear regression, respectively (FIG. 18).

Data analysis. Current blockade events were collected individually by using the "single channel search" function of the Clampfit software (Molecular Devices) using a data acquisition threshold of 0.05 ms. Open and blocked pore current were obtained were calculated from Gaussian fitting to all-point histograms. Residual currents were calculated by dividing the blocked pore current values for the open pore current values. The DNA translocation dwell times ($\tau_{off}$) values were calculated from a single exponential fit from event histograms of DNA blockade dwell-times, while ($\tau_{on}$) values were calculated using an exponential logarithmic probability fit from logarithmic histograms of the inter-event times (FIG. 13, Table 7, and FIGS. 16, 17). The errors indicate the standard deviation from the average from at least three independent nanopore experiments, the number of which is indicated by N.

Additional Iinformation About Preparation of the Modified ClyA Nanopore Subunit Polypeptide According to One Embodiment Described Herein Single point mutations to the ClyA-AS gene were performed by using the "mega primer" method. Typically, two PCR cycles were performed to prepare a new DNA construct: In the first PCR reaction the plasmid DNA was amplified with two primers: the forward primer was a oligonucleotide 20-30 bases in length that carried the base substitution, the reverse primer was either the T7 promoter or T7 terminator. For mutations at the transmembrane region the reverse primer was a 25 mer oligo complementary to a stretch in the middle of protein sequence (Table 3). The PCR product containing the mega primers (200-300 bp), was loaded into an agarose gel (2% agarose/TAE and crystal violet), the megaprimer cut out and purified using a PCR quick purification kit (QIAGEN). 5 µL of purified mega primers were loaded on 2% agarose/TAE gel to check for purity and 5-10 µL of the megaprimer were employed for a $2^{nd}$ PCR reaction. The $2^{nd}$ PCR product was then first digested with Dpnl (1-2 h, 37° C., fast digest DpnI, Fermenthas) to eliminate the ClyA-AS template DNA and then ~1 µL used for transformation with electrocompetent cells E. cloni® EXPRESS BL21 (DE3) (maker).

Additional Information About DNA Preparation dsDNA 1 was formed by incubating 1a, 3'-biotinylated ssDNA molecule (Table 3), with a 20% excess of complementary ssDNA 1b (Table 3). The temperature was brought to 95° C. for 1 min and then decreased stepwise to room temperature. At around the estimated annealing temperature of 70° C., the temperature was decreased in 2° C. steps to 21° C. Each step lasted for 1 minute. The DNA was then purified from the excess of ssDNA with affinity chromatography using a biotin-binding column containing monomeric avidin immobilized on agarose beads (Thermo Scientific Pierce). The dsDNA was then eluted with Biotin Blocking/ Elution Buffer according to the manufacturer protocol. The elution fraction was concentrated and further purified using a PCR quick purification kit (QIAGEN). Typically, a DNA concentration of 0.2 µg/mL was obtained. The size and purity of the dsDNA was checked by using a 2% agarose gel in TAE buffer and quantified spectroscopically. The purified dsDNA was stored at −20° C. in the presence of 1 mM EDTA. 1a:1c was formed by incubating a 3'-biotinylated ssDNA molecule (1a, Table 3) with equal molar concentration of a 1c. The temperature was brought to 95° C. for 1 minute and then decreased stepwise to room temperature. At around the estimated annealing temperature 70° C., the temperature was decreased in 2° C. steps, each held for 1 minute.

Additional Information About Electrical Recordings and Data Analysis

Artificial planar lipid bilayers were prepared as described above. If not otherwise specified, the signal was collected at a sampling rate of 50 kHz after processing with a 10-kHz Bessel filter. The lipid bilayer was formed by pretreating a small aperture (~100 µm) on a Teflon film (Goodfellow, UK) with 1-2 µl of a 10% solution of 1,2-diphytanoylsn-glycero-3-phosphocholine in pentane. The electrical potential was applied by using Ag/AgCl electrodes submerged in agar bridges (3% w/v low melt agarose in 2.5 M NaCl buffer). The applied potential refers to the potential of the working electrode connected to the trans compartment of the apparatus. ClyA nanopore solutions (0.01-0.1 ng/mL) were added to the cis compartment, which was connected to the ground electrode. After the insertion of a single pore, excess protein was removed by several cycles of perfusion. Electrical recordings were carried out in 0.15-2.5 M NaCl, 15 mM Tris HCl, pH 8.0, at 22° C. In 0.15 M NaCl data were recorded by applying a 2-kHz low-pass Bessel filter and using a 10 kHz sampling rate. While at higher salt concentration data were sampled at 50 kHz and the low-pass Bessel filter was set at 10 kHz. Current traces at 0.3 and 0.5 M NaCl were filtered post-acquisition with a 4-kHz Bessel digital filter. Current blockade events were collected individually by using the "single channel search" function of the Clampfit software (Molecular devices) using a data acquisition threshold of 0.05 ms. $I_O$ and $I_B$ values were calculated from Gaussian fitting to all-point histograms of the open and blocked pore currents, respectively. The DNA translocation dwell time $\tau_{off}$ was calculated by a single exponential standard fits from an event histogram of the block pore current events ($\tau_{off}$). The inter-event time $\tau_{on}$ was calculated by using an exponential logarithmic probability fit from the logarithmic histogram of the inter-event times ($t_{on}$) between block pore current events. The errors indicate the standard deviation from the average from at least three independent repeats, the number of which is indicated by "n."

Pores inserted from the cis chamber showed higher conductance at positive applied potential, helping to assess the orientation of the inserted channel. Single channels were characterized by measuring the current versus applied voltage relationship, (I-V curve, the potential was applied in 10 mV steps from −100 to +100 mV in 21 seconds). The pore rectification was obtained from the ratio of the open pore current at +100 mV and that at −100 mV ($I_{0+100\ mV}/I_{0-100\ mV}$). The propensity for gating of the nanopores was assessed by the continuous measurement of the open pores current at a given applied potential. $V_{MAX}$ was then given by the applied potential at which no gating events were observed within a 30 second timespan. Spontaneous reversible gating of the ionic current were observed at applied voltages higher than $V_{MAX}$. DNA entry and translocation through the pore was tested by adding 1 µM of 3' end biotinylated ssDNA 1 a followed by the addition of the complementary ssDNA 1b (Table 3) and then neutravidin (1.2 µM, monomer) to the cis chamber under an applied potential equal to $V_{MAX}$.

Additional Information About Ionic Permeability

Permeability ratios for ClyA nanopores were calculated by measurement of the reversal potential in asymmetric salt condition: 150 mM NaCl trans, 1 M NaCl cis. The protein nanopores were added to the cis chamber and a single channel was first characterized in symmetric condition (150 mM NaCl, 15 mM Tris HCl pH 7.5 in both cis and trans solutions). After the electrodes were balanced, the electrolyte concentration in cis was increased up to 1 M, by adding aliquots of 5 M NaCl stock solutions to the cis compartment. The volume of the trans chamber was adjusted by adding the same volume added to the cis side using the same buffer of the cis solution (150 mM NaCl). The reversal potential ($V_r$, Table 3), which is the electrical potential used to obtain a zero current, was obtained by current-voltage (IV) curve (Table 6). Ion selectivities ($P_{Na+}/P_{Cl}$) were calculated from the $V_r$ by using the Goldman-Hodgkin-Kats (GHK) equation. According both to the GHK equation positive value for Vr observed for the ClyA nanopores show a preferential movement of the cations through the pore, indicating that the pores are cationic selective channels. The cis chamber was at ground and Ag/AgCl electrodes with 2.5% agarose bridges containing 2.5 M NaCl were used to perform all the experiments.

$$P_{Na^+}/P_{Cl^-} = \frac{[a_{Cl^-}]_{trans} - [a_{Cl^-}]_{cis}e^{V_rF/RT}}{[a_{Na^+}]_{trans}e^{V_rF/RT} - [a_{Na^+}]_{cis}}$$

where $V_r$ is the membrane potential, R the universal gas constant (8.314 J·K−1·mol−1), T the temperature in Kelvin F the Faraday's constant (96485 C·mol−1), $P_x$ the relative membrane permeability for Na$^+$ and Cl$^-$, $[a_x]_{cis}$ the activity of Na+ and Cl$^-$ in the cis compartment, $[a_x]_{trans}$ the concentration of Na+ and Cl$^-$ in the trans compartment, and $a_x$ the activity of Na+ and Cl$^-$ (J. F. Zemaitis, Handbook of aqueous electrolyte thermodynamics: theory and application, 1986; Ludwig Molecular Microbiology 1999; Li-Qun Gu PNAS 2000; Petr G. Merzlyak Biophysics 2005).

Details are presented on the derivation of Eqs. (1) and (2), describing the capture rates of dsDNA and ssDNA, respectively.

dsDNA Capture

The approach relates to one developed by Grosberg and Rabin. The ClyA nanopore-membrane is described as a planar dielectric surface of thickness l with a cylindrical hole of diameter d. Characteristic distances for a ClyA pore are l=13 nm and d=6 nm. Using $\Delta V$ to represent the potential difference between the cis and trans side of the membrane, it can be shown that the electric potential in the cis side is given by:

$$V(r) = \frac{d^2}{8lr}\Delta V \quad (1)$$

which decays as 1r/far from the pore at the cis side (by convention the potential at the electrode in the cis side was set to zero). The origin of the coordinates (r=0 nm) is the middle of the pore (FIG. 19).

The dsDNA is approximated as a charged point particle performing a diffusive motion with diffusion constant D and with an electrophoretic drift characterized by an electrophoretic mobility $\mu$. The resulting drift-diffusion equation in radial coordinates for the dsDNA concentration c(r,t) is given by:

$$\frac{\partial c}{\partial t} = \frac{1}{r^2}\frac{\partial}{\partial r}\left[Dr^2\frac{\partial c}{\partial r} - \mu r^2 c\frac{\partial V}{\partial r}\right] \quad (2)$$

where the minus sign in front of the electrophoretic current is because the DNA is negatively charged. In this convention the mobility coefficient positive $\mu$>0 is kept, hence the drift velocity due to an applied electric field is v=−$\mu$E. Note that the Einstein relation does not hold for this system (i.e., D≠$\mu$kBT), hence one cannot simply relate D and $\mu$.

The stationary solution ($\partial c\partial t/=0$) of Eq. (2) is:

$$c(r) = c_0 \frac{1 - e^{-r^*(1/R-1/r)}}{1 - e^{-r^*/R}} \quad (3)$$

where the boundary conditions are: $c(R)\rightarrow c_0$ at infinity and c(R)=0 with R a microscopic distance of the order of the pore size. The distance r* is defined as:

$$r^* = \frac{\mu d^2 \Delta V}{8Dl} \quad (4)$$

which allows us to rewrite the electrophoretic potential (1) as:

$$V(r) = \frac{D}{\mu}\frac{r^*}{r} \quad (5)$$

From the solution (3) and the previous relation one obtains the radial particle current density:

$$j(r) = -D\frac{\partial c}{\partial r} + \mu c\frac{\partial V}{\partial r} = \frac{Dr^*c_0}{r^2}\frac{1}{1-e^{-r^*/R}} \quad (6)$$

And the rate is obtained from integrating the current density over a half spherical shell of radius r (accounting for the surface available on the cis side):

$$k_{on} = 2\pi r^2 j(r) = \frac{2\pi Dr^*c_0}{1-e^{-r^*/R}} \approx 2\pi Dr^*c_0 \quad (7)$$

where the approximation r*>>R, validity was checked later. The final result formally resembles the Smoluchowski diffusion-limited reaction rate for a diffusive particle in absence of an external potential. Here r* can be interpreted as the distance at which the dsDNA is irreversibly captured by the pore. This capture radius increases at higher applied potential or for increased electrophoretic mobility (4). Combining (4) and (7) one obtains:

$$k_{on} = \frac{\pi d^2 \Delta V c_0 \mu}{4l} \quad (8)$$

Note that D cancels out from the previous equation since r* is inversely proportional to D.

To proceed further $\mu$ was estimated. The total charge on a dsDNA molecule with length L is Q=−2$\alpha$eLa/where a=0.34 nm is the distance between two bases and $\alpha$<1 is a numerical coefficient which reflects the fact that not all of the phosphate groups are ionized.

Approximating the DNA as a cylinder of surface area A, the drag force was estimated as ($\eta A\lambda_D$/)v where $\eta$=10$^{-3}$ kg m$^{-1}$ s$^{-2}$ is the water viscosity and $\lambda_D$ the Debye length. Using the definition v=−$\mu$E one gets:

$$\mu = \frac{2\alpha\lambda_D}{\eta\pi ab} \quad (9)$$

where b=2 nm is the double helix diameter. An alternative derivation of this equation, based on the calculation of the ζ-potential is given by Grosberg and Rabin. Now combining Eqs. (7) and (9) and using the numerical values relevant for the experiments ($\Delta V=+70$ mV, $c_0=1$ μM) and setting $\alpha=1$, i.e., full ionization, it is obtained:

$$k_{on}=14\lambda_D(\text{snm μM})^{-1} \quad (10)$$

which is the equation (1) reported above.

The capture radius r* was finally computed. For this purpose the diffusion coefficient is estimated using Stokes' law:

$$D = \frac{k_B T}{6\eta\pi R_H} \quad (11)$$

where $R_H$ is the hydrodynamic radius. Considering the dsDNA as a cylinder of radius 1 nm and length 34 nm (100bp), using the expression given by Hansen et al. (*J. Chem. Phys.* (2004) 121: 9111-9115), it was estimated that $R_H \approx 6$ nm. Combining (11) and (4):

$$r^* = \frac{3d^2}{2l} \frac{\lambda_D R_H}{ab} \frac{e\Delta V}{k_B T} \approx 50 \text{ nm} \quad (12)$$

where $\lambda_D=0.5$ nm and $k_B T \approx 25$ meV. The capture radius is two orders of magnitude larger than the Debye length and much larger than the pore radius, hence the approximation used in Eq. (7) is justified.

ssDNA Capture

The discussion of ssDNA capture is inspired by the approach developed in by Rowghanian et al. (*Phys. Rev. E* (2013) 87: 042723) for a barrier-limited process. This case is much more complex than the diffusion-limited case and the theory less established. The model is based on a drift-diffusion equation using a single "reaction" coordinate r, which is the distance of one end from the pore entry. Sufficiently far from the pore the ssDNA is subject only to an attractive electrophoretic force as described by equation (1). In the vicinity of the pore at a distance $\gtrsim R_g$, where $R_g$ is the equilibrium radius of gyration there is an additional repulsive force of entropic origin: the ssDNA coil reduces its configurational entropy when the end is forced to get closer to the pore entry. If the strand is sufficiently long, the entropic repulsion dominates over the electrostatic attraction resulting in a barrier (FIG. 19).

Indicating with U(r) the entropic potential the following radial current density:

$$j(r) = -D\frac{\partial c}{\partial r} + \mu c \frac{\partial V}{\partial r} - \tilde{\mu}c\frac{\partial U}{\partial r} \quad (13)$$

Where $\mu$ is the electrophoretic mobility, while $\tilde{\mu}$ is the mobility associated to a generic non-electric force, in this case the entropic repulsion. While $\mu$ does not fulfill the Einstein relation ($D \neq \mu k_B T$), the generic mobility $\tilde{\mu}$ does satisfy this relation ($\tilde{\mu}=D/k_B T$). The particle current in Eq.(13) can be rewritten as follows:

$$j(r) = -D\left(\frac{\partial c}{\partial r} - \frac{c}{k_B T}\frac{\partial F_b}{\partial t}\right) \quad (14)$$

Where:

$$F_b(r) = U(r) - \frac{\mu}{\tilde{\mu}}V(r) \quad (15)$$

Hence the problem consists in a diffusive motion of a particle in a potential $F_b$. Because of the violation of the Einstein relation, this potential contains also kinetic parameters as the electrophoretic mobility μ and the solvent viscosity η from $\mu \sim \eta^{-1}$. The potential has a minimum close to distance $R_g$ and a maximum close to the pore entry defining a barrier height: $\Delta F_b \equiv F_b^{max} - F_b^{min}$. According to Kramers' theory the capture rate $k_{on}$ depends exponentially on the barrier height:

$$k_{on}=\omega e^{-\Delta F_b/k_B T} \quad (16)$$

The barrier can be lowered by increasing the applied voltage $\Delta V$ so to strengthen the electrostatic attraction towards the pore. Eq. (15) implies that a similar effect can be obtained by increasing μ, the electrophoretic mobility of the ssDNA. One obvious way to modify μ is through a change of the ionic strength of the solution as this modifies the Debye length. As shown in Eq. (9), the electrophoretic mobility is proportional to $\lambda_D$. Note that the salt concentration has also an effect on the ssDNA persistence length and thus on the entropic contribution to the barrier U(r), however this effect is expected to be weaker. The main effect of a change in the salt concentration on the barrier height is expected to contain a term linear in $\lambda_D$:

$$\Delta F_b = a - b\lambda_D \quad (17)$$

With a, b>0 which, together with (15) explains the exponential growth of $k_{on}$ on $\lambda_D$ observed in the experiments.

TABLE 2

Pore engineering DNA translocation from the trans side. Each data point is the average of at least three experiments and the error is the standard deviation. Experiments were carried out in 0.15M NaCl, 15 mM Tris HCl, pH 7.5 solutions. The activity of the nanopores were tested by adding 0.01-0.1 ng oligomeric protein to the trans chamber. A negative activity indicates that no channel insertions were observed. $V_G$ represents the maximum applied voltage at which no gating events were observed within 30 s. DNA capture indicates that only transient current blockades were observed upon the addition of biotinylated dsDNA in complex with neutravidin. DNA translocation indicates that a dsDNA rotaxane could be formed.

| Pore variants | $I_O$ + 100 mV $I_O$100 Mv (pA) | Rectification ratio | $V_G$, (mV) | DNA Capture | DNA Translocation |
|---|---|---|---|---|---|
| ClyA-RR-E7S | +186 ± 2 −110 ± 2 | 1.7 ± 0.0 | −70 | + | − |
| ClyA-RR-E11S | +214 ± 27 −124 ± 14 | 1.7 ± 0.3 | −100 | − | − |
| ClyA-RR-D21S | +193 ± 9 −113 ± 9 | 1.7 ± 0.2 | −70 | − | − |
| ClyA-RR-D21K | +149 ± 0 −112 ± 0 | 1.3 ± 0.0 | −50 | − | − |
| ClyA-RR-D32N | +196 ± 5 −104 ± 5 | 1.9 ± 0.1 | −150 | − | − |
| ClyA-RR-E7S-D32N | +182 ± 4 −104 ± 6 | 1.8 ± 0.1 | −70 | + | − |
| ClyA-RR-E7S-D21S | +182 ± 5 −121 ± 3 | 1.5 ± 0.1 | −70 | + | − |
| ClyA-RR-E129R | No activity | No activity | No activity | No | No |
| ClyA-RR-1'R | +184 ± 8 −101 ± 3 | 1.8 ± 0.1 | −150 | + | − |
| ClyA-RR-1'R-E7S | +176 ± 5 −109 ± 3 | 1.6 ± 0.1 | −50 | + | − |

TABLE 2-continued

Pore engineering DNA translocation from the trans side. Each data point is the average of at least three experiments and the error is the standard deviation. Experiments were carried out in 0.15M NaCl, 15 mM Tris HCl, pH 7.5 solutions. The activity of the nanopores were tested by adding 0.01-0.1 ng oligomeric protein to the trans chamber. A negative activity indicates that no channel insertions were observed. $V_G$ represents the maximum applied voltage at which no gating events were observed within 30 s. DNA capture indicates that only transient current blockades were observed upon the addition of biotinylated dsDNA in complex with neutravidin. DNA translocation indicates that a dsDNA rotaxane could be formed.

| Pore variants | $I_O + 100$ mV $I_O$ 100 Mv (pA) | Rectification ratio | $V_G$, (mV) | DNA Capture | DNA Translocation |
|---|---|---|---|---|---|
| ClyA-RR-1'R-D21S | +179 ± 9 −108 ± 5 | 1.7 ± 0.1 | −50 | + | − |

TABLE 3

DNA molecules used in this work. 1 was formed by incubating 1a with a 20% excess of 1b and purified by affinity chromatography as described in Methods. 1* was formed by incubating 1a with a 20% excess of 1b without further purification. The complementary sequences in the two DNA strands are shown in italics. The suffix bio indicates a biotin moiety.

| Name | DNA sequence |
|---|---|
| 1a | 5'- GGATGA CCT GAT CCA GAT ATT TAT TAT ACA GGT CCA GCG CAC CGT CAG CCC AAT CGC ACT TTT CAC AAA AAG AGA GAG AGATCG ATT ACC /3Bio/-3' (SEQ ID NO: 5) |
| 1b | 5'- GGT AAT CGA TCT CTC TCT CTT TTT GTG AAA AGT GCG ATT GGG CTG ACG GTG CGC TGG ACC TGT ATA ATA AAT ATC TGG ATC AGG TCA TCC-3' (SEQ ID NO: 6) |
| 1c | 5'- GGT AAT CGATCT CTC TCT CTT TTT GTG AAA AGT GCG ATT GGG CTG ACG GTG CGCTGG AC-/3Bio/-3' (SEQ ID NO: 7) |
| 1d | 5'-CTG TAT AAT AAA TAT CTG GAT CAG GTC ATC C /3Bio/-3' (SEQ ID NO: 8) |
| 2a | 5'- /5Bio/CCG TAGTTT GGG ATG ACCTGA TCC AGATAT TTATTATAC AGGTCC AGC GCA CCGTCA GCC CAA TCG CACTTT TCA CAA AAA GAG AGA GAG ATC GAT TAC C-3' (SEQ ID NO: 9) |
| 2b | 5'- /5Bio/GGT AAT CGATCT CTC TCT CTT TTT GTG AAA AGT GCG ATT GGG CTG ACG GT-3' (SEQ ID NO: 10) |

TABLE 4

Ionic selectivity of selected ClyA nanopores. Permeability ratio ($P_{Na+}/P_{Cl-}$) and reversal potential (Vr) for ClyA variant nanopores reported as average ± standard deviation. Four or more single channels were measured for each variant. The buffer used were: 15 mM TRIS•HCl pH 7.5, with 1M NaCl in the cis chamber and 150 mM in the trans chamber.

| Pore variants | $V_r$, mV | $P_{Na+}/P_{Cl-}$ |
|---|---|---|
| ClyA-AS | +11.5 ± 0.7 | 1.92 ± 0.08 |
| ClyA-R | +11.9 ± 1.6 | 1.97 ± 0.08 |
| ClyA-RR | +11.4 ± 0.9 | 1.91 ± 0.10 |

Table 5: IV curves for ClyA mutants. The electrical recordings were carried out in 0.15 M NaCl, 15 mM Tris HCl, pH 7.5, at 22° C. Each data point is the average of at least three experiments and the error is the standard deviation.

TABLE 5

| Voltage (mV) | ClyA-AS | ClyA-AS-S110R (ClyA-R) | ClyA-R-D56R | ClyA-R-Q8K | ClyA-R-D64R (ClyA-RR) |
|---|---|---|---|---|---|
| −100 | −138 ± 6 | −128 ± 2 | −128 ± 2 | −147 ± 18 | −111 ± 2 |
| −90 | −126 ± 6 | −118 ± 1 | −119 ± 2 | −134 ± 15 | −104 ± 2 |
| −80 | −115 ± 5 | −107 ± 1 | −108 ± 2 | −120 ± 12 | −96.2 ± 1.8 |
| −70 | −102 ± 5 | −96.2 ± 1.3 | −97.3 ± 1.3 | −107 ± 10 | −87.5 ± 1.4 |
| −60 | −89.1 ± 4.3 | −84.6 ± 1.1 | −85.9 ± 0.9 | −93.2 ± 7.9 | −78.1 ± 1.3 |
| −50 | −75.8 ± 3.6 | −72.4 ± 0.9 | −73.2 ± 0.3 | −78.1 ± 4.9 | −67.4 ± 1.1 |
| −40 | −61.8 ± 2.9 | −59.3 ± 0.9 | −60.4 ± 0.4 | −63.9 ± 4.2 | −56 ± 1 |
| −30 | −47.1 ± 2.2 | −45.6 ± 0.6 | −46.2 ± 0.2 | −48.6 ± 2.8 | −43.6 ± 0.7 |
| −20 | −31.9 ± 1.5 | −31.2 ± 0.4 | −31.7 ± 0.3 | −32.3 ± 2 | −30 ± 1 |
| −10 | −16.2 ± 0.7 | −15.9 ± 0.2 | −16.2 ± 0.3 | −16.7 ± 0.9 | −15.4 ± 0.2 |
| 0 | 0 | 0 | 0 | 0 | 0 |
| +10 | 16.8 ± 0.9 | 16.8 ± 0.1 | 17.1 ± 0.1 | 17 ± 2 | 16.5 ± 0.1 |
| +20 | 34.2 ± 1.7 | 34.4 ± 0.3 | 35.2 ± 0.3 | 35.3 ± 3.1 | 34 ± 1 |
| +30 | 52.1 ± 2.5 | 52.5 ± 0.6 | 53.5 ± 0.9 | 54.4 ± 4.3 | 52.3 ± 0.3 |
| +40 | 70.5 ± 3.4 | 71.6 ± 0.7 | 72.9 ± 1.1 | 73.8 ± 5.7 | 71.5 ± 0.3 |
| +50 | 89.0 ± 4.5 | 91.3 ± 0.8 | 93 ± 2 | 94.3 ± 6.8 | 91.8 ± 0.5 |
| +60 | 108 ± 5 | 112 ± 1 | 114 ± 3 | 115 ± 8 | 112 ± 1 |
| +70 | 128 ± 7 | 132 ± 1 | 135 ± 4 | 137 ± 10 | 13 ± 1 |
| +80 | 148 ± 8 | 154 ± 1 | 157 ± 5 | 157 ± 12 | 156 ± 1 |
| +90 | 168 ± 10 | 175 ± 2 | 179 ± 6 | 181 ± 14 | 179 ± 1 |
| +100 | 190 ± 13 | 198 ± 1 | 202 ± 8 | 202 ± 16 | 202 ± 1 |

TABLE 5-continued

| Voltage (mV) | ClyA-R E11S | ClyA-R-D122R | ClyA-R-E129R | ClyA-R-D56R-Q8K |
|---|---|---|---|---|
| −100 | −165 ± 19 | −99.8 ± 2.1 | −161 ± 24 | −150 ± 15 |
| −90 | −150 ± 17 | −93.8 ± 2.1 | −145 ± 23 | −135 ± 14 |
| −80 | −136 ± 15 | −87.3 ± 1.8 | −130 ± 20 | −123 ± 13 |
| −70 | −120 ± 13 | −78.8 ± 2.6 | −114 ± 18 | −110 ± 11 |
| −60 | −105 ± 11 | −70.7 ± 2.2 | −98.3 ± 15.1 | −94.9 ± 10.8 |
| −50 | −88.7 ± 9.3 | −62.5 ± 1.3 | −81.2 ± 11 | −81 ± 9 |
| −40 | −71.9 ± 7.3 | −52.3 ± 0.9 | −65.4 ± 8.9 | −65.3 ± 7.9 |
| −30 | −54.6 ± 5.3 | −41.1 ± 0.5 | −49.2 ± 6.5 | −49.9 ± 6.4 |
| −20 | −36.9 ± 3.6 | −28.6 ± 0.4 | −32.9 ± 4.4 | −33 ± 5 |
| −10 | −18.6 ± 1.8 | −14.9 ± 0.2 | −16.6 ± 2.4 | −16.5 ± 2.5 |
| 0 | 0 | 0 | 0 | 0 |
| +10 | 19 ± 2 | 16 ± 0 | 16.8 ± 2.5 | 17.9 ± 2.3 |
| +20 | 38.4 ± 3.4 | 33.3 ± 0.5 | 33.8 ± 5.1 | 35.4 ± 5.6 |
| +30 | 58 ± 5 | 51.6 ± 0.5 | 50.7 ± 7.6 | 54 ± 9 |
| +40 | 77.7 ± 6.9 | 71.1 ± 0.8 | 67.6 ± 10.2 | 72.5 ± 12.5 |
| +50 | 97.8 ± 8.2 | 91.6 ± 0.8 | 84.6 ± 12.6 | 91.7 ± 15.9 |
| +60 | 119 ± 10 | 113 ± 1 | 101 ± 15 | 114 ± 17 |
| +70 | 140 ± 11 | 135 ± 1 | 118 ± 18 | 133 ± 20 |
| +80 | 159 ± 13 | 158 ± 2 | 136 ± 20 | 154 ± 23 |
| +90 | 181 ± 15 | 182 ± 2 | 153 ± 23 | 182 ± 20 |
| +100 | 201 ± 13 | 207 ± 2 | 171 ± 26 | 207 ± 20 |

| Voltage (mV) | ClyA-RR-E7S | ClyA-RR-E11S | ClyA-RR-D21S | ClyA-RR-D21K | ClyA-RR-D32N |
|---|---|---|---|---|---|
| −100 | −111 ± 4 | −128 ± 11 | −113 ± 9 | −120 ± 1 | −108 ± 1 |
| −90 | −103 ± 3 | −119 ± 10 | −106 ± 8 | −109 ± 0 | −101 ± 1 |
| −80 | −95.4 ± 3.4 | −109 ± 9 | −96.7 ± 7.9 | −99.1 ± 0.3 | −93.2 ± 0.9 |
| −70 | −87 ± 3 | −98.9 ± 8.2 | −87.6 ± 6.5 | −88.1 ± 0.1 | −84.7 ± 0.7 |
| −60 | −77.3 ± 2.8 | −87.9 ± 7.5 | −77.9 ± 5.4 | −76.6 ± 0.2 | −75.5 ± 0.6 |
| −50 | −66.3 ± 2.2 | −75.5 ± 6.2 | −67.1 ± 4.5 | −65 ± 0 | −65.2 ± 0.5 |
| −40 | −54.7 ± 1.9 | −62.5 ± 5.2 | −55.2 ± 3.8 | −53.2 ± 0.1 | −54.2 ± 0.5 |
| −30 | −42.3 ± 1.4 | −48.3 ± 4 | −42.3 ± 3.3 | −40.5 ± 0.1 | −42.1 ± 0.4 |
| −20 | −28.9 ± 1 | −33.2 ± 2.8 | −29 ± 2 | −27.5 ± 0.1 | −29 ± 0 |
| −10 | −15 ± 0 | −17 ± 1 | −15.1 ± 0.9 | −13.9 ± 0 | −15 ± 0 |
| 0 | 0 | 0 | 0 | 0 | 0 |
| +10 | 15 ± 1 | 18 ± 1 | 16 ± 1 | 14.3 ± 0 | 15.6 ± 0.6 |
| +20 | 31.2 ± 2.4 | 36.8 ± 3.1 | 32.5 ± 2.2 | 29.2 ± 0 | 32.2 ± 1.3 |
| +30 | 49.1 ± 2 | 56.3 ± 4.6 | 50.1 ± 3.1 | 44.3 ± 0.1 | 49.6 ± 2.1 |
| +40 | 66.2 ± 3.7 | 76.8 ± 6.6 | 67.2 ± 5.1 | 60 ± 0 | 67.9 ± 2.8 |
| +50 | 85.7 ± 3.3 | 98 ± 8 | 87.3 ± 5.5 | 75.6 ± 0.5 | 87 ± 4 |
| +60 | 105 ± 4 | 120 ± 11 | 107 ± 6 | 92.2 ± 0.1 | 107 ± 5 |
| +70 | 125 ± 4 | 142 ± 13 | 127 ± 7 | 109 ± 0 | 127 ± 5 |
| +80 | 145 ± 5 | 165 ± 15 | 148 ± 8 | 125 ± 0 | 149 ± 6 |
| +90 | 166 ± 5 | 189 ± 17 | 170 ± 9 | 142 ± 0 | 171 ± 7 |
| +100 | 188 ± 6 | 214 ± 19 | 193 ± 11 | 160 ± 0 | 198 ± 4 |

| Voltage (mV) | ClyA-RR-E7S-D21S | ClyA-RR-E7S-D32N | ClyA-RR-1R (ClyA-3R) | ClyA-3R-E7S | ClyA-3R-D21S |
|---|---|---|---|---|---|
| −100 | −120 ± 4 | −104 ± 6 | −112 ± 9 | −109 ± 3 | −108 ± 5 |
| −90 | −109 ± 1 | −96.9 ± 5.6 | −103 ± 12 | −101 ± 2 | −101 ± 4 |
| −80 | −99.9 ± 2.1 | −89.2 ± 4.7 | −93.5 ± 11.8 | −93.2 ± 2.9 | −93.1 ± 4 |
| −70 | −88.6 ± 1 | −80.9 ± 4.2 | −86 ± 10 | −84.8 ± 1.1 | −83.4 ± 2 |
| −60 | −80.4 ± 1.7 | −71.9 ± 3.5 | −77.6 ± 8.2 | −74.3 ± 0.9 | −73.2 ± 1.3 |
| −50 | −67.4 ± 2.7 | −62 ± 3 | −65.9 ± 7.1 | −63.7 ± 1 | −63.3 ± 1 |
| −40 | −56.2 ± 2 | −51.4 ± 2.3 | −54.6 ± 5.6 | −52.8 ± 1 | −52.3 ± 0.8 |
| −30 | −43.4 ± 1.1 | −39.8 ± 1.7 | −42.5 ± 3.6 | −40.6 ± 1 | −40.6 ± 0.6 |
| −20 | −28.9 ± 1.6 | −27.4 ± 1.2 | −30 ± 3 | −28.1 ± 0.5 | −28 ± 0 |
| −10 | −13.5 ± 1 | −14.2 ± 0.5 | −14.9 ± 1.7 | −14.3 ± 0.3 | −14.4 ± 0.2 |
| 0 | 0 | 0 | 0 | 0 | 0 |
| +10 | 16.4 ± 2.4 | 15 ± 0 | 16.1 ± 0.8 | 15.1 ± 0.5 | 15.3 ± 0.3 |
| +20 | 32.2 ± 1.4 | 30.7 ± 1 | 32.4 ± 2.1 | 30.9 ± 1.1 | 31.5 ± 1.1 |
| +30 | 50.3 ± 2.1 | 47.4 ± 1.5 | 50 ± 2 | 47.5 ± 1.5 | 48.3 ± 1.8 |
| +40 | 68 ± 2 | 64.7 ± 1.9 | 68.7 ± 2.7 | 64.5 ± 2 | 65.8 ± 2.4 |
| +50 | 85.8 ± 1.1 | 82.7 ± 2.4 | 88 ± 3 | 81.7 ± 2.5 | 83.7 ± 3.3 |
| +60 | 103 ± 1 | 101 ± 3 | 106 ± 5 | 99.5 ± 2.9 | 102 ± 4 |
| +70 | 122 ± 4 | 121 ± 3 | 126 ± 5 | 118 ± 3 | 121 ± 6 |
| +80 | 143 ± 0 | 140 ± 3 | 149 ± 9 | 137 ± 4 | 140 ± 6 |
| +90 | 163 ± 2 | 160 ± 3 | 170 ± 5 | 156 ± 4 | 160 ± 7 |
| +100 | 184 ± 0 | 182 ± 4 | 191 ± 11 | 176 ± 5 | 179 ± 9 |

TABLE 6

IV curves of ClyA variants under asymmetric salt concentrations. Four or more single channels were measured for each variant. Each data is reported as the average ± standard deviation. The buffer used was 15 mM TRIS•HCl pH 7.5, while the cis chamber contained 1M NaCl and the trans chamber 150 mM. The electrical recordings were carried out in 0.15M NaCl, 15 mM Tris HCl, pH 7.5, at 22° C. Data were recorded by applying a 2-kHz low-pass Bessel filter and using a 100 ps (10 kHz) sampling rate.

| IV Voltage (mV) | ClyA Ionic permeability Open pore current, pA (Average ± Standard Deviation) | | |
|---|---|---|---|
| | ClyA—AS | ClyA—R | ClyA—RR |
| 20 | 26.5 ± 0.7 | 36.7 ± 14.1 | 32.4 ± 4.3 |
| 19 | 23.1 ± 0.9 | 32.5 ± 13 | 28.6 ± 2.7 |
| 18 | 19.8 ± 0.5 | 27.6 ± 12.8 | 25.2 ± 2.5 |
| 17 | 16.6 ± 0.9 | 23.4 ± 10.8 | 21.3 ± 1.8 |
| 16 | 13.6 ± 1.8 | 17.9 ± 10.7 | 16.6 ± 1.2 |
| 15 | 9.9 ± 1.9 | 14.4 ± 9.7 | 12.8 ± 1.9 |
| 14 | 7.2 ± 1.2 | 7.8 ± 9.3 | 10.2 ± 1.2 |
| 13 | 4.4 ± 1.1 | 2.9 ± 8.9 | 7.2 ± 1.4 |
| 12 | 2.5 ± 1.4 | −1.7 ± 9.4 | 1.8 ± 1.3 |
| 11 | −0.7 ± 2.5 | −5.6 ± 8.6 | −0.8 ± 1.9 |
| 10 | −3.8 ± 2.7 | −12.7 ± 7.3 | −4 ± 1 |
| 9 | −7.3 ± 2.7 | −15.6 ± 8 | −9.3 ± 3.1 |
| 8 | −10.7 ± 1.5 | −22.3 ± 6.3 | −11.9 ± 0.5 |
| 7 | −13.4 ± 4.3 | −24.5 ± 5.9 | −15.5 ± 2.6 |
| 6 | −16.2 ± 0.9 | −31.2 ± 5.8 | −19.8 ± 3.2 |
| 5 | −18 ± 2 | −35.2 ± 4.5 | −23.1 ± 3.1 |
| 4 | −22.3 ± 2.5 | −40.4 ± 5.2 | −25.7 ± 1.7 |
| 3 | −25 ± 2 | −43.7 ± 3.5 | −30.1 ± 2.9 |
| 2 | −27.8 ± 3.1 | −51.2 ± 4.1 | −33.8 ± 4.5 |
| 1 | −30.5 ± 3.1 | −55.6 ± 2.1 | −36.9 ± 4.8 |
| 0 | −34.9 ± 2.7 | −60.7 ± 2 | −40.7 ± 5 |
| −1 | −37.1 ± 3.5 | −65.1 ± 2.6 | −44.4 ± 3.8 |
| −2 | −41 ± 3 | −68.8 ± 3.8 | −48.2 ± 4.2 |
| −3 | −42.1 ± 3.9 | −74.8 ± 3.6 | −51.3 ± 6.5 |
| −4 | −46.2 ± 4.2 | −79.8 ± 2.1 | −54.8 ± 7.9 |
| −5 | −48.8 ± 4.2 | −85.2 ± 2.5 | −57.8 ± 6.5 |
| −6 | −51.5 ± 3.5 | −90 ± 3 | −61.2 ± 7.8 |
| −7 | −55.1 ± 6.3 | −94 ± 4 | −66.2 ± 7.3 |
| −8 | −57.8 ± 5.5 | −100 ± 3 | −68.6 ± 10.7 |
| −9 | −61 ± 4 | −103 ± 3 | −73.1 ± 8.3 |
| −10 | −62.8 ± 4.9 | −109 ± 4 | −76.5 ± 7.9 |
| −11 | −66.2 ± 5 | −114 ± 4 | −80.1 ± 9.1 |
| −12 | −69.7 ± 6 | −117 ± 4 | −83.6 ± 9.9 |
| −13 | −74.7 ± 5.5 | −123 ± 4 | −86.6 ± 8.7 |
| −14 | −74.8 ± 6.1 | −129 ± 5 | −91.1 ± 11.2 |
| −15 | −78.3 ± 5.7 | −134 ± 7 | −93.5 ± 10.7 |
| −16 | −80.2 ± 6.2 | −137 ± 8 | −96.7 ± 9.7 |
| −17 | −84.2 ± 6.4 | −144 ± 7 | −100 ± 13 |
| −18 | −87.6 ± 7.6 | −148 ± 8 | −104 ± 12 |
| −19 | −90.4 ± 7.7 | −153 ± 8 | −108 ± 12 |
| −20 | −92.4 ± 7.3 | −158 ± 8 | −112 ± 11 |

Table 7: ssDNA (1a) and dsDNA (1) translocation through ClyA-RR nanopores. Three or more single channels were measured for each condition. Data are reported as the average ± standard deviation. The electrical recordings were carried out in 15 mM Tris-HCl. pH 7.5 at 22° C. Data were recorded by applying a 10-kHz low-pass Bessel filter and using a 20 μs (50 kHz) sampling rate.

TABLE 7

| [NaCl] (M) | $I_{RES}$ | $\tau_{off}$ (ms) | $\tau_{on}$ (ms) |
|---|---|---|---|
| ssDNA (1a) | | | |
| 0.15 | 0.92 ± 0.00 | 0.54 ± 0.28 | 8.5 ± 1.1 |
| 0.3 | 0.89 ± 0.01 | 0.18 ± 0.04 | 44 ± 1 |
| 0.5 | 0.88 ± 0.02 | 0.12 ± 0.02 | 112 ± 14 |
| 1 | 0.82 ± 0.01 | 0.13 ± 0.01 | 232 ± 36 |
| 2 | 0.84 ± 0.01 | 0.12 ± 0.02 | 393 ± 17 |
| 2.5 | 0.78 ± 0.01 | 0.18 ± 0.02 | 500 ± 50 |
| dsDNA (1) | | | |
| 0.15 | 0.92 ± 0.00 | 0.29 ± 0.07 | 40 ± 13 |
| 0.6 | 0.83 ± 0.03 | 0.26 ± 0.09 | 162 ± 31 |
| 1 | 0.76 ± 0.01 | 0.26 ± 0.09 | 214 ± 18 |
| 2 | 0.75 ± 0.04 | 0.33 ± 0.07 | 532 ± 52 |
| 2.5 | 0.75 ± 0.01 | 0.60 ± 0.48 | 641 ± 37 |

SEQUENCE LISTING:

| Description | Sequence |
|---|---|
| Protein sequence for S. typhi ClyA (ClyA-WT) SEQ ID NO: 1 | MTGIFAEQTVEVVKSAIETADGALDLYNKYLDQVIPWKTFDETIKELSRFKQE YSQEASVLVGDIKVLLMDSQDKYFEATQTVYEWCGVVTQLLSAYILLFDEYNE KKASAQKDILIRILDDGVKKLNEAQKSLLTSSQSFNNASGKLLALDSQLTNDF SEKSSYFQSQVDRIRKEAYAGAAAGIVAGPFGLIISYSIAAGVIEGKLIPELN NRLKTVQNFFTSLSATVKQANKDIDAAKLKLATEIAAIGEIKTETETTRFYVD YDDLMLSLLKGAAKKMINTCNEYQQRHGKKTLFEVPDV |
| Protein sequence for ClyA-AS SEQ ID NO: 2 | MTGIFAEQTVEVVKSAIETADGALDLYNKYLDQVIPWKTFDETIKELSRFKQE YSQEASVLVGDIKVLLMDSQDKYFEATQTVYEWAGVVTQLLSAYIQLFDGYNE KKASAQKDILIRILDDGVKKLNEAQKSLLTSSQSFNNASGKLLALDSQLTNDF SEKSSYYQSQVDRIRKEAYAGAAAGIVAGPFGLIISYSIAAGVVEGKLIPELN NRLKTVQNFFTSLSATVKQANKDIDAAKLKLATEIAAIGEIKTETETTRFYVD YDDLMLSLLKGAAKKMINTSNEYQQRHGRKTLFEVPDVGSSYHHHHH* |
| Nucleotide sequence for S. typhi ClyA (ClyA-WT) SEQ ID NO: 3 | CCTGCGTAGATAAGCAGGAAGCAGGCAGTATTTCCAGCTTCTGGAATGTTAAA GCTACAAAAGTTGTCTGGAGGTAATAGGTAAGAATACTTTATAAAACAGGTAC TTAATTGCAATTTATATATTTAAAGAGGCAAATGATTATGACCGGAATATTTG CAGAACAAACTGTAGAGGTAGTTAAAAGCGCGATCGAAACCGCAGATGGGGCA TTAGATCTTTATAACAAATACCTCGACCAGGTCATCCCCTGGAAGACCTTTGA TGAAACCATAAAAGAGTTAAGCCGTTTTAAACAGGAGTACTCGCAGGAAGCTT |

SEQUENCE LISTING:

| Description | Sequence |
|---|---|
| | CTGTTTTAGTTGGTGATATTAAAGTTTTGCTTATGGACAGCCAGGACAAGTAT<br>TTTGAAGCGACACAAACTGTTTATGAATGGTGTGGTGTCGTGACGCAATTACT<br>CTCAGCGTATATTTTACTATTTGATGAATATAATGAGAAAAAAGCATCAGCCC<br>AGAAAGACATTCTCATTAGGATATTAGATGATGGTGTCAAGAAACTGAATGAA<br>GCGCAAAAATCTCTCCTGACAAGTTCACAAAGTTTCAACAACGCTTCCGGAAA<br>ACTGCTGGCATTAGATAGCCAGTTAACTAATGATTTTTCGGAAAAAAGTAGTT<br>ATTTCCAGTCACAGGTGGATAGAATTCGTAAGGAAGCTTATGCCGGTGCTGCA<br>GCCGGCATAGTCGCCGGTCCGTTTGGATTAATTATTTCCTATTCTATTGCTGC<br>GGGCGTGATTGAAGGGAAATTGATTCCAGAATTGAATAACAGGCTAAAAACAG<br>TGCAAAATTTCTTTACTAGCTTATCAGCTACAGTGAAACAAGCGAATAAAGAT<br>ATCGATGCGGCAAAATTGAAATTAGCCACTGAAATAGCAGCAATTGGGGAGAT<br>AAAAACGGAAACCGAAACAACCAGATTCTACGTTGATTATGATGATTTAATGC<br>TTTCTTTATTAAAAGGAGCTGCAAAGAAAATGATTAACACCTGTAATGAATAC<br>CAACAAAGACACGGTAAGAAGACGCTTTTCGAGGTTCCTGACGTCTGATACAT<br>TTTCATTCGATCTGTGTACTTTTAACGCCCGATAGCGTAAAGAAAATGAGAGA<br>CGGAGAAAAAGCGATATTCAACAGCCCGATAAACAAGAGTCGTTACCGGGCTG<br>ACGAGGTTATCAGGCGTTAAGCTGGTAG |
| Nucleotide sequence for ClyA-AS<br>SEQ ID NO: 4 | ATGACGGGTATCTTTGCGGAACAGACGGTGGAAGTTGTGAAAAGTGCGATTGA<br>AACGGCTGACGGTGCGCTGGACCTGTATAATAAATATCTGGATCAGGTCATCC<br>CGTGGAAAACCTTTGACGAAACGATTAAAGAACTGAGCCGTTTCAAACAGGAA<br>TACAGTCAAGAAGCGTCCGTCCTAGTGGGCGATATCAAAGTGCTGCTGATGGA<br>TTCTCAGGACAAATATTTTGAAGCTACCCAAACGGTTTACGAATGGGCGGGTG<br>TGGTTACCCAGCTGCTGTCCGCATATATTCAGCTGTTCGATGGATACAATGAG<br>AAAAAAGCGAGCGCGCAGAAAGACATTCTGATCCGCATTCTGGATGACGGCGT<br>GAAAAAACTGAATGAAGCCCAGAAATCGCTGCTGACCAGCTCTCAATCATTTA<br>ACAATGCCTCGGGTAAACTGCTGGCACTGGATAGCCAGCTGACGAACGACTTT<br>TCTGAAAAAAGTTCCTATTACCAGAGCCAAGTCGATCGTATTCGTAAAGAAGC<br>CTACGCAGGTGCCGCAGCAGGTATTGTGGCCGGTCCGTTCGGTCTGATTATCT<br>CATATTCAATTGCTGCGGGCGTTGTCGAAGGTAAACTGATTCCGGAACTGAAC<br>AATCGTCTGAAAACCGTTCAGAACTTTTTCACCAGTCTGTCTGCTACGGTCAA<br>ACAAGCGAATAAAGATATCGACGCCGCAAAACTGAAACTGGCCACGGAAATCG<br>CTGCGATTGGCGAAATCAAAACCGAAACGGAAACCACGCGCTTTTATGTTGAT<br>TACGATGACCTGATGCTGAGCCTGCTGAAAGGTGCCGCGAAGAAAATGATTAA<br>TACCTCTAATGAATATCAGCAGCGTCACGGTAGAAAAACCCTGTTTGAAGTCC<br>CGGATGTGGGCAGCAGCTACCACCATCATCACCACTAAAAGCTT |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A modified ClyA nanopore subunit polypeptide comprising an amino acid sequence that is at least 95% identical to the amino acid sequence as set forth in SEQ ID NO: 1 or in SEQ ID NO: 2, and wherein the amino acid sequence comprises a first positively charged substitution located at E106, S110, D114, D121, D122, E129, E85, E78, D268, D267, D265, or E258 of SEQ ID NO: 1 or 2; and/or is located at an amino acid between position 78 and 106 of SEQ ID NO: 1 or 2; and a second positively-charged amino acid substitution corresponding to replacement of a negatively charged amino acid with a positively-charged amino acid at one or more positions corresponding to D74, D71, D64, E53, E161, D158, D46, E42, and D41 of SEQ ID NO: 1 or SEQ ID NO: 2.

2. The modified ClyA nanopore subunit polypeptide of claim 1, wherein the amino acids at positions 1-32 of SEQ ID NO: 1 or SEQ ID NO: 2 yield a net negative charge.

3. The modified ClyA nanopore subunit polypeptide of claim 1, wherein the first positively-charged amino acid substitution is located at position 110 of SEQ ID NO: 1 or SEQ ID NO: 2.

4. The modified ClyA nanopore subunit polypeptide of claim 1, wherein the second positively-charged amino acid substitution is located at position 64 of SEQ ID NO: 1 or SEQ ID NO:2.

5. The modified ClyA nanopore subunit polypeptide of claim 1, wherein the first and second positively-charged amino acid substitutions each independently includes an arginine, a histidine, or a lysine.

6. A composition comprising at least one modified ClyA nanopore that comprises the modified ClyA nanopore subunit polypeptide of claim 1.

7. The composition of claim 6, further comprising a membrane, wherein the modified ClyA nanopore is present in the membrane.

8. A method of characterizing a target polynucleotide, the method comprising
 (a) providing, in a low ionic strength solution of about 150 mM to about 300 mM, a modified ClyA nanopore comprising the modified ClyA nanopore subunit polypeptide of claim 1 and a membrane, wherein the modified ClyA nanopore is present in the membrane;
 (b) adding in the low ionic strength solution of step (a) the target polynucleotide; and
 (c) measuring, during application of a potential across the nanopore, ion flow through the modified ClyA nanopore, wherein the ion flow measurements are indicative of one or more characteristics of the target polynucleotide.

9. The method of claim 8, wherein the target polynucleotide is a single-stranded DNA or a double-stranded DNA.

10. A homo-multimeric modified ClyA nanopore comprising a plurality of the modified ClyA nanopore subunit polypeptides of claim 1.

11. The homo-multimeric modified ClyA nanopore of claim 10, wherein the modified ClyA nanopore comprises 12, 13, or 14 subunit polypeptides.

12. A hetero-multimeric modified ClyA nanopore comprising at least one modified ClyA nanopore subunit polypeptide of claim 1.

13. The hetero-multimeric modified ClyA nanopore of claim 12, wherein the modified ClyA nanopore comprises 12, 13, or 14 subunit polypeptides.

\* \* \* \* \*